US008927804B2

(12) United States Patent
Wipff et al.

(10) Patent No.: US 8,927,804 B2
(45) Date of Patent: Jan. 6, 2015

(54) LOLIUM PERENNE SUBSP. STOLONIFERUM; PERENNIAL RYEGRASS WITH DETERMINATE-STOLONS

(75) Inventors: Joseph K. Wipff, Canby, OR (US); Devesh Singh, Albany, OR (US)

(73) Assignee: Barenbrug USA, Inc., Tangent, OR (US)

( * ) Notice: Subject to any disclaimer, the term of this patent is extended or adjusted under 35 U.S.C. 154(b) by 80 days.

(21) Appl. No.: 13/298,093

(22) Filed: Nov. 16, 2011

(65) Prior Publication Data

US 2012/0124687 A1    May 17, 2012

Related U.S. Application Data

(60) Provisional application No. 61/414,206, filed on Nov. 16, 2010, provisional application No. 61/415,711, filed on Nov. 19, 2010.

(51) Int. Cl.
| | | |
|---|---|---|
| A01H 5/00 | (2006.01) | |
| A01H 5/04 | (2006.01) | |
| A01H 5/06 | (2006.01) | |
| A01H 5/10 | (2006.01) | |
| A01H 1/04 | (2006.01) | |
| A01H 1/08 | (2006.01) | |
| A01H 5/12 | (2006.01) | |

(52) U.S. Cl.
CPC ........................................ *A01H 5/12* (2013.01)
USPC ........................................ 800/266; 800/269

(58) Field of Classification Search
None
See application file for complete search history.

(56) References Cited

U.S. PATENT DOCUMENTS 7,696,418 B2    4/2010  Ledeboer

OTHER PUBLICATIONS

Bonos, S.A. International Turfgrass Society Research Journal vol. 9, 2001; pp. 137-145.*
Henderson, J.J. et al. Agron. J. (2005), 97:1153-1157.*
Ruemmele, B., Chapter 11. Agrostis Capillaris, in Turfgrass Biology, Genetics and Breeding, eds. M.D. Casler and R.D. Duncan, John Wiley and Sons, Inc., Hoboken, NJ pp. 187-200.*
Bajaj, S. et al. Plant Cell Reports (2006) vol. 25; pp. 651-659.*
Ruemmele, B., Chapter 11. Agrostis Capillaris, in Turfgrass Biology, Genetics and Breeding, eds. M.D. Casler and R.D. Duncan, John Wiley and Sons, Inc., Hoboken, NJ pp. 187-200 (2003).*
Anon. 2001. Turfgrass Seed 2001. Sports Turf Research Institute, Bingley, West Yorkshire, UK.
Aramendía, "El género *Lolium*: Claves dicotómicas," *Rev. Real Academia de Ciencias, Zaragoza 60*:143-155, 2005.
Beddows, "The Ryegrasses in British Agriculture: A Survey," Welsh Plant Breeding Station Bulletin 17:1-81, 1952.
Bonos et al., "Breeding Cool-Season Turfgrasses for Wear Tolerance Using a Wear Simulator," *International Turfgrass Society Research Journal 9*:137-145, 2001.
Canaway, "A Differential Slip Wear Machine (D.S.1) for the Artificial Simulation of Turfgrass Wear," *Journal of the Sports Turf Research Institute 52*:92-99, 1976.
Canaway, Wear Tolerance of Turfgrass Species. *Journal of the Sports Turf Research Institute 57*: 65-83, 1981.
Canaway, "Comparison of Real and Artificial Wear," *Journal of the Sports Turf Research Institute.* 57: 108-121, 1981.
Cockerham, "Cleated-Shoe Traffic Concentration on a Football Field," *California Turfgrass Culture 39*:11-12, 1989.
Cockerham and Brinkman, "A Simulator for Cleated-Shoe Sports Traffic on Turfgrass Research Plots," *California Turfgrass Culture 39*:9-10, 1989.
Cockerham et al., "Tolerance of Cool Season Turfgrasses to Sports Traffic.," *California Turfgrass Culture 39*:12-14, 1989.
Edmond, Some Effects of Sheep Treading on the Growth of 10 Pasture Species. *New Zealand Journal of Agricultural Research 7*:1-16, 1964.
Ellis, "An experimental approach to wear tolerance in *Lolium perenne*," Ph.D. Thesis, University of Liverpool, United Kingdom, 1981.
Harris et al. "Observations on the Spread of Perennial Ryegrass by Stolons in a Lawn," *New Zealand Journal of Agricultural Research 22*:61-68, 1979.
Hayes, "Stoloniferous Perennial Ryegrass (*Lolium perenne*) in Northern Ireland Paddocks," *Record of Agricultural Research, Ministry of Agriculture for Northern Ireland 19*:63-64, 1970.
Henderson, et al., "A New Apparatus to Simulate Athletic Field Traffic: The Cady Traffic Simulator," *Agron. J. 97*:1153-1157, 2005.
Jenkin, "Natural Selection of Grasses in Relation to the Grasses," in a Discussion on the Present State of the Theory of Natural Selection, *Proc. Roy. Soc., Ser. B. 121*:52-56, 1936.
Kydd, "The Effect of Intensive Sheep Stocking over a Five-Year Period on the Development and Production of the Sward," *Journal of the British Grassland Society 21*:284-288, 1966.
Lawson, "*Lolium*—Ryegrass," in The Agriculturist's Manual: Agricultural Plants Cultivated in Europe, Including practical observations respecting those suited to the Climate of Great Britain, and forming a Report of Lawson's Agricultural Museum in Edinburgh, pp. 102-113, Peter Lawson & Son, William Blackwood and Sons, Edinburgh, 1836.
Lush and Rogers, "Cutting Heights and the Biomass and Tiller Density of *Lolium perenne* Amenity Turfs," *J. Applied Ecology 29*:611-618, 1992.
Mitchell, "The Influence of Light and Temperature on the Growth of Pasture Species," *Proceedings of the Seventh International Grassland Congress*, pp. 58-69, 1956.
Oakley and Evans, "Rooting Stems in Timothy," *Journal of Agricultural Research 21*:173-178 + 2 plates, 1921.

(Continued)

*Primary Examiner* — Russell Kallis
(74) *Attorney, Agent, or Firm* — Klarquist Sparkman, LLP

(57) ABSTRACT

This disclosure provides perennial ryegrass plants having determinate-stolons developed by subjecting large number of perennial ryegrass plants to intense traffic. This grass can quickly repair (high regeneration potential) itself from traffic damage, and has good turf qualities compared to other perennial ryegrasses. The high regeneration potential gives it the ability to quickly repair itself from traffic damage and fill in open areas in turf. Methods of using the perennial ryegrass grass plants and seed are also provided. This grass is suitable for use in turf, for example turf that is exposed to significant traffic. This disclosure also provides methods of selecting for such grass plants.

50 Claims, 20 Drawing Sheets
(20 of 20 Drawing Sheet(s) Filed in Color)

(56) References Cited

OTHER PUBLICATIONS

Plot, "The Natural History of Oxfordshire, Being an Effay Towards the *Natural History* of England," Oxford University Press, 1677. (428 pages).

Scholz et al. "*Lolium edwardii* sp. nova (Gramineae) and its Relationship with *Schedonorus* sect. *Plantynia Dumort*," *Feddes Repertorium 111*:561-565, 2000.

Shildrick, "Shoot Numbers, Stem Bases and Persistence in Artificially Worn Perennial Ryegrass," *Journal of the Sports Turf Research Institute 57*:84-107, 1981.

Sinclair, *Hortus Gramineus Woburnesis*. 3$^{rd}$ Edition, James Ridgeway, London, 438 pp., 1826.

Terrell, "A Taxonomic Revision of the Genus *Lolium*," USDA-ARS, Technical Bulletin No. 1392. 65 pp., 1968.

Terrell, "*Lolium*," in Magnoliophyta: Commelinidae (*In part*): Poaceae, part 1. *Flora of North America North of Mexico 24*:454-459, eds. Barkworth, M.E., K.M. Capels, S. Long, and M.B. Piep, Oxford University Press, New York, 2007.

Thorogood, Chapter 7. Perennial Rygrass (*Lolium perenne* L.), in Turfgrass Biology, Genetics, and Breeding, eds. M.D. Casler and R.D. Duncan, John Wiley & Sons, Inc., Hoboken, NJ, pp. 75-105, 2003.

Vanini, et al. "Evaluating Traffic Stress by the Brinkman Traffic Simulator and Cady Traffic Simulator on a Kentucky Bluegrass Stand," *Crop Sci. 47*:782-786, 2007.

White, The Allometric Interpretation of the Self Thinning Rule, *J. Theor. Biol. 89*:475-500, 1981.

Wipff, "A New Combination in *Lolium perenne* (POACEAE:POEAE); *L. perenne* subsp. *Stoloniferum*," *J. Bot. Institute of Texas* 4(2):683-684, 2010.

Youngner, "Accelerated Wear Tests on Turfgrasses," *Agron. J. 53*:217-218, 1961.

Fei, "A New Species of the Genus *Lolium* L. (Poaceae) from Hubei (China)," *Guihaia 19*:205-206, 1999.

Essad, "Contribution à la Sytèmatique du Genere *Lolium*," Ministère de l'Agriculture, Annales de l'Institute Natlionale Recherche Agronomie, Paris, Amelioration des Plantes 4:325-351, 1954.

\* cited by examiner

FIG. 26
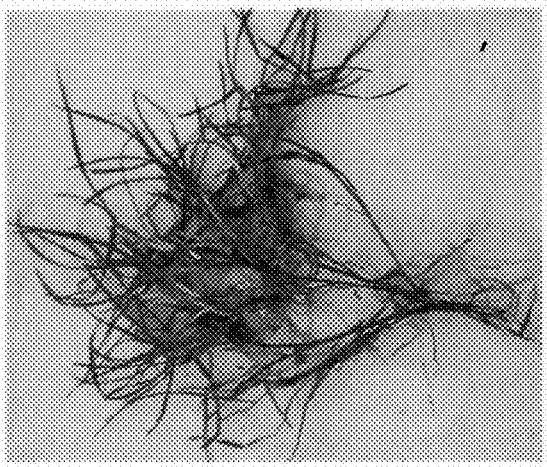
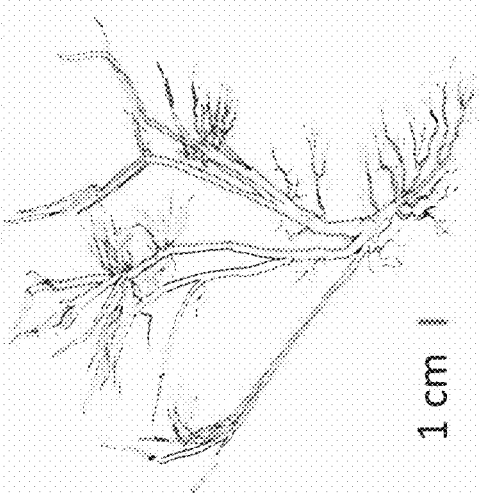
Lolium perenne subsp. stoloniferum
1 cm
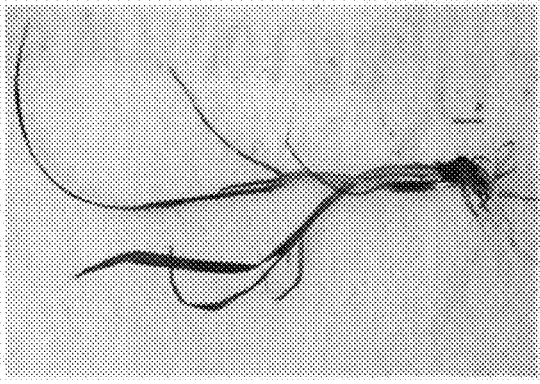
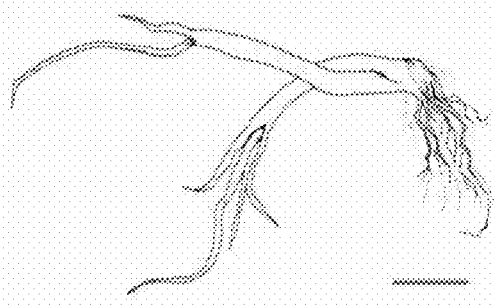
Lolium perenne subsp. perenne
1 cm

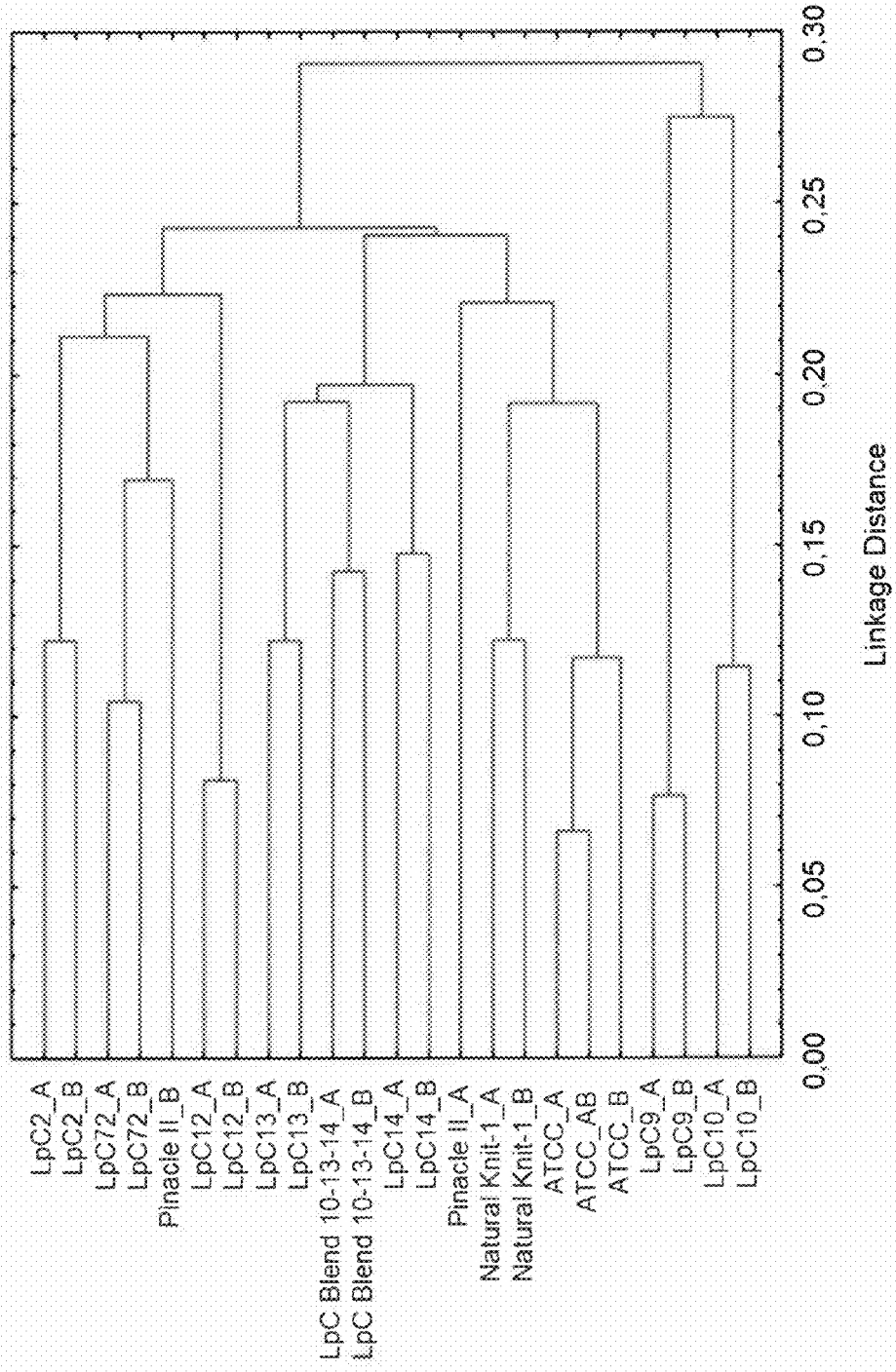

LOLIUM PERENNE SUBSP. STOLONIFERUM; PERENNIAL RYEGRASS WITH DETERMINATE-STOLONS

CROSS-REFERENCE TO RELATED APPLICATIONS

This application claims priority to U.S. Patent Application No. 61/414,206 filed Nov. 16, 2010 and 61/415,711 filed Nov. 19, 2010 both herein incorporated by reference.

FIELD

This disclosure relates to new perennial ryegrasses having determinate-stolons with superior wear tolerance, the ability to quickly repair (high regeneration potential) themselves from traffic damage, and good turf qualities. The high regeneration potential gives them the ability to quickly repair themselves from traffic damage and fill in open areas in turf. This new subspecies of perennial ryegrass was discovered through a novel intense selection protocol, which has improved the wear tolerance and visual appeal of these perennial ryegrasses, and provides ryegrass genotypes with determinate-stolons that enhance the wear tolerance, regenerative capabilities, and visual appeal.

BACKGROUND

The genus *Lolium* is indigenous to Europe, the North Atlantic Islands, temperate Asia, and North Africa (Terrell, 1968). However, the distribution and evolution of the genus has been affected by the involvement of humans who have encouraged its spread, not only, as a crop (*L. perenne* L. and *L. multiflorum* Lamarck—selected for forage and amenity characteristics), but also has encouraged the spread and evolution of other members of this genus as weeds in primitive agriculture [(*L. remotum* Schrank associated as a weed with flax, (*Linum usitatissimum* L.); and *L. temulentum* L. as weed in wheat (*Triticum aestivum* L.)] (Jenkin 1936). These later two *Lolium* species are only known as weeds of cultivated crops and probably evolved in close association with primitive agriculture (Terrell 1968).

Essad (1954) recognized five species within the genus and separated the species into two distinct groups based on reproductive biology: 1) an allogamous (cross-pollinated and largely self-incompatible) group including *L. perenne, L. multiflorum*, and *L. rigidum* Gaudin; and 2) an autogamous (self-pollinated and self-compatible) group including *L. temulentum* and *L. remotum*. Terrell (1968) published a taxonomic revision of the genus, in which he maintained the same classification of Essad (1954), recognizing two reproductively different groups (allogamous and autogamous), but recognized two additional species in the allogamous group and one additional species in the autogamous group.

Terrell's classification is a follows: 1) the *L. perenne* group or allogamous (cross-pollinated and largely self-incompatible) group: *L. perenne, L. multiflorum, L. rigidum* Gaudin, *L. subulatum* Visiani, and *L. canariense* Steudel; and 2) the *L. temulentum* group or autogamous (self-pollinated and self-compatible) group: *L. temulentum, L. remotum*, and *L. persicum* Boissier & Hohenacker.

Aramendia (2005), in a revision of the genus *Lolium*, recognized the same eight as Terrell (1968), but also treated *L. loweii* Menezes (endemic to the Madeira Islands) as distinct from *L. rigidum*. Also, since Terrell (1968), two additional species of *Lolium* have been described: *L. grandispicum* Fei from China (Fei 1999) and *L. edwardii* Scholz, Stierstorfer & Gaisberg endemic to the Island of El Hierro in Canary Islands (Scholz et al. 2000). However, there is now a debate as to their taxonomic distinctness. Regarding *L. grandispicum*, this taxon it is now considered a synonym of ×*Festulolium braunii* (K. Richt.) A. Camus, an intergeneric hybrid [*Festuca pratensis*×*Lolium multiflorum*]. *Lolium edwardii* is sometimes treated as a synonym of *L. canariense*. Thus, *Lolium* currently consists of 9-10 species worldwide, with six (or seven) taxa in the allogamous group: *L. perenne, L. multiflorum, L. rigidum, L. subulatum*, and *L. loweii*, and *L. canariense* (and possibly *L. edwardii*); and three taxa in the autogamous group: *L. temulentum, L. remotum*, and *L. persicum*.

Within five members of the *L. perenne* group (*L. perenne, L. multiflorum, L. rigidum, L. subulatum*, and *L. loweii*), there appears that repeated hybridizations and introgression has been occurring during the past several thousand years of human disturbance of habitats in the Mediterranean and southwest Asia.

Perennial ryegrass (*Lolium perenne* L.) is a cool-season perennial grass that is an important turf (amenities) and forage that has been introduced throughout the temperate world. In Britain, it is recorded as being deliberately sown and cultivated for pasture as early as 1677 (Plot, 1677, Beddows 1953). It is most extensively used in the United States and Europe as turf and forage. In Japan, Australia and New Zealand it used predominantly for forage, but is also important for golf courses and sports fields.

Turf-type (amenity) perennial ryegrass is used in temperate Europe, where it is naturalized, on winter games pitches and also for heavy-duty lawns, landscaping tennis courts, cricket fields, golf tees and fairways. It is sometimes used on its own, but often in mixture with red fescue (*Festuca rubra* L.) and bentgrasses (*Agrostis* spp.). In North America it is usually planted as a monostand with one or more varieties blended for lawns, or mixed with Kentucky Bluegrass (*Poa pratensis* L.) for sports fields and lawns. It is also used at lower latitudes to overseed winter dormant warm-season turfgrass areas. In New Zealand and Australia it is used extensively as both a permanent turf for sports pitches and racecourses, and for winter overseeding of warm-season turf areas (Thorogood 2003).

Terrell (1968, 2007) provides the following description of perennial ryegrass. Plants are a short to long-lived perennial, 3-100 cm tall, with culms that are erect, spreading, decumbent, or rarely prostrate, sometimes rooting at the lower nodes, slender, usually with 2-4 nodes aerial below the spike, glabrous or scaberulous just below the spike. Basal leaf sheaths green, reddish, purplish or in age straw colored, sometimes papery in texture, glabrous; upper leaf sheaths green, glabrous. Leaf blades folded (not rolled) in bud of young shoots; mature blades usually 10-30 cm long, 1-6 mm wide, with ca. 20 veins visible on adaxial surface, glabrous, and abaxial surface of blades are shiny, smooth, glabrous; margins glabrous to scaberulous. Ligules to 2.5 mm long, membranous, apex rounded to truncate or erose, glabrous. Auricles present to 3 mm long, or absent. Spikes are 3-31 cm long, straight or slightly curved, usually ¼ to ½ the height of the plant, bearing 5-37 spikelets. Rachis (or central axis of the inflorescence) is slender, often flexuous, 0.6-2.5 mm in width at nodes; internodes concavo-convex or concavo-angular in cross section, glabrous or scaberulous on angles, with the spikelets lying against the concavities of the rachis. Spikelets are 5-22 mm long, 1-7 mm wide, with 2-10 fertile florets and 0-1 sterile rudimentary florets distally, rachilla 0.7-2 mm long, somewhat flattened; glumes, the lower (first) glume is absent, except in the terminal spikelets; upper (second) glumes 3.5-15 mm long, 0.7-1.5 mm wide, with 3- to 9-veins, ⅓-¾ as long as to slightly exceeding the distal florets and somewhat longer to somewhat shorter than the lowest floret, membranous to indurate; lemmas, of lower and middle florets, 3.5-9 mm long, 0.8-2 mm wide (about 4 to 8 times longer than wide), 3- to 5-veined, glabrous or glabrate, oblong or ovate in shape, rounded on back, the hyaline apices are obtuse, acute, slightly bifid, or erose; awns usually absent, when present, to 8 mm long, attached 0.2-0.7 mm below the apices; paleas shorter than (to 1 mm shorter) to slightly longer than the lemmas, apices acute or obtuse, keels with minute teeth; anthers 2-4.2 mm long, 0.3-0.7 mm wide, yellow or purplish. Caryopses 3-5.5 mm long, 0.7-1.5 mm wide, 3 or more times longer than wide. Chromosome Number 2n=14 or 28 (in some commercial cultivars). However, the production of stolons by perennial ryegrass was not reported by Terrell (1968, 2007). Terrell (1968) commented was that the culms are, "rarely prostrate and sometimes rooting at the lowest nodes."

Stolons are horizontal, aboveground stems that root at the nodes and can produce new plants from their nodes. For example, white clover (*Trifolium repens* L.), strawberries (*Fragariaxananassa* Duchesne), creeping bentgrass (*Agrostis stolonifera* L.), and bermudagrass [*Cynodon dactylon* (L.) Persoon] propagate themselves with stolons. The stoloniferous habit of perennial ryegrass can also sometimes be found in grazed pastures. There are a number of references reporting stoloniferous ryegrass in grazed pastures. The stoloniferous habit in perennial ryegrass was first reported by Sinclair (1826). Lawson (1836) in his work discussing the plants cultivated, or capable of being advantageously cultivated in Great Britain for herbage and forage, listed 10 of the most important varieties of *Lolium perenne* for cultivation for livestock. In his list, he discusses the discovery of a remarkably stoloniferous ryegrass collected from Germany. He found this collection so unique that he described it as a new variety: *L. perenne* var. *stoloniferum*. This stoloniferous variety was described as follows: "It is of early spring growth, pushing out long prostrate stolons or shoots, with an abundance of foliage, so that one plant, by the time the spikes begin to appear, will form a close tuft, extending from two to three feet in diameter; the shoots, however; although lying on the ground, never attempted to strike root until near the end of the season, and even then very sparingly."

More recent publications report the occurrence of a 'stoloniferous' or 'rhizomatous' habit in perennial ryegrass that actually is a pseudo-stoloniferous or pseudo-rhizomatous habit and are not true stolons or rhizomes. From observations of perennial ryegrass in New Zealand pastures, Mitchell (1956) stated that "the vegetative shoots of the plant can, where trampled into the soil and buried, adopt a rhizomatous [pseudo-rhizomatous] habit of growth." Kydd (1966) described the spatial orientation of ryegrass tillers under two stocking rate treatments in Hurley, England. Repeated grazing to ground level induced the formation of horizontal tillers, and in the paddocks grazed hard until late spring and then closed for silage these tillers showed stem elongation and produced buds and adventitious roots at the nodes. Kydd (op. cit.) described these as "true stolons." Edmund (1964) suggested stolon formation would be encouraged under grazing, in ryegrass genotypes that had the ability to elevate nodes, and hence potential tiller sites, from the buried crown and this is probably a factor enabling perennial ryegrass to withstand heavy treading. Further observations on stoloniferous ryegrass in Northern Ireland paddocks were made by Hayes (1971). Simons et al. (1974) demonstrated that aerial tillering was encouraged by an increased height of cutting and straw mulch, and that it differed in extent according to genotype.

Harris et al. (1979) reported finding an underground stoloniferous (i.e., pseudo-rhizomatous) growth habit in old turf where crowns had been buried with soil and thatch. They found dead crowns 3-4 cm below the soil surface and the dead crowns were connected to what they termed 'underground stolons.' These 'underground stolons' were reported to be fragile with only the culm itself remaining, with leaves having decomposed away. This was similar to what Mitchell (1956) reported finding in livestock pastures.

In the above cases, these "stolons" are actually: 1) aerial culms that get trampled or pushed down, and then begin to root a the nodes; or 2) plant crowns that become buried by soil, dung, mulch, earthworm casts, etc., and the with the leaves dying and decomposing leaving only the culm, and rooting at nodes. But, in these instances these cannot be considered true stolons in the technical sense, but would be classified as pseudo-stolons or a pseudo-stoloniferous habit in the first instance and has pseudo-rhizomes in the second instance, since the culms were buried.

Oakley and Evans (1921) categorized the stolons (and rhizomes) of timothy (*Phleum pratense* L.) into two types: determinate- and indeterminate-stolons. A determinate-stolon is an above-ground horizontal stem which roots at the nodes and does not produce aerial shoots indeterminately, but the apical meristem will eventually terminate with an inflorescence (e.g., referred to herein as *Lolium perenne* subsp. *stoloniferum*). An indeterminate-stolon is an above ground stem which roots at the node and from which shoots are produced progressively and this horizontal stem will never terminate with an inflorescence, but apical meristem remains vegetative (e.g., bermudagrass and creeping bentgrass).

Perennial ryegrass is an important species for sports fields. Though perennial ryegrass is one of the most wear tolerant cool-season (temperate) turfgrasses available, the demand for more wear tolerance has increased to due to increased use of sports fields, parks, golf courses, and recreational areas. Improvements in summer wear tolerance have been achieved previously indirectly by increasing shoot density (Thorogood, 2003). Winter wear on European sports pitches has been reduced partly by empirical evaluation of wear-resistant of ryegrass varieties using artificial wear machines with studded rollers and using those varieties most wear-resistant (Canaway, 1981). These were only evaluations performed on finished varieties to determine if some may have some wear tolerance. However, no selections were performed and no new wear-resistant varieties were developed from these studies. Traffic simulation is mainly performed to evaluate the wear-resistant of already released cultivars (e.g., Canaway 1981; Cockerham 1989; Anon 2001) or for athletic field research. The goal in using traffic simulation in athletic field research is to subject turfgrass areas to the conditions experienced by actual playing surfaces (Henderson et al. 2005). This research is used to contribute information on the effects of traffic stress on turfgrasses or playing surfaces (Vanini et al. 2007), not on the development of genetically superior populations of wear-resistant turfgrasses.

The amount of biomass produced before wear commences has been found to be a good indicator of winter wear tolerance (Ellis, 1981). Such material will have an equivalent higher biomass after wear and will also maintain a greater leaf area index with a greater photosynthetic capacity for recovery regrowth. This will be more important in winter when light and temperature may well limit photosynthetic activity.

Lush and Rogers (1992) found that turf follows the general ecological principle of the self-thinning rule, where biomass is inversely proportional to shoot density (White, 1981). This rule states, for a given turf population, there is a ceiling (self-thinning line) where biomass can only be increased with a reduction in shoot density. For example, lowering the cutting height will increase shoot density, while raising the cutting height will increase biomass. The correlation between shoot density and biomass in ryegrass cultivars is weak (Shildrick, 1981), and hence many cultivars listed by the STRI (Sports Turf Research Institute, Bingley, West Yorkshire, UK; which is the independent market leader in consultancy and research for sports surfaces) as having good wear tolerance have poor shoot density and visual appeal (Anon. 2001). The lack of association between wear tolerance and visual appeal (shoot density) was also reported by Bonos et al. (2001).

Currently, little is known or published, about the mechanisms and genetic control of resistance and tolerance on which more directed selection could be practiced (Thorogood 2003). But the inventors have discovered through a novel intense selection protocol involving artificial traffic simulation in the actually breeding process, which not only has improved the wear tolerance and visual appeal of these perennial ryegrasses, but also, unexpectedly, selected for ryegrass genotypes with determinate-stolons that enhance the wear tolerance and have an increased regenerative potential to recover from the traffic event.

SUMMARY

The present disclosure relates to a new perennial ryegrass [*Lolium perenne* L. subsp. *stoloniferum* (C. Lawson) Wipff] with an aggressive determinate-stoloniferous growth habit that has excellent wear tolerance and turf quality, with the ability to quickly repair itself from traffic (high regenerative potential) damage. The determinate-stolons enhance the recovery from wear tolerance. Traditionally, traffic tolerance in grasses is an afterthought in breeding. That is, only after a variety is developed, is it put into a traffic trial to determine its traffic tolerance. In contrast, the disclosed new subspecies of perennial ryegrass was developed by starting with artificial traffic to generate or select a traffic tolerant variety. This new subspecies was discovered after years of intense screening with a modified Brinkman traffic simulator, constant mowing, low maintenance and no supplemental irrigation.

Herein disclosed are perennial ryegrass varieties that produce determinate-stolons which in some examples impart superior traffic tolerance and regeneration (recovery) relative to other known perennial ryegrass varieties. In particular examples, these perennial ryegrass varieties known as breeder's code LpC (*Lolium perenne* subsp. *stoloniferum*), including but not restricted to the following subpopulations/varieties: 06-LpC-10; 06-LpC-13; 06-LpC-14; 06-LpC-9; 06-LpC-2; 06-LpC-12; and 09-LpC-72 which are different from all known varieties of perennial ryegrass plants.

At least 2500 seeds of LpC have been deposited (including at least 2500 seeds of each of 06-LpC-10; 06-LpC-13; 06-LpC-14; 06-LpC-9; 06-LpC-2; 06-LpC-12; and 09-LpC-72) with National Collection of Industrial, Food and Marine Bacteria (NCIMB, Aberdeen, Scotland; NCIMB Deposit Nos. NCIMB 41778 *Lolium perenne* subsp. *stoloniferum* 06-LpC 2; NCIMB 41779 *Lolium perenne* subsp. *stoloniferum* 06-LpC 9; NCIMB 41780 *Lolium perenne* subsp. *stoloniferum* 06-LpC 10; NCIMB 41781 *Lolium perenne* subsp. *stoloniferum* 06-LpC 12; NCIMB 41782 *Lolium perenne* subsp. *stoloniferum* 06-LpC 13; NCIMB 41783 *Lolium perenne* subsp. *stoloniferum* 06-LpC 14; and NCIMB 41784 *Lolium perenne* subsp. *stoloniferum* 09-LpC 72) on Nov. 19, 2010 under the Budapest Treaty. These seeds will be irrevocably and without restriction released to the public upon the issuance of a patent. Therefore, these seeds are known and readily available to the public. In one embodiment, the disclosure provides grass seed deposited as NCIMB Deposit No: NCIMB 41778; NCIMB 41779; NCIMB 41780; NCIMB 41781; NCIMB 41782; NCIMB 41783; and NCIMB 41784, as well as grass seed mixtures containing such seeds.

In one embodiment, the disclosure provides perennial ryegrass plants having or consisting of the morphological and physiological characteristics of LpC, such as perennial ryegrass plants having determinate-stolons, for example 06-LpC-10; 06-LpC-13; 06-LpC-14; 06-LpC-9; 06-LpC-2; 06-LpC-12; or 09-LpC-72. Also disclosed are seeds of such plants, progeny of such plants, and vegetative sprigs or clones of such plants. In another embodiment, the disclosure provides grass plants having the genotype of LpC, for example grass plants having the genotype of 06-LpC-10; 06-LpC-13; 06-LpC-14; 06-LpC-9; 06-LpC-2; 06-LpC-12; or 09-LpC-72.

The disclosure also encompasses perennial ryegrass plants that are produced by crossing a perennial ryegrass having determinate-stolons disclosed herein (e.g., LpC), such as 06-LpC-10; 06-LpC-13; 06-LpC-14; 06-LpC-9; 06-LpC-2; 06-LpC-12; or 09-LpC-72, with other grass varieties, such as other perennial ryegrasses or other grass species (e.g., *Lolium multiflorum, L. rigidum, Festuca pratensis, Festuca* spp., *Lolium* spp., *Schedonorus* spp.). Also disclosed are seeds resulting from such a cross, grass plants grown from such seeds, and vegetative sprigs or clones from such a cross. In one embodiment, the seeds resulting from the cross are part of a seed mixture.

In another embodiment, the disclosure provides a method of producing grass seed, including planting seed from a perennial ryegrass having determinate-stolons disclosed herein (LpC), for example 06-LpC-10; 06-LpC-13; 06-LpC-14; 06-LpC-9; 06-LpC-2; 06-LpC-12; or 09-LpC-72 under conditions that result in the germination of the seed, growth of grass plants and setting of progeny seed, and then harvesting the progeny seed. Also disclosed is grass seed produced by this method, as well as grass seed mixtures including such grass seed.

Also disclosed is a method of producing a grass plant which includes crossing a grass plant produced from a perennial ryegrass having determinate-stolons disclosed herein (e.g., LpC), such as crossing 06-LpC-10; 06-LpC-13; 06-LpC-14; 06-LpC-9; 06-LpC-2; 06-LpC-12, or 09-LpC-72 with at least one other grass plant to produce at least one seed, harvesting the seed, and germinating the seed to produce at least one progeny grass plant. Included in the disclosure are grass plants produced using this method, as well as a vegetative sprig or clone of the grass plant.

The LpC grass plants disclosed herein (such as 06-LpC-10; 06-LpC-13; 06-LpC-14; 06-LpC-9; 06-LpC-2; 06-LpC-12, and 09-LpC-72) can be planted in a variety of areas, for example in areas where turf is desired. Examples include, but are not limited to: golf courses, for example golf course fairways, tee boxes, greens, and roughs; lawns; athletic fields (such as football fields, baseball fields, soccer fields, lacrosse fields, cricket pitches, and tennis courts); parks; pastures (such as areas for animal grazing, for forage, silage, or hay); roadsides; and erosion control areas.

The disclosure also includes sod, which includes a perennial ryegrass having determinate-stolons disclosed herein (LpC, such as 06-LpC-10; 06-LpC-13; 06-LpC-14; 06-LpC-9; 06-LpC-2; 06-LpC-12, and 09-LpC-72). The sod can be planted in any area where grass plants are desired, such as the areas listed above.

In one embodiment, the perennial ryegrass plants having determinate-stolons disclosed herein (LpC, such as 06-LpC-10; 06-LpC-13; 06-LpC-14; 06-LpC-9; 06-LpC-2; 06-LpC-12, and 09-LpC-72) include one or more transgenes.

Methods for selecting a grass plant having determinate-stolons is provided herein. In some examples the method includes exposing a turf plot planted with the grass plant to traffic (such as natural traffic or traffic generated with a simulator) at least once or twice a week from May (or when grasses come out of winter and begin actively growing) until the first frost in the fall. In some examples, the traffic simulator weighs at least 1000 or at least 2000 lbs. The turf plot can be mowed at least once a week to a desired height (for example between 0.5-2 inches). Subsequently, plants comprising determinate-stolons that survive after at least two or at least three years are selected. In another example the traffic simulator is applied only in winter or traffic is applied 12 months out of the year, with or without mowing of plots. Plants generated using such methods are also provided.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee."

FIG. 26 is a schematic drawing of *Lolium perenne* L. subsp. *stoloniferum* 06-LpC-13 with determinate-stolons (right) and peripheral tiller of *Lolium perenne* L. subsp. *perenne* (left).

FIG. 27 is a dendrogram generated from the genetic analysis of several perennial ryegrass varieties, including several of *Lolium perenne* L. subsp. *stoloniferum* subpopulations/varieties.

DETAILED DESCRIPTION

Description of Terms

Figure 1:
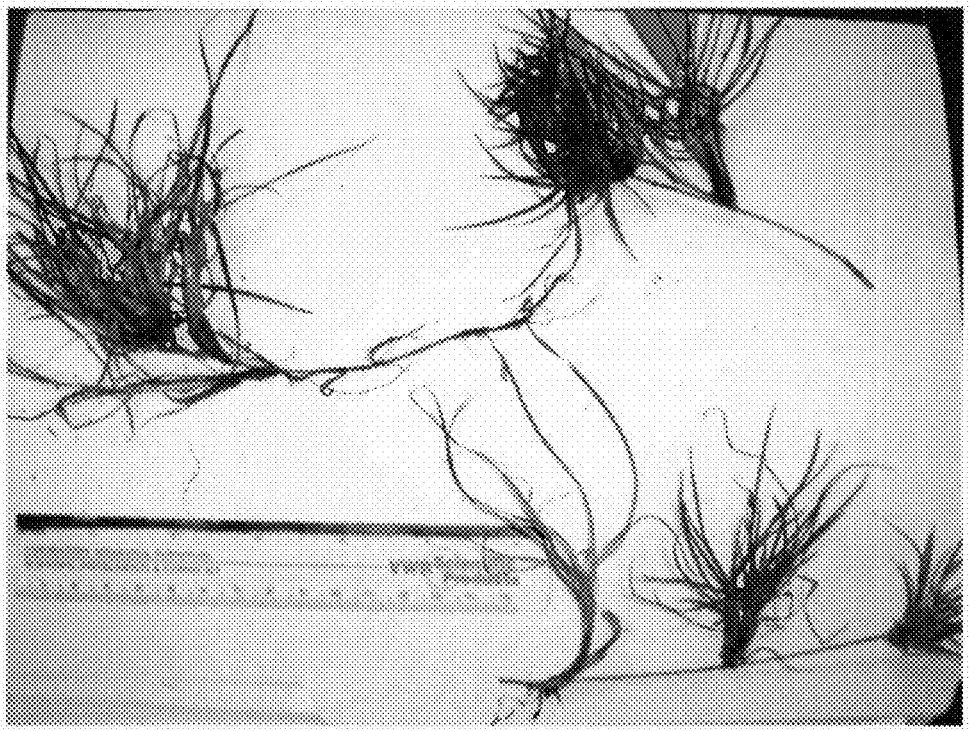
FIGS. 1-5 are digital images showing representative perennial ryegrass plants having determinate-stolons disclosed herein (LpC) showing the determinate-stolons.
Figure 2:
Figure 3:
Figure 4:
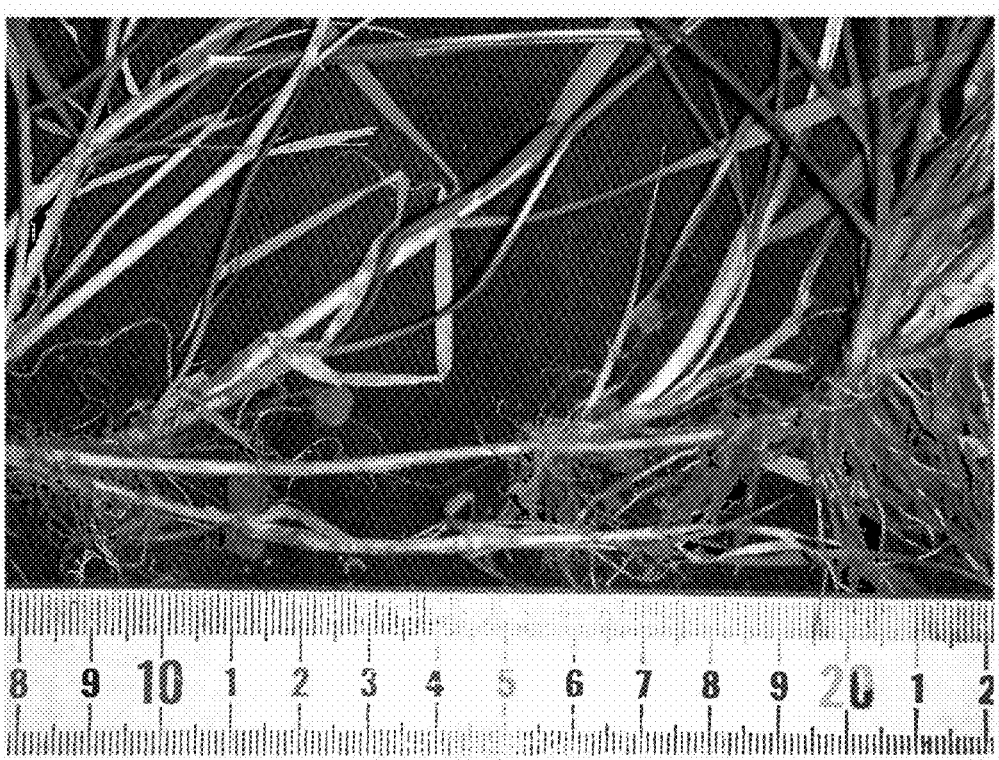
Figure 5:
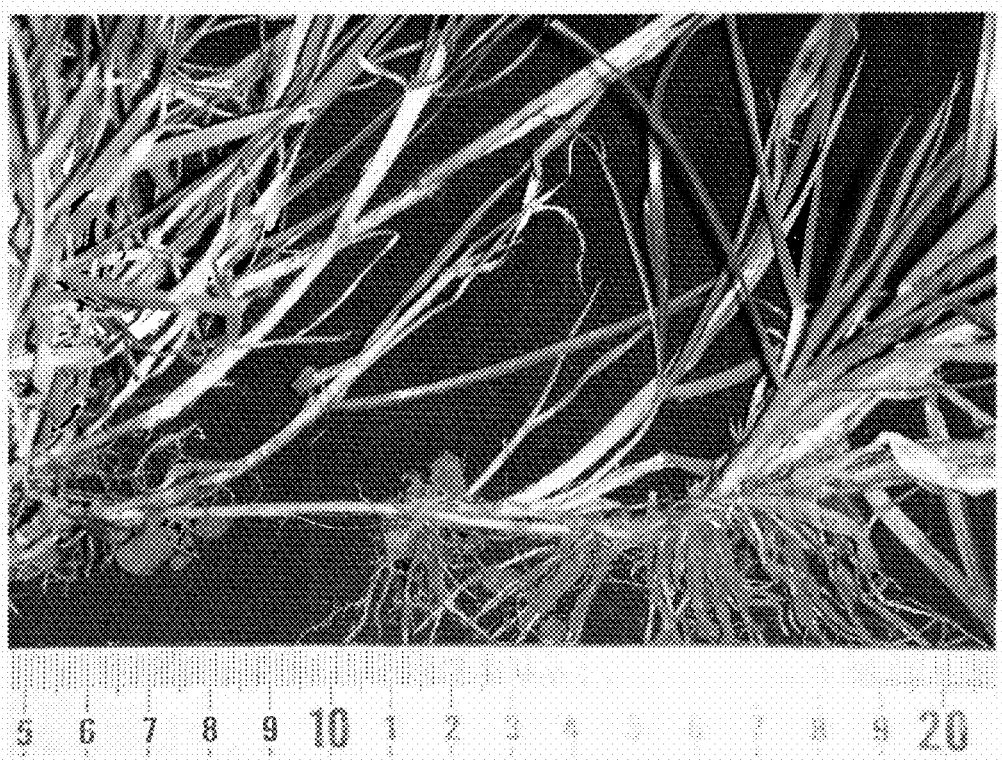
Figure 6:
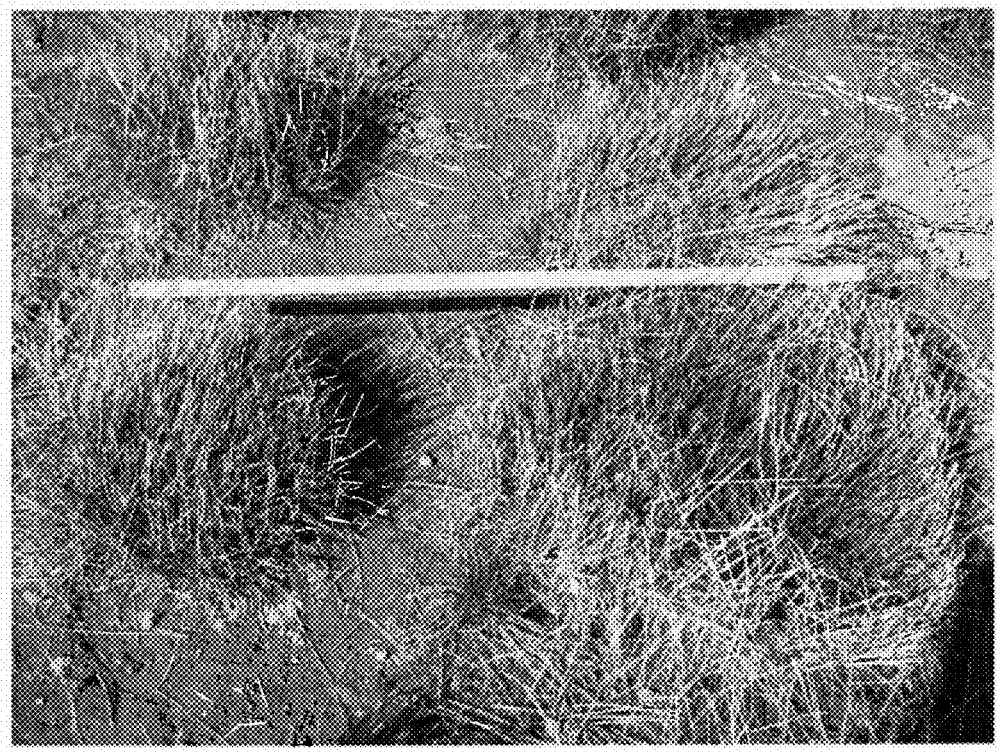
FIG. 6 is a digital image comparing the aggressive spreading habit of a single plant disclosed herein with determinate-stolons (LpC plant on right) to a single plant not possessing determinate-stolons (plant on left).
Figure 7:
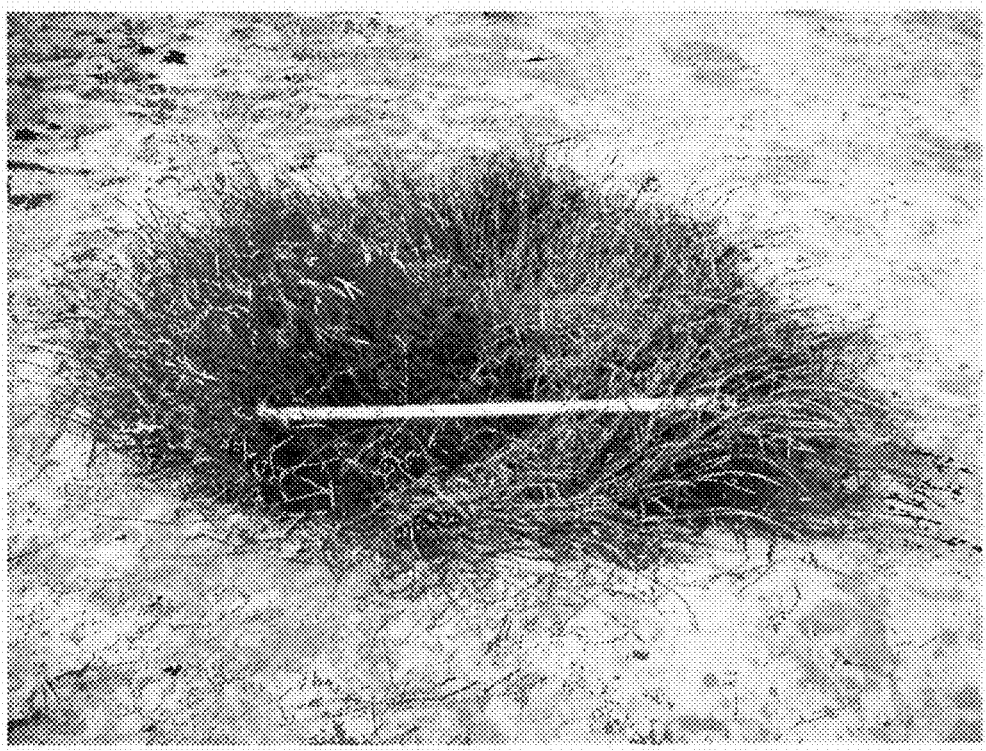
FIGS. 7 and 8 are digital images showing the aggressive spreading habit of a single plant (18 months old) disclosed herein with determinate-stolons (LpC). The ruler is a one meter in length.
Figure 8:
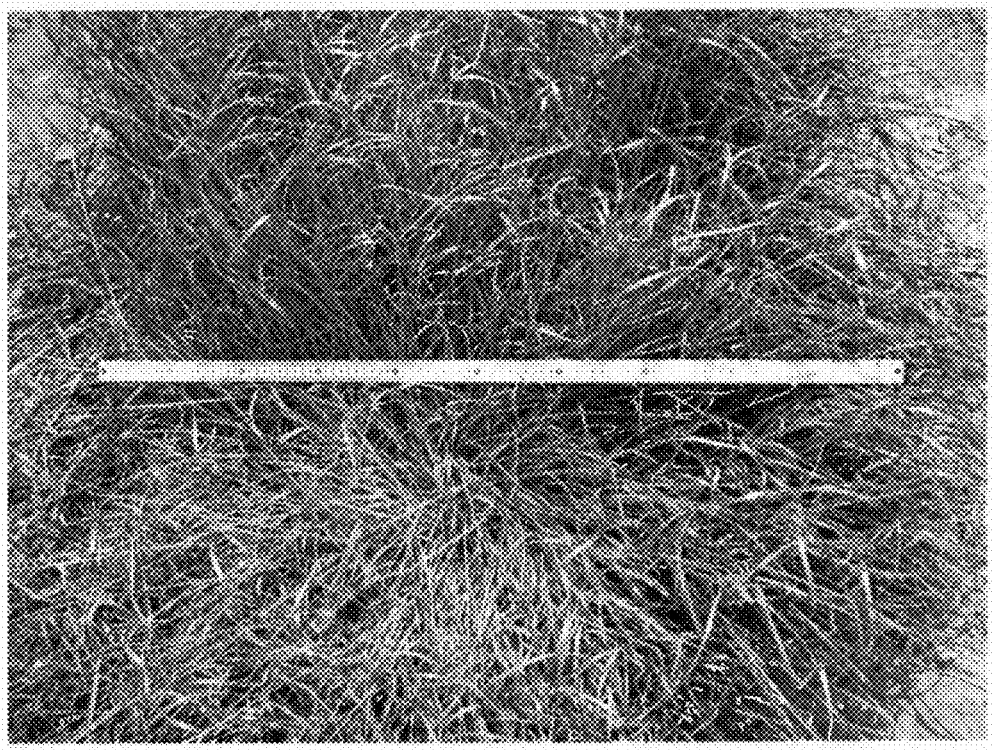
Figure 9:
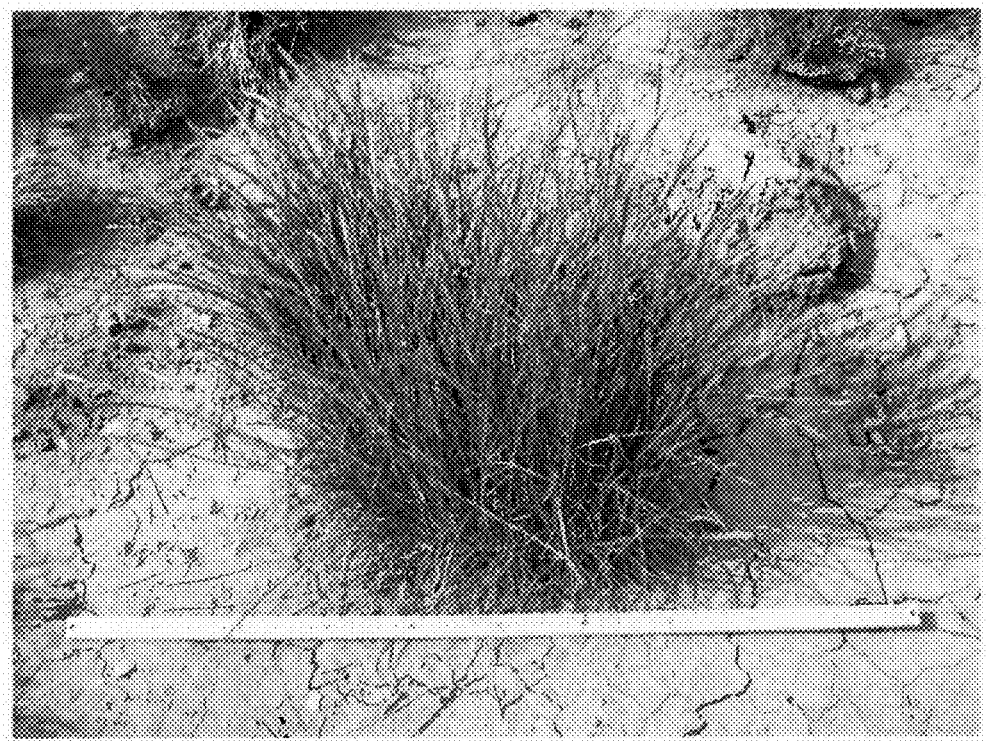
FIG. 9 is a digital image showing the non-aggressive spreading habit of single plant (18 months old) without determinate-stolons. The ruler is a one meter in length.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a seed" includes one or a plurality of such seeds. The term "or" refers to a single element of stated alternative elements or a combination of two or more elements, unless the context clearly indicates otherwise. For example, the phrase "A or B" refers to A, B, or a combination of both A and B.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

Allele. The alternative form of a gene at a locus.

Alter. To increase or decrease, for example to increase or decrease the biological activity of a protein, for example by utilizing up-regulation, down-regulation, or gene silencing.

Artificial Traffic. The result of using traffic simulation to subject grass-covered areas to the conditions experienced by actual playing surfaces. Artificial traffic is produced by artificial traffic simulator machines. These machines are used to create (replicate) the traffic stresses created on grass (such as turfgrass) by natural athletic play. In some examples simulated traffic encompasses one or more of the following parameters: 1.) it should be uniform and reproducible; 2.) the injury to the grass should be similar to natural wear; and 3.) the rate of the artificial, simulated, wear should be accelerated greatly over the natural rate of wear in order to keep the relative number of simulated passes to a minimum.

Backcross. The mating of a hybrid to one of its parents.

Caryopsis. A dry, hard, indehiscent, one-seeded fruit with the thin pericarp adnate to the seed coat; the characteristic grass fruit. This differs from the achene only in the fusion of the pericarp and seed coat.

Coleoptile. The sheath protecting the embryonic shoot, attached at the base of the plumule on the scutellar side of the shoot axis; interpreted by many as the first vegetative leaf of the shoot.

Coleorhiza. The sheath of the monocotyledonous embryo that protects the primary root or radicle.

Cell. Cell as used herein includes a plant cell, whether isolated, in tissue culture or incorporated in a plant or plant part.

Commercial perennial ryegrass. A cultivar of perennial ryegrass that is commercially available, for example consumer and wholesale availability.

Cotyledon. The first leaf of a grass embryo. The grass cotyledon is called the scutellum. It is the first leaf in a grass embryo, attached to the basal node of the mesocotyl, and serving as a food storage organ.

Cross. Synonymous with hybridize or crossbreed. The mating of genetically different individuals.

Crown. The persistent base of herbaceous, perennial grasses. Crown perimeter. A measurement of the distance around the outermost edge encompassing the crown of a grass.

Crown Spread. A measure of the amount of perimeter that occurs each year in a grass plant as compared with the previous years measurements of crown perimeter.

Culm. The erect, noded (jointed), hollow or pithy stem of a grass or sedge. The culm is where the leaves attach and the inflorescences arise and are supported. The culm is comprised of one or more solid joints known as nodes. The nodes are where the leaves are attached and where secondary branches and roots originate. Roots may also develop from a node where the node comes into contact with the ground.

Determinate-Stolon: An above-ground horizontal stem which roots at the nodes along the ground, but the apical meristem will eventually terminate with an inflorescence (e.g., *Lolium perenne* subsp. *stoloniferum*). The apical meristem of the determinate-stolon does not grow indeterminately (as do the stolons of bermudagrass or creeping bentgrass); they eventually terminate in an inflorescence.

Embryo. The incipient plantlet in a seed.

Endophyte. An endosymbiont fungus that lives within a plant without causing apparent disease. Many economically turfgrasses (e.g., *Festuca* spp., *Lolium* spp.) carry fungal endophytes (*Neotyphodium* spp.) which may improve the ability of these grasses to tolerate abiotic stresses such as drought, as well as improve their resistance to insect and mammalian herbivores.

Forage. Plant material (mainly plant leaves and stems) eaten by grazing livestock. Historically the term forage has meant only plants eaten by the animals directly as pasture, crop residue, or immature cereal crops, but it is also used more loosely to include similar plants cut for fodder and carried to the animals, especially as hay or silage.

Floret. As applies to grasses, the lemma and palea with the enclosed flower.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Grass flower. The grass flower is comprised of 2 or 3 lodicules (reduced perianth structures) with either: 1) both pistil and stamen(s); 2) a pistil only; or 3) stamen (s) only. The grass flower is terminal on a short axis developed in the axil of the lemma. Immediately below the flower on the same short axis is the palea, which together with the lemma encloses the flower.

Grass inflorescence. The flowering portion of a grass shoot; the spikelets and the axis or branch system that supports them. The inflorescence is delimited at the base by the uppermost leafy node of the shoot.

Hybrid. The progeny of the mating between genetically different parents.

Indeterminate-Stolon. An above ground stem which roots at the node and from which shoots are produced progressively and this horizontal stem will not ever terminate with an inflorescence, but apical meristem remains vegetative (e.g., bermudagrass and creeping bentrgrass).

Internode. The portion of the stem or other structure between two nodes.

Intercalary meristem. An actively growing primary tissue region somewhat removed from the apical meristem; intercalary meristems are present at the base of the internodes in young grass shoots.

Interspecific hybrid. Hybrids that result from the mating two species.

Lemma. The lowermost of the two bracts enclosing the flower in the grass floret.

Linkage. Genetic linkage occurs when particular genetic loci or alleles for genes are inherited jointly. Genetic loci on the same chromosome are physically connected and tend to stay together during meiosis, and are thus genetically linked. This is called autosomal linkage. Alleles for genes on different chromosomes are usually not linked, due to independent assortment of chromosomes during meiosis.

Linkage disequilibrium. The occurrence in a population of certain combinations of linked alleles in greater proportion than expected from the allele frequencies at the loci.

Mesocotyl. The internode between the scutellar node and the coleoptile in the embryo and seedling of a grass.

Mowing. The act or process of mechanically removing the growth of grass by cutting it, for example with sharp steel blades (rotary or reel) to maintain a specific height of growth. In specific examples, mowing grass plants is not simply passing a mower over the grass but can involve maintaining sharp cutting blades, setting the blade to the correct height and cutting the grass at regular intervals to maintain a healthy population of grass plants.

Node. The point on a stem where a leaf is attached or has been attached; a joint. If is a solid point in the grass culm at which the intercalary meristem is located. The node also contains the bud that is capable of producing a new shoot. The terminal node contains the bud that produces the inflorescence.

Palea. The uppermost of the two bracts enclosing the grass flower in the floret.

Percent Identity. As used herein refers to the comparison of the homozygous alleles of two perennial ryegrass varieties.

Percent identity is determined by comparing a statistically significant number of the homozygous alleles of two developed varieties. For example, a percent identity of 90% between perennial ryegrass variety 1 and perennial ryegrass variety 2 means that the two varieties have the same allele at 90% of their loci.

Percent Similarity. As used herein refers to the comparison of the homozygous alleles of one perennial ryegrass variety with another ryegrass plant, and if the homozygous allele of the first ryegrass matches at least one of the alleles from the other plant then they are scored as similar. Percent similarity is determined by comparing a statistically significant number of loci and recording the number of loci with similar alleles as a percentage. A percent similarity of 90% between the first ryegrass and another plant means that the first ryegrass matches at least one of the alleles of the other plant at 90% of the loci.

Perimeter: The continuous line forming the boundary of a closed geometric figure or shape, and the length of such a line.

Peripheral Stems or Culms: Relating to or being the culms at surface or outer part of plant. These are the culms closest to surface of the soil.

Plant. Includes reference to an immature or mature whole plant, including a plant from which seed, roots or leaves have been removed. Seed or embryo that will produce the plant is also considered to be the plant.

Plant height. Plant height is taken from the top of the soil to the tip of the inflorescence, and is measured in centimeters.

Plant parts. Includes protoplasts, leaves, stems, roots, root tips, anthers, pistils, seed, embryo, pollen, ovules, cotyledon, hypocotyl, flower, shoot, tissue, petiole, cells, meristematic cells and the like.

Primary tillers. Primary tillers are shoots arising at the crown.

Progeny. Offspring; descendants.

Quantitative Trait Loci (QTL). Though not necessarily genes themselves, quantitative trait loci (QTLs) are stretches of DNA that are closely linked to the genes that underlie the trait in question. QTLs can be molecularly identified (for example, with AFLP) to help map regions of the genome that contain genes involved in specifying a quantitative trait. This can be an early step in identifying and sequencing these genes. Inheritance of quantitative traits or polygenic inheritance refers to the inheritance of a phenotypic characteristic that varies in degree and can be attributed to the interactions between two or more genes and their environment.

Regeneration. The development of a plant from tissue culture. The cells may, or may not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Rhizome. A modified, underground, stem with scales (reduced leaves) at the nodes and producing leafy shoots on the upper side and roots on the lower side.

Secondary tillers. The shoots arising from the nodes of the primary tillers.

Seed. The part of a flowering plant that typically contains the embryo with its protective coat and stored food and that can develop into a new plant under the proper conditions; fertilized and mature ovule. In perennial ryegrass, the 'seed' consists of the caryopsis, and the lemma and palea.

Shoots. The aerial portion of a plant body, consisting of stems, leaves, and flowers.

Sod. Sod, or turf, is grass and the part of the soil beneath it held together by the roots, or a piece of thin material. The term sod may be used to mean turf grown and cut specifically for the establishment of lawns.

Space Plant. A single plant that originates from one seed of a population/variety, which are then planted into a nursery in which they are spaced far enough part so that they will not grow together. This way the individual plants retain their individual identity and their identity in the nursery is always known.

Stolon. A modified horizontal stem that runs along the surface of the ground and serves to spread the plant by rooting on lower side of the nodes and forming shoots on the upper side on the node. The formation of stolons allow the turf to repair itself from injury and to spread. Stolons can be classified as either determinate or indeterminate.

Tensile strength. The amount of force in pounds required to tear a piece of sod in two. Tensile strength is determined with a mechanical sod stretcher coupled to a device to measure force in pounds. Tensile strength, tear point and sod strength are used interchangeably.

Tiller. A subterranean or ground-level lateral shoot, usually erect, as contrasted with horizontally spreading rhizomes and stolons.

Transformation. The introduction of new genetic material (e.g., exogenous transgenes) into nonbacterial cells including animal and plant cells. Exemplary mechanisms that are available (but not limited to) to transfer DNA into plant cells include Agrobacterium mediated transformation. Briefly, plant tissue (often leaves) is cut into small pieces, e.g. 10 mm×10 mm, and soaked for 10 minutes in a fluid containing suspended Agrobacterium. Some cells along the cut will be transformed by the bacterium, which inserts its DNA into the cell, which is placed on selectable rooting and shooting media, allowing the plants to regrow. Some plants species can be transformed just by dipping the flowers into suspension of Agrobacterium and then planting the seeds in a selective medium. Particle bombardment: Particles of gold or tungsten are coated with DNA and then shot into young plant cells or plant embryos. Some genetic material will stay in the cells and transform them. This method also allows transformation of plant plastids. The transformation efficiency is lower than in agribacterial mediated transformation, but most plants can be transformed with this method. Electroporation: make transient holes in cell membranes using electric shock; this allows DNA to enter as described above for Agrobacterium. Another exemplary method is viral transformation (transduction), by packaging the desired genetic material into a suitable plant virus and allowing this modified virus to infect the plant. If the genetic material is DNA, it can recombine with the chromosomes to produce transformant cells. However genomes of most plant viruses consist of single stranded RNA which replicates in the cytoplasm of infected cell. For such genomes, this method is a form of transfection and not a real transformation, since the inserted genes never reach the nucleus of the cell and do not integrate into the host genome. The progeny of the infected plants is virus free and also free of the inserted gene.

Transgene. A gene or genetic material that has been transferred naturally, or by a genetic engineering technique, from one organism to another. In one example, describes a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In general, the DNA is incorporated into the organism's germ line. Transgene can also describe any DNA sequence, regardless of whether it contains a gene coding sequence or it has been artificially constructed, which has been introduced into an organism or vector construct in which it was previously not found. A transgene can be either a cDNA (complementary DNA) segment, which is a copy of mRNA (messenger RNA), or the gene itself residing in its original region of genomic DNA.

Turf. An area of grass maintained for decorative or recreational use.

Variety. Used interchangeably with the term 'cultivar' to denote a group of individuals that are distinct genetically from other groups of individuals in the species.

Vernalization. The process by which floral induction in some plants is promoted by exposing the plants to chilling for a certain duration. The acquisition of a plant's ability to flower or germinate in the spring by exposure to the prolonged cold of winter.

Perennial Ryegrass Plants Having Determinate-Stolons

The present disclosure provides a new subspecies of perennial ryegrass [*Lolium perenne* L. subsp. *stoloniferum* (C. Lawson) Wipff]. The new subspecies has an aggressive determinate-stoloniferous growth habit that has excellent wear tolerance and turf quality, with the ability to quickly repair itself from traffic damage (high regeneration potential). In particular examples, the present disclosure provides a perennial ryegrass plant that has determinate-stolons referred to herein as LpC, and includes the following populations: 06-LpC-10; 06-LpC-13; 06-LpC-14; 06-LpC-9; 06-LpC-2; 06-LpC-12; and 09-LpC-72, wherein representative seed has been deposited under NCIMB Deposit Nos. NCIMB 41778; NCIMB 41779; NCIMB 41780; NCIMB 41781; NCIMB 41782; NCIMB 41783; and NCIMB 41784. Such LpC plants also have excellent wear tolerance, turf quality, and the ability to quickly repair (high regeneration potential) itself from traffic damage.

The disclosed perennial ryegrass plants having determinate-stolons (LpC), as well as excellent wear tolerance, turf quality, and the ability to quickly repair (high regeneration potential) itself from traffic damage, such as 06-LpC-10; 06-LpC-13; 06-LpC-14; 06-LpC-9; 06-LpC-2; 06-LpC-12; and 09-LpC-72, can have one or more of the following phenotypes provided below.

For example, the disclosed perennial ryegrass plants, when grown as individual plants, can reach a greater crown spread perimeter than other known perennial grasses, such as Pinnacle II (Barenbrug, USA), when mowed (e.g., using a lawnmower) to maintain a height of 1 inch, 1.5 inches, or 2 inches. In certain examples, the disclosed perennial ryegrass plants when grown as individual plants reach a crown spread perimeter of at least 80 cm after mowing and two and half years of growth (e.g., maintenance of a height of about 2 inches), for example as compared to Pinnacle II, which only reached a crown spread perimeter of about 72 cm-73 cm. For example, the disclosed perennial ryegrass plants, when grown as individual plants, can reach a crown spread perimeter of 80 cm to 100 cm (such as 80 cm to 98 cm, or 81 cm to 98 cm) after mowing and two years of growth (e.g., maintenance of a height of 2 inches). If the plants are also exposed to artificial traffic (for example with two passes once a week from May to October) the disclosed perennial ryegrass plants when grown as individual plants can reach a crown spread perimeter of at least 56 cm (such as at least 57 cm, at least 58 cm, at least 60 cm or even at least 65 cm, for example 58 or 57 cm to 71 cm) after mowing, artificial traffic and 1 year of growth, (as compared to only about 54 cm for Pinnacle II), or a crown spread perimeter of at least 65 cm (such as at least 69 cm, at least 70 cm, at least 80 cm or even at least 85 cm, such as 69 cm to 94 cm) after 2 years of growth, mowing, and artificial traffic, as compared to only about 59 cm for Pinnacle II. For example, the disclosed plants when also exposed to artificial traffic with two passes once a week from May to October and when grown as individual plants, can reach a crown spread perimeter of 55 cm to 70 cm (such as 57 cm to 71 cm or 57 to 68 cm) after mowing, artificial traffic, and 1 year of growth, or a crown spread perimeter of 69 cm to 100 cm (such as 69 cm to 94 cm or 70 to 93 cm) after mowing, artificial traffic and 2 years of growth.

In some examples, the perennial ryegrass plants disclosed herein, when grown in a row, can reach a greater crown spread than other known perennial grasses, such as Pinnacle II, when mowed (e.g., using a lawnmower) to maintain a height of 1 inch, 1.5 inches, or two inches. In certain examples, the disclosed perennial ryegrass plants, when grown in a row, can reach a crown spread of at least 23 cm (such as at least 24 cm, at least 25 cm, or at least 26 cm) after mowing and two years of growth (e.g., maintenance of a height of 2 inches), for example as compared to Pinnacle II, which only reached a crown spread perimeter of about 20 cm. For example, the disclosed perennial ryegrass plants, when grown in a row, can reach a crown spread of about 23 cm to 26 cm (such as 23.5 cm to 25.8 cm) after mowing and two years of growth (e.g., maintenance of a height of 2 inches).

If the plants are also exposed to artificial traffic with two passes once a week from May to October the disclosed perennial ryegrass plants when grown in a row can reach a crown spread of at least 13 cm (such as at least 14 cm, at least 15 cm, or even at least 16 cm) after mowing, artificial traffic, and 1 year of growth (as compared to only about 10 cm to 11 cm for Pinnacle II), or reach a crown spread of at least 19 cm (such as at least 20 cm, at least 22 cm, or even at least 24 cm) after mowing, artificial traffic, and 2 years of growth (as compared to only about 17 cm for Pinnacle II). For example, the plants when also exposed to artificial traffic with two passes once a week from May to October and when grown in a row reach a crown spread of 13 cm to 17 cm (such as 14 cm to 17 cm or 13 to 16 cm) after mowing, artificial traffic, and 1 year of growth, or reach a crown spread of 19 cm to 25 cm (such as 20 cm to 25 cm or 20 to 24 cm) after mowing, artificial traffic, and 2 years of growth.

In some examples, the disclosed perennial ryegrass plants when grown in a turf plot were exposed to traffic simulation with a SISIS® wear machine developed by SISIS and STRI (Sports Turf Research Institute, Bingley, UK). The machine is equipped with cleats on weighted rollers that have a differential slip and cause cleat damage and tearing of the grass. Two passes with the SISIS cause similar damage to damage caused during one football game. Each season, traffic was applied weekly to simulate 5 games per week, for example between May and August or May and November and mowed (e.g., using a lawnmower) to maintain a height of 1 inch (walk behind reel mower), 1.5 inches, and 2 inches with a walk behind rotary mower) produce determinate-stolons, whereas the other known perennial grasses, such as Pinnacle II, Premier II, Barlennium, and Turfstar produced no stolons. For example, when grown under such conditions, the disclosed perennial ryegrass turf plots can have at least 3% of the plants producing determinate-stolons, such as at least 3% when maintained at a 1 inch or 1.5 inch mowing height, or at least 6% when maintained at a 2 inch mowing height. In some examples, at least 4%, at least 5%, at least 6%, at least 7%, at least 8%, at least 9%, at least 10%, at least 11%, at least 12%, at least 13%, at least 14%, at least 15%, or more of the plants produce determinate-stolons when grown in a turf plot, and mowed to a height of 1 to 2 inches, and in some examples also exposed to traffic simulation.

Mowing is the act or process of mechanically removing the growth of grass by cutting it, for example with sharp steel blades (rotary or reel) to maintain a specific height of growth. In specific examples, mowing grass plants is not simply passing a mower over the grass but can involve maintaining sharp cutting blades, setting the blade to the correct height and cutting the grass at regular intervals to maintain a healthy population of grass plants. In a specific example, turf grasses are mowed down by a rotary style mower which cuts the grass at two inches of height, for example during the growing season for grass usually April-November about twice per week.

Artificial traffic includes using traffic simulation to subject grass areas (such as a turfgrass) to the conditions experienced by actual playing surfaces. Artificial traffic can be produced by artificial traffic simulator machines. These machines are used to create (replicate) the traffic stresses created on grass by natural athletic play. In particular examples, artificial traffic encompasses one or more of the following parameters: 1.) it should be uniform and reproducible; 2.) the injury to the grass should be similar to natural wear; and 3.) the rate of the artificial, simulated, wear should be accelerated greatly over the natural rate of wear in order to keep the relative number of simulated passes to a minimum.

In some examples, the disclosed perennial ryegrass plants demonstrate regenerative abilities, for example as shown by recovery of the plants when grown as a space plant and exposed to traffic simulation with a SISIS® wear. Traffic was applied weekly to simulate 5 games per week, for example between May and August and mowed (e.g., using a lawnmower) to maintain a height of 1.5 inches to produce determinate-stolons. For example, when grown under such conditions, the disclosed perennial ryegrass space plants can have at least 3%, at least 5%, at least 8%, at least 10%, or at least 15% of the plants producing determinate-stolons (e.g., when maintained at a 1, 1.5 or 2 inch mowing height), such as at least 3% when maintained at a 1.5 inch mowing height with 50% of the cover removed with an artificial traffic simulator, whereas the other known perennial grasses, such as Pinnacle II, Premier II, Barlennium, and Turfstar produced no stolons. In some examples, at least 4%, at least 5%, at least 6%, at least 7%, at least 8%, at least 9%, at least 10%, at least 11%, at least 12%, at least 13%, at least 14%, at least 15%, or more of the plants produce determinate-stolons when grown as space plants, and mowed to a height of 1 to 2 inches (e.g., when maintained at a 1, 1.5 or 2 inch mowing height), and in some examples also exposed to traffic simulation. If the plants are mowed and also exposed to artificial traffic with 2-3 passes once a week from May to August with the modified Brinkman traffic simulator to simulate the amount of traffic received from 5 games per week; the disclosed perennial ryegrass plants when grown as a space plant can reach a crown circumference of at least 77 cm (such as at least 80 cm, at least 84 cm, at least 88 cm, or even at least 105 cm) after mowing, artificial traffic, and at least 12 months of growth (as compared to only about 50 cm for Pinnacle II. In addition example, such plants also have a higher regeneration potential than other perennial ryegrasses. That is, when also exposed to mowing and artificial traffic with 2-3 passes once a week from May to August with the modified Brinkman traffic simulator to simulate the amount of traffic received from 5 games per week, the disclosed plants have an increase in the surface area and crown perimeter over that time frame, as compared to other perennial ryegrasses such as Pinnacle II which have a decrease in the surface area over that time frame. For example, the disclosed plants can have an increase in their crown perimeter of at least 3 cm (such as at least 4, at least 5, at least 7, at least 8, at least 9 or at least 10 cm, such as 3 to 11 cm) within at least two months after artificial traffic has stopped. If the plants are mowed and also exposed to artificial traffic with 2-3 passes once a week from May to August with the modified Brinkman traffic simulator to simulate the amount of traffic received from 5 games per week, the disclosed perennial ryegrass plants when grown as a space plant can reach a surface area of at least 275 cm$^2$ (such as at least 300 cm$^2$, at least 330 cm$^2$, at least 400 cm$^2$, at least 500 cm$^2$, or even at least 600 cm$^2$) after mowing, artificial traffic, and at least 12 months of growth (as compared to only about 210 cm$^2$ for Pinnacle II. In addition example, such plants also have a higher regeneration potential than other perennial ryegrasses. That is, when also exposed to mowing and artificial traffic with 2-3 passes once a week from May to August with the modified Brinkman traffic simulator to simulate the amount of traffic received from 5 games per week, the disclosed plants have an increase in the surface area over that time frame, as compared to other perennial ryegrasses such as Pinnacle II which have a decrease in the surface area over that time frame. For example, the disclosed plants can have an increase in their surface area of at least 2 cm$^2$ (such as at least 8, at least 10, at least 20, at least 30, at least 50, at least 80, at least 90, or at least 100 cm$^2$, such as 2 to 105 cm$^2$) within at least two months after artificial traffic has stopped.

In some examples, the disclosed perennial ryegrass plants when grown as a turf plot, and mowed (e.g., using a lawnmower) to maintain a height of 1.5 inches, produce fewer tillers than Natural Knit, such as fewer multiple branched tillers, tillers in multiple branches, secondary tillers and total number of tillers. For example, the disclosed LpC plants that are at least one year old and mowed regularly have no more than 100 multiple branched tillers (such as no more than 90, no more than 80, no more than 70, no more than 65, no more than 60, or no more than 55, such as 50 to 70 multiple branched tillers), no more than 200 tillers in multiple branches (such as no more than 175, no more than 160, or no more than 155, such as 150 to 100 tillers in multiple branches), no more than 40 secondary tillers (such as no more than 40, no more than 30, or no more than 20, such as 15 to 40 secondary tillers), no more than 400 total number of tillers (such as no more than 450, no more than 400, no more than 380, or even no more than 360 total number of tillers, such as 300 to 400 or 320 to 380 total tillers), or combinations thereof.

In some examples, the disclosed perennial ryegrass plants when grown as a turf plot, and mowed (e.g., using a lawnmower) to maintain a height of 1.5 inches produce fewer tillers than Natural Knit, but have significantly more secondary tiller branches and more secondary branches per tiller than both 'Barclay' and 'Pinnacle II', after two and three years of growth. For example, the disclosed LpC plants that are at least two years old and mowed regularly have at least 340 tillers in a 4 inch diameter (such as at least 340 or at least 360 tillers in a 4 inch diameter, such as 345 to 380 tillers in a 4 inch diameter), have at least 400 tillers per 100 cm$^2$ (such as at least 420, at least 430, at least 440, or at least 450 tillers per 100 cm$^2$, such as 430 to 460 tillers per 100 cm$^2$), at least 20 total secondary tiller branches (such as at least 25, at least 30, or at least 40 total secondary tiller branches, such as 20 to 50 total secondary tiller branches), at least 0.06 secondary branches per tiller (such as at least 0.07, at least 0.08, at least 0.09, at least 0.1, or at least 0.12 secondary branches per tiller, such as 0.06 to 0.15 secondary branches per tiller), or combinations thereof. In another example, the disclosed LpC plants that are at least three years old and mowed regularly have at least 250 tillers in a 4 inch diameter (such as at least 300 or at least 365 tillers in a 4 inch diameter, such as 260 to 360 tillers in a 4 inch diameter), have at least 300 tillers per 100 cm$^2$ (such as at least 330, at least 375, at least 400, or at least 430 tillers per 100 cm$^2$, such as 300 to 450 tillers per 100 cm$^2$), at least 20 total secondary tiller branches (such as at least 25, at least 30, at least 40 or at least 60 total secondary tiller branches, such as 20 to 70 total secondary tiller branches), at least 0.08 secondary branches per tiller (such as at least 0.09, at least 0.1, at least 0.13, at least 0.15, or at least 1.7 secondary branches per tiller, such as 0.8 to 0.2 secondary branches per tiller), or combinations thereof.

In some examples, the disclosed perennial ryegrass plants when grown as a space plant, mowed (e.g., using a lawnmower) to maintain a height of about 2 inches, and subjected to traffic simulation with 2-3 passes once a week from May to August with the modified Brinkman traffic simulator to simulate the amount of traffic received from 5 games per week), produce more peripheral (outside) tillers; more outside determinate-stolons (than Pinnacle II's outside peripheral tiller number); a higher total number of rooting nodes; and more secondary tillers on determinate-stolons than the secondary tillers on Pinnacle II's peripheral tillers, after about 1 year of growth. In addition, 06LpC varieties had a longer total determinate-stolon length, and the length of the longest determinate-stolon was longer than Pinnacle II's peripheral tillers, after about 1 year of growth. For example, the disclosed LpC plants that are at least one year old, mowed regularly (e.g., to a height of about 2 inches) and exposed to traffic simulation, have at least 20 peripheral (outside) tillers (such as at least 25, at least 30, at least 32, or at least 37 peripheral tillers, such as 20 to 40 peripheral tillers); at least 200 total rooting nodes (such as at least 220, at least 240, at least 250, at least 300, at least 500, or at least 600 total rooting nodes, such as 200 to 700 total rooting nodes); at least 15 determinate-stolons (such as at least 16, at least 18, at least 20, at least 25, or at least 32 determinate-stolons such as 15 to 40 determinate-stolons); at least 70 secondary tillers on determinate-stolons (such as at least 80, at least 90, at least 100, at least 120, at least 150, or at least 200 secondary tillers on determinate-stolons, such as 70 to 300 or 70 to 250 secondary tillers with rooting nodes); a total determinate-stolon length of at least 800 mm (such as at least 850, at least 1000, at least 1100, or at least 1300 mm, such as 800 to 1500 mm); a longest determinate-stolon having a length of at least 100 mm (such as at least 120, at least 130, at least 150, at least 160, at least 170, or at least 180 mm, such as 100 to 200 or 100 to 190 mm), or combinations thereof, after about 1 year of growth.

The perennial ryegrass plants disclosed herein can include or consist of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784. For example, such plants have a determinate-stoloniferous growth habit that has excellent wear tolerance and turf quality, with the ability to quickly repair itself (high regeneration potential) from traffic damage.

The disclosure also encompasses progeny of the perennial ryegrass plants provided herein (e.g., progeny of LpC) that have a determinate-stoloniferous growth habit. Such progeny can include or consist of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784. For example, progeny can include a perennial ryegrass plant produced from the perennial ryegrass plants provided herein (such as 06-LpC-10; 06-LpC-13; 06-LpC-14; 06-LpC-9; 06-LpC-2; 06-LpC-12, and 09-LpC-72) by transformation with a transgene that confers upon the perennial ryegrass plant a desired trait, such as resistance to an herbicide, resistance to an insect, resistance to a bacterial disease, resistance to a viral disease, resistance to a fungal disease, resistance to a nematode, drought tolerance, heat tolerance, or salt tolerance. In another example, such progeny include perennial ryegrass plants produced from a cross from a perennial ryegrass plant provided herein (LpC, such as 06-LpC-10; 06-LpC-13; 06-LpC-14; 06-LpC-9; 06-LpC-2; 06-LpC-12, and 09-LpC-72) and another perennial ryegrass plant or other grass species.

The disclosed perennial ryegrass plants (LpC, such as 06-LpC-10; 06-LpC-13; 06-LpC-14; 06-LpC-9; 06-LpC-2; 06-LpC-12, and 09-LpC-72), including progeny of such plants (such as crosses involving the disclosed plants or transgenic plants generated from the disclosed plants as well as plants grown from the seed of such progeny), can be part of sod or turf. For example, the disclosed perennial ryegrass plants (or their progeny or transgenic plants derived from the disclosed plants) can be planted in a golf course fairway, a golf course rough, lawn, athletic field, roadside, or park.

The disclosure also encompasses seed of the perennial ryegrass plants provided herein (LpC, 06-LpC-10; 06-LpC-13; 06-LpC-14; 06-LpC-9; 06-LpC-2; 06-LpC-12, and 09-LpC-72) (as well as seed from progeny of the disclosed plants, such as crosses involving the disclosed plants or transgenic plants generated from the disclosed plants), wherein the seed produces a perennial ryegrass plant, interspecific hybrid, or intergeneric hybrid having or consisting of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784 (such as a determinate-stoloniferous growth habit). In some examples, seed of the perennial ryegrass plants provided herein (such as seed deposited under NCIMB Deposit No. NCIMB 41778; NCIMB 41779; NCIMB 41780; NCIMB 41781; NCIMB 41782; NCIMB 41783; or NCIMB 41784), as well as progeny seed, is part of a seed mixture, such as a mixture of perennial ryegrass seeds and other grass species. In one example the grass seed mixture includes seeds of 06-LpC-10 (NCIMB Deposit No. NCIMB 41778), 06-LpC-13 (NCIMB Deposit No. NCIMB 41779), 06-LpC 14 (NCIMB Deposit No. NCIMB 41780), or combinations thereof, such as a mixture containing 06-LpC-10, 06-LpC-13 and 06LpC 14 (NCIMB Deposit Nos. NCIMB 41778, 41779, and 41780) or a mixture containing 06-LpC-10 and 06-LpC-13 (NCIMB Deposit Nos. NCIMB 41778 and 41779).

Methods of producing an interspecific hybrid perennial ryegrass plant of the present disclosure (LpC, such as 06-LpC-10; 06-LpC-13; 06-LpC-14; 06-LpC-9; 06-LpC-2; 06-LpC-12, and 09-LpC-72) are also provided. In one example, the method can include growing a perennial ryegrass plant provided herein (such as a plant grown from seed deposited under NCIMB Deposit No. NCIMB 41778; NCIMB 41779; NCIMB 41780; NCIMB 41781; NCIMB 41782; NCIMB 41783; NCIMB 41784). Such resulting grass plants are encompassed by this disclosure. In another example, the method can include crossing a perennial ryegrass plant provided herein (such as a plant grown from seed deposited under NCIMB Deposit No. NCIMB 41778; NCIMB 41779; NCIMB 41780; NCIMB 41781; NCIMB 41782; NCIMB 41783; or NCIMB 41784) with at least one other species of ryegrass (*Lolium* sp.) plant to produce at least one interspecific hybrid seed, harvesting the seed, and germinating the seed to produce at least one progeny interspecific hybrid perennial ryegrass plant. Such progeny plants are encompassed by this disclosure, and in some example, have or consist of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784.

Methods of producing an intergeneric perennial ryegrass hybrid plant of the present disclosure (LpC, such as 06-LpC-10; 06-LpC-13; 06-LpC-14; 06-LpC-9; 06-LpC-2; 06-LpC-12, and 09-LpC-72) are also provided. In one example, the method can include growing a perennial ryegrass plant provided herein (such as a plant grown from seed deposited under NCIMB Deposit No. NCIMB 41778; NCIMB 41779; NCIMB 41780; NCIMB 41781; NCIMB 41782; NCIMB 41783; NCIMB 41784). Such resulting intergeneric hybrid grass plants are encompassed by this disclosure. In another example, the method can include crossing a perennial ryegrass plant provided herein (such as a plant grown from seed deposited under NCIMB Deposit No. NCIMB 41778; NCIMB 41779; NCIMB 41780; NCIMB 41781; NCIMB 41782; NCIMB 41783; or NCIMB 41784) with at least one other species of another genus of grass (examples given, but not limited to, *Festuca* spp., *Schedonorus* spp.) plant to produce at least one intergeneric hybrid seed, harvesting the seed, and germinating the seed to produce at least one progeny intergeneric perennial ryegrass plant. Such progeny plants are encompassed by this disclosure, and in some example, have or consist of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784.

The disclosure also encompasses seed of the perennial ryegrass plants provided herein (LpC, 06-LpC-10; 06-LpC-13; 06-LpC-14; 06-LpC-9; 06-LpC-2; 06-LpC-12, and 09-LpC-72) (as well as seed from progeny of the disclosed plants, such as crosses involving the disclosed plants or transgenic plants generated from the disclosed plants), that has naturally or artificially (e.g., using colchicine) had the chromosome number increased (from its original number ($2n=2x=14$), wherein the seed produces a perennial ryegrass plant or infraspecific cross or interspecific hybrid or intergeneric hybrid with increased chromosome number(s) having or consisting of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784 (such as a determinate-stoloniferous growth habit).

In some examples, seed of the perennial ryegrass plants provided herein (such as seed deposited under NCIMB Deposit No. NCIMB 41778; NCIMB 41779; NCIMB 41780; NCIMB 41781; NCIMB 41782; NCIMB 41783; or NCIMB 41784), as well as progeny seed, is part of a seed mixture, such as a mixture of perennial ryegrass seeds and other grass species. In one example the grass seed mixture includes seeds of 06-LpC-10 (NCIMB Deposit No. NCIMB 41778), 06-LpC-13 (NCIMB Deposit No. NCIMB 41779), 06-LpC 14 (NCIMB Deposit No. NCIMB 41780), or combinations thereof, such as a mixture containing 06-LpC-10, 06-LpC-13 and 06LpC 14 (NCIMB Deposit Nos. NCIMB 41778, 41779, and 41780) or a mixture containing 06-LpC-10 and 06-LpC-13 (NCIMB Deposit Nos. NCIMB 41778 and 41779).

The disclosure also encompasses seed of the perennial ryegrass plants provided herein (LpC, 06-LpC-10; 06-LpC-13; 06-LpC-14; 06-LpC-9; 06-LpC-2; 06-LpC-12, and 09-LpC-72) (as well as seed from progeny of the disclosed plants, such as crosses involving the disclosed plants or transgenic plants generated from the disclosed plants), that has naturally or artificially (e.g., using androgenesis) had the chromosome number decreased (from its original number ($2n=2x=14$), wherein the seed produces a perennial ryegrass plant or infraspecific cross or interspecific hybrid or intergeneric hybrid with decreased chromosome number(s) having or consisting of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784 (such as a determinate-stoloniferous growth habit). In some examples, seed of the perennial ryegrass plants provided herein (such as seed deposited under NCIMB Deposit No. NCIMB 41778; NCIMB 41779; NCIMB 41780; NCIMB 41781; NCIMB 41782; NCIMB 41783; or NCIMB 41784), as well as progeny seed, is part of a seed mixture, such as a mixture of perennial ryegrass seeds and other grass species.

The disclosure also provides perennial ryegrass plants grown from such seed or seed mixtures, where in some examples such plants have or consist of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784 (such as a determinate-stoloniferous growth habit).

The disclosure also provides a vegetative sprig or clone of the perennial ryegrass plants provided herein (as well as seed from progeny of the disclosed plants, such as crosses involving the disclosed plants or transgenic plants generated from the disclosed plants).

Methods of producing a perennial ryegrass plant of the present disclosure (LpC, such as 06-LpC-10; 06-LpC-13; 06-LpC-14; 06-LpC-9; 06-LpC-2; 06-LpC-12, and 09-LpC-72) are also provided. In one example, the method can include growing a perennial ryegrass plant provided herein (such as a plant grown from seed deposited under NCIMB Deposit No. NCIMB 41778; NCIMB 41779; NCIMB 41780; NCIMB 41781; NCIMB 41782; NCIMB 41783; NCIMB 41784). Such resulting grass plants are encompassed by this disclosure. In another example, the method can include crossing a perennial ryegrass plant provided herein (such as a plant grown from seed deposited under NCIMB Deposit No. NCIMB 41778; NCIMB 41779; NCIMB 41780; NCIMB 41781; NCIMB 41782; NCIMB 41783; or NCIMB 41784) with at least one other perennial ryegrass plant to produce at least one seed, harvesting the seed, and germinating the seed to produce at least one progeny perennial ryegrass plant. Such progeny plants are encompassed by this disclosure, and in some example, have or consist of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784.

Methods of Selecting for a Grass Plant that has Determinate-Stolons

Methods of selecting for a grass plant that has determinate-stolons is provided herein. Generally the method includes exposing a turf plot or space plants to natural traffic or a traffic simulator over a period of years, and maintaining the turf area to a desired height, and selecting plants that survive under such conditions. In one example the method includes exposing a turf plot planted with a grass plant to natural traffic (such as at least 2, at least 3, at least 4, or at least 5 games a week, such as sports games, for example soccer, football, cricket, baseball, lacrosse, or tennis) or a traffic simulator at least once a week (such as simulation of at least 2, at least 3, at least 4, or at least 5 games a week) from May (or when grasses comes out of winter dormancy and begins actively growing) until the first frost in the fall. For example, if a traffic simulator is used, at least one pass with the simulator (such as 1, 2, or 3 passes) can be made from May (or when grasses comes out of winter dormancy and begins actively growing) until the first frost in the fall. In some examples the traffic simulator weighs at least 1,000 or at least 2,000 lbs, less if self-propelled. In some examples, the traffic simulator is pulled by a tractor or can be self-propelled. The method also includes mowing the turf plot at least once a week to a desired height of between 0.5 to 3 inches. (such as 1.5 or 2 inches) After a period of at least three years, plants are selected that survived and have determinate-stolons. The selected plants can have qualities of traffic resistance, traffic recovery and repair, and crown spread similar to those perennial ryegrasses described herein, such as a crown spread perimeter of at least 80 cm after 2 years of growth and mowing. In some examples, no supplemental irrigation is provided for the grass plant and no disease control is performed. In particular examples the selected grass plant is a perennial ryegrass, such as *Agrostis* spp., *Festuca* ssp., *Poa* spp., *Lolium* spp, *Schedonorus* spp., *Dactylis* spp. and other species within Poaceae. In other examples, the selected grass is a bentgrasses, tall fescue or rhizomatous tall fescue, meadow fescue, orchardgrass. Grass plants selected using such a method are also encompassed by this disclosure. In some examples, the grass plants selected have one or more of the morphological characteristics of the disclosed LpC varieties, such as at least 20 peripheral tillers; at least 200 total rooting nodes; at least 16 determinate-stolons; at least 70 secondary tillers on determinate stolons; a total determinate-stolon length of at least 800 mm for the sum of 10 determinate-stolons; a longest determinate-stolon having a length of at least 100 mm; a determinate-stolon index of at least 500,000,000; a determinate-stolon index that is at least 5-fold greater than Pinnacle II; or combinations thereof.

The method can further include collecting seed from the selected grass plants that have determinate-stolons.

EXAMPLE 1

Origin and Breeding History of Determinate-Stoloniferous Germplasm of Perennial Ryegrass The *Lolium perenne* L. subsp. *stoloniferum* germplasm was developed for its determinate-stoloniferous phenotype, and its ability to produce high-quality turf, withstand traffic on sports fields, and quickly repair (high regenerative potential) and recover from traffic. This subspecies, because of its determinate-stoloniferous spreading, is useful for growing perennial ryegrass sod for turf and use in areas with athletic uses, such as soccer fields, football fields, baseball fields, cricket pitches, tennis courts, golf courses, parks and the like.

The breeding program was designed to breed and select for a perennial ryegrass adapted to marginal lawn conditions with low nutrient inputs and high traffic areas used for athletic venues. The determinate-stoloniferous spreading trait in perennial ryegrass should impart better persistence, regenerative abilities and increased competitive ability in areas for its intended use.

The development of *Lolium perenne* L. subsp. *stoloniferum*, in the following example, began when many turf plots were planted in the fall of 2001 in Broad Run, Va. The plots were established on poor soil with only a few inches of top soil over bed rock with very high temperatures and humidity, and usually snow cover in the winter. Once the plots were established, they were subject to 1-2 treatments with a traffic simulation machine every week from May until first frost in November of each year.

Figure 10:
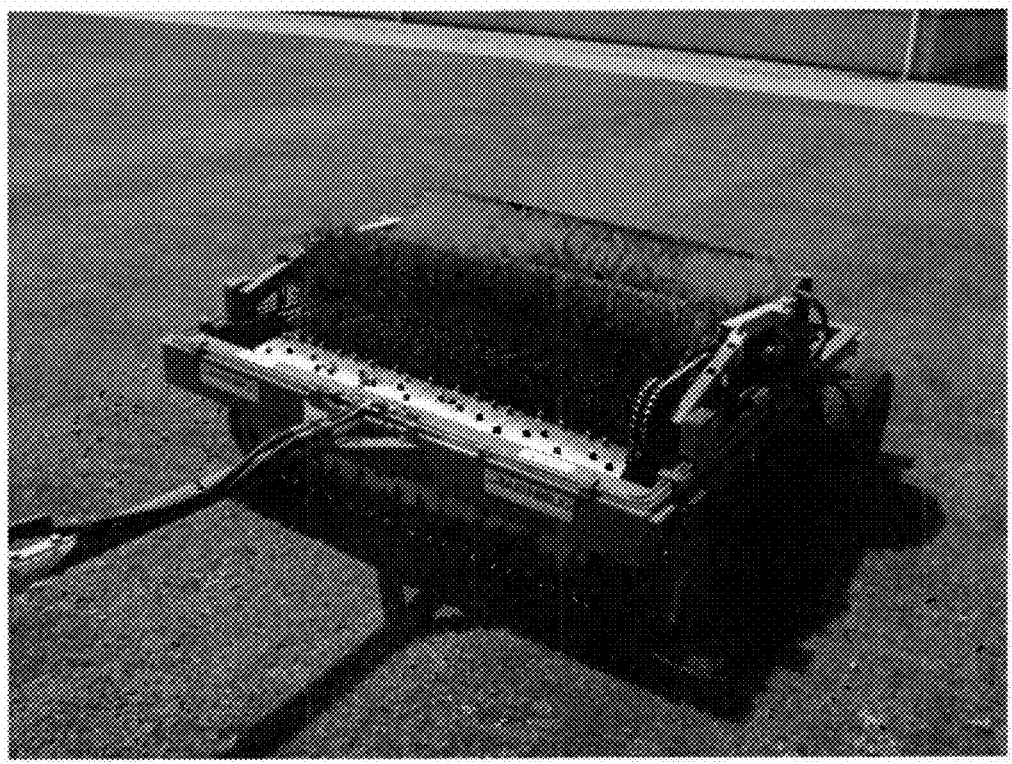
FIG. 10 is a digital image showing the modified Brinkman wear machine used to select for the new subspecies of perennial ryegrass with determinate-stolons disclosed herein.

The traffic simulation machine (see FIG. 10) is a modified Brinkman-type machine with two independent turning (at different RPM's) differential slip, steel studded drums, two brushes to clean studs as they rotate and a large heavy drum to pack down the torn sod. The machine weighs approximately 2,000 lbs and pulled behind a tractor. This artificial traffic simulator is classified as a differential slip wear machine and is modified from the original designed published by Cockerham and Brinkman (1989). The original Brinkman design weighs 900 lbs and only consisted of two cleated drums (48 inches wide) connected by chain sprockets and pulled by a tractor. In contrast, the modified Brinkman weighs approximately 2,000 lbs, has larger cleated drums with two brushes to clean each drum, and a large compaction drum behind the two cleated drums to compact the turf back down. This allows for a quick and efficient way to apply an intense amount of wear onto turfgrass in a short amount of time.

Cockerham and Brinkman (1989) designed their traffic simulator based on cleated-shoe traffic data on a football field from Cockerham (1989). Cockerham (1989) determined the location of maximum traffic concentration that football field receives is on the forty-yard line where 56 cleat dents per square foot are made per game. Cockerham recommended that athletic field research should focus the intensity of cultural practices on field management for that area. The modified Brinkman was designed to inflict a more intense and greater traffic injury than the Brinkman for a more efficient and effective plant selection method for wear tolerance.

There are also self-propelled units that could be used, such as the machine described by Canaway (1976) which is approximately 480 lbs but is much slower and this significantly increases the amount of time that it takes to apply the same amount of wear and requires more passes with the machine. Canaway (198 lb) estimated the effects of his machine on grass cover. He calculated that two passes per week with the 480 lb wear machine were approximately equivalent to the effects of one soccer match at the center of the field.

The Modified Brinkman wear machine used herein was four-times as destructive, with two passes per week being equivalent to four soccer games. In summary, the selection pressure for wear tolerance on our turf was extreme and intense.

No disease control was performed. On the VA site during the winter the turf was maintained at a ½ inch height by the large resident Canadian goose population, which grazed the plots heavily all year.

After three years of the above selection regime, August 2004, the strongest and most aggressive of the surviving plants were selected out of the trials. Plants were only selected from 45 of the original populations in Virginia. This yielded a total of 6700 clones that were established at the West Coast Research Center, in Oregon in the fall of 2004.

The clones were evaluated for two years for seed production and resistance to seed production disease (e.g., stem rust caused by *Puccinia graminis* Pers.:Pers.). In fall 2006, it was noticed that some of the populations were very aggressive and had crowns perimeters greatly expanding, and the culms rooting, to over 60 cm in diameter, whereas traditional perennial ryegrass had crowns less than half the width (FIGS. 6-9). Upon closer examination it was determined that the stems were actually a type of stolon (i.e., determinate-stolon) that was rooting at the nodes causing this impressive increase in crown diameter. Two hundred forty six plants were selected (out of the 6,700) for this aggressive crown diameter due the presence of determinate-stolons. These plants were sorted into 15 different initial populations based on similarities for leaf texture, color and heading times, and then isolated. These 15 populations were designated as 06-LpC.

EXAMPLE 2

Growing Trials

Data for the new LpC populations was collected. The trial was established on native soil (silt clay loam) on 10 Oct. 2007 at the OTF Research Facility, Columbus, Ohio. Treatments were seeded at 8 lbs/1,000 ft² (40 g/m⁻²) into 3'×5' plots. Table 1 shows the fertilizer application for the trial:

TABLE 1

Fertilizer application

| Date | Rate: lbs. N/1,000 ft² | Formulation: (N—P—K) |
|---|---|---|
| 11 Oct. 2007 | 1 | 21-4-11 |
| 23 Apr. 2008 | 0.5 | 13-28-13 |
| 6 Jun. 2008 | 0.75 | 21-4-11 |
| 25 Jun. 2008 | 0.5 | 13-28-13 |
| 5 Aug. 2008 | 0.75 | 21-4-11 |
| 18 Sep. 2008 | 0.75 | 21-4-11 |
| 31 Oct. 2008 | 0.75 | 21-4-11 |

Plots were irrigated to maintain healthy growth. Plots were mowed at three different heights: 1-inch (25 mm); 1.5 inch (38 mm); and 2-inch (50 mm), replicated 3 times.

Plots received simulated traffic with a SISIS® wear machine, developed by the SISIS Company and STRI (Sports Turf Research Institute, Bingley, UK). The machine is equipped with cleats on weighted rollers that have a differential slip and cause cleat damage and tearing of the grass. Two passes with the SISIS cause similar damage to damage caused during one football game. Traffic simulation began on 24 Jul. 2008 and continued weekly, except between 20 August to 8 September when the traffic machine was being repaired. Extra traffic (10 passes or 5 games) were applied over a two-day period to simulate intense traffic (Table 4). Weed control (quinclorac—'Drive') was applied to suppress crabgrass (*Digitaria* spp.) on 20 June and 10 July. Mesotrione ('Tenacity') was applied 1 August to remove remaining crabgrass, goosegrass [*Eleusine indica* L. (Gaertn.)] and yellow nutsedge (*Cyperus esculentus* L.).

Regenerative Potential (presence of Determinate-Stolons) After Simulated Traffic at different Mowing Heights The following stolon characteristics were observed for 06-LpC plants for regenerative potential of plants with determinate-stolons after intense simulated traffic and without traffic (Table 2). The traffic simulation was applied until 50% of the cover had been removed from the plot and then allowed to begin recuperating. The number of plants beginning to produce determinate-stolons was then counted. The information provided in Table 2 is the percentage of perennial ryegrass with determinate-stolons post-traffic simulation and without traffic simulation at different mowing heights. This provides data on the regenerative potential of plants with determinate-stolons after intense simulated traffic to reduce the cover to 50% and with no traffic simulation (100% cover) (Table 2). The results clearly show that traditional perennial ryegrasses do not produce determinate-stolons at any time, and thus do not have the potential to recuperate/regenerate after intense traffic. In contrast, 06-LpC varieties produce determinate-stolons both with and without traffic and at all mowing heights.

TABLE 2

% of Perennial Ryegrass Plants with Determinate-Stolons with and without traffic simulation.

| | 1-Inch Mowing Height Percent Stolons* | | 1.5-Inch Mowing Height Percent Stolons* | | 2.0-Inch Mowing Height Percent Stolons* | |
|---|---|---|---|---|---|---|
| Grass | After Traffic Simulation 50% Ground Cover | No Traffic Simulation 100% Ground Cover | After Traffic Simulation 50% Ground Cover | No Traffic Simulation 100% Ground Cover | After Traffic Simulation 50% Ground Cover | No Traffic Simulation 100% Ground Cover |
| LPC 2 | 6 | 5 | 6 | 3 | 14 | 12 |
| LPC 10 | 5 | 5 | 5 | 5 | 8 | 9 |
| LPC 13 | 3 | 4 | 5 | 5 | 15 | 13 |
| LPC 14 | 6 | 10 | 14 | 7 | 15 | 11 |
| LPC 2,4,8,10 (25% each) | 4 | 3 | 5 | 5 | 10 | 6 |
| Premier II, Pinnacle II, & Barlennium blend (33% each) | 0 | 0 | 0 | 0 | 0 | 0 |
| LPC Blend (90%) & Turfblue (10%) | 2 | 4 | 1 | 4 | 7 | 8 |

TABLE 2-continued

% of Perennial Ryegrass Plants with Determinate-Stolons with and without traffic simulation.

| Grass | 1-Inch Mowing Height Percent Stolons* | | 1.5-Inch Mowing Height Percent Stolons* | | 2.0-Inch Mowing Height Percent Stolons* | |
|---|---|---|---|---|---|---|
| | After Traffic Simulation 50% Ground Cover | No Traffic Simulation 100% Ground Cover | After Traffic Simulation 50% Ground Cover | No Traffic Simulation 100% Ground Cover | After Traffic Simulation 50% Ground Cover | No Traffic Simulation 100% Ground Cover |
| Turfstar (90%) & Turfblue (10%) | 0 | 0 | 0 | 0 | 0 | 0 |
| LSD (0.05) | 6 | 4 | 6 | 4 | 6 | 4 |

*Percentage of plants within a sample that had determinate-stolons

Turf Quality at Different Mowing Heights

The information provided in Table 3 provides turf quality (TQ) ratings at three different heights. The turf plots were seed 10 Oct. 2007, except for plots with "**", which were not seeded until spring 2008. Measurements of turf quality were made between May and November 2008. These data are expressed in numbers ranging from 1-9, with 9 representing highest turf quality.

TABLE 3

Effect of mowing height and traffic on the 2008 turf quality of determinate-stoloniferous perennial ryegrass.

| Grass | 7-May | 20-Jun | 10-Jul | 24-Jul | 8-Aug | 8-Sep | 17-Oct | 13-Nov | AVERAGE |
|---|---|---|---|---|---|---|---|---|---|
| | 1-Inch Mowing Height | | | | | | | | |
| LPC 2 | 5.8 | 9.0 | 8.7 | 7.3 | 4.0 | 6.3 | 3.0 | 3.3 | 5.9 |
| LPC 10 | 3.7 | 7.0 | 4.3 | 7.0 | 3.3 | 6.3 | 4.0 | 3.0 | 4.8 |
| LPC 13 | 4.3 | 8.0 | 8.0 | 8.0 | 5.3 | 7.0 | 4.8 | 4.0 | 6.2 |
| LPC 14 | 4.3 | 7.5 | 7.7 | 7.5 | 3.7 | 6.7 | 5.0 | 3.7 | 5.8 |
| Premier II, Pinnacle II, & Barlennium blend (33% each) | 5.3 | 9.0 | 8.7 | 7.7 | 3.7 | 7.3 | 5.0 | 4.3 | 6.4 |
| LPC Blend (90%) & Turfblue (10%) | ** | 7.0 | 7.0 | 6.7 | 3.0 | 6.7 | 4.7 | 2.7 | 5.4 |
| Turfstar (90%) & Turfblue (10%) | 5.5 | 9.0 | 9.0 | 8.3 | 4.0 | 8.0 | 5.3 | 3.3 | 6.6 |
| LSD (0.05) | 1.1 | 0.0 | 0.6 | 0.7 | 1.0 | 1.1 | 1.3 | 1.1 | |
| | 1.5-Inch Mowing Height | | | | | | | | |
| LPC 2 | 6.7 | 9.0 | 8.7 | 7.3 | 6.7 | 7.7 | 5.7 | 5.0 | 7.1 |
| LPC 10 | 4.7 | 7.0 | 4.3 | 7.0 | 4.3 | 7.3 | 5.0 | 4.0 | 5.5 |
| LPC 13 | 5.3 | 8.0 | 8.0 | 8.0 | 7.0 | 8.3 | 6.0 | 4.3 | 6.9 |
| LPC 14 | 4.7 | 7.5 | 7.7 | 7.5 | 5.0 | 7.0 | 5.7 | 4.3 | 6.2 |
| Premier II, Pinnacle II, & Barlennium blend (33% each) | 5.8 | 9.0 | 8.7 | 7.7 | 5.7 | 7.3 | 6.0 | 4.7 | 6.9 |
| LPC Blend (90%) & Turfblue (10%) | ** | 7.0 | 7.0 | 6.7 | 4.3 | 7.3 | 5.3 | 4.0 | 5.9 |
| Turfstar (90%) & Turfblue (10%) | 6.2 | 9.0 | 9.0 | 8.0 | 5.7 | 7.7 | 6.3 | 5.0 | 7.1 |
| LSD (0.05) | 1.1 | 0.0 | 0.6 | 0.7 | 1.0 | 1.1 | 1.3 | 1.1 | |
| | 2-Inch Mowing Height | | | | | | | | |
| LPC 2 | 8.5 | 9.0 | 8.7 | 7.3 | 6.0 | 7.0 | 5.3 | 4.0 | 7.0 |
| LPC 10 | 6.7 | 7.0 | 4.3 | 7.0 | 4.5 | 6.7 | 4.7 | 3.7 | 5.6 |
| LPC 13 | 7.7 | 8.0 | 8.0 | 8.0 | 6.3 | 7.7 | 6.0 | 4.3 | 7.0 |
| LPC 14 | 7.7 | 7.5 | 7.7 | 7.5 | 5.3 | 7.7 | 6.0 | 4.0 | 6.7 |
| Premier II, Pinnacle II, & Barlennium blend (33% each) | 9.0 | 9.0 | 8.7 | 7.7 | 6.5 | 7.3 | 6.3 | 4.0 | 7.3 |
| LPC Blend (90%) & Turfblue (10%) | ** | 7.0 | 7.0 | 6.7 | 4.7 | 6.7 | 5.7 | 3.3 | 5.9 |
| Turfstar (90%) & Turfblue (10%) | 8.7 | 9.0 | 9.0 | 8.0 | 5.3 | 8.0 | 6.3 | 4.3 | 7.3 |
| LSD (0.05) | 1.1 | 0.0 | 0.6 | 0.7 | 1.0 | 1.1 | 1.3 | 1.1 | |

Crown Perimeter Spread of Mowed Spaced Plants

Table 4 shows the increased crown spread in individual space plants of ryegrasses with determinate-stolons versus those without determinate-stolons under mowing. The data was collected in November 2009 after two years of mowing space plants in Albany, Oreg. There were 60 replications in this study.

TABLE 4

Crown Perimeter Spread of individual plants

| Grass | Species | Plant Perimeter (cm) |
|---|---|---|
| 06-LpC-10 | L. perenne subsp. stoloniferum | 98.2 |
| 06-LpC-13 | L. perenne subsp.. stoloniferum | 96.1 |
| 06-LpC-14 | L. perenne subsp.. stoloniferum | 93.7 |
| 06-LpC-9 | L. perenne subsp. stoloniferum | 90.6 |
| 06-LpC-2 | L. perenne subsp. stoloniferum | 87.5 |
| 06-LpC-12 | L. perenne subsp. stoloniferum | 81.1 |
| Pinnacle II | L. perenne subsp. perenne | 72.8 |
| LSD (P = .10) | | 7.39 |

Figure 11:
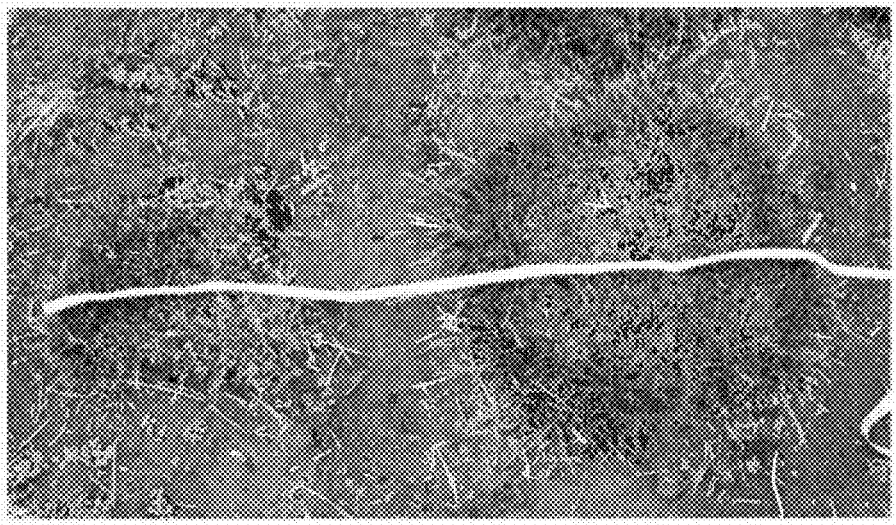
FIGS. 11 and 12 are digital images comparing the crown diameter of an individual plant disclosed herein having determinate-stolons (LpC plant on right) and non-stoloniferous (on left) plants after two years of mowing. The significantly larger crown perimeter of the plant with stolons is compared to a non-stoloniferous plant.
Figure 12:
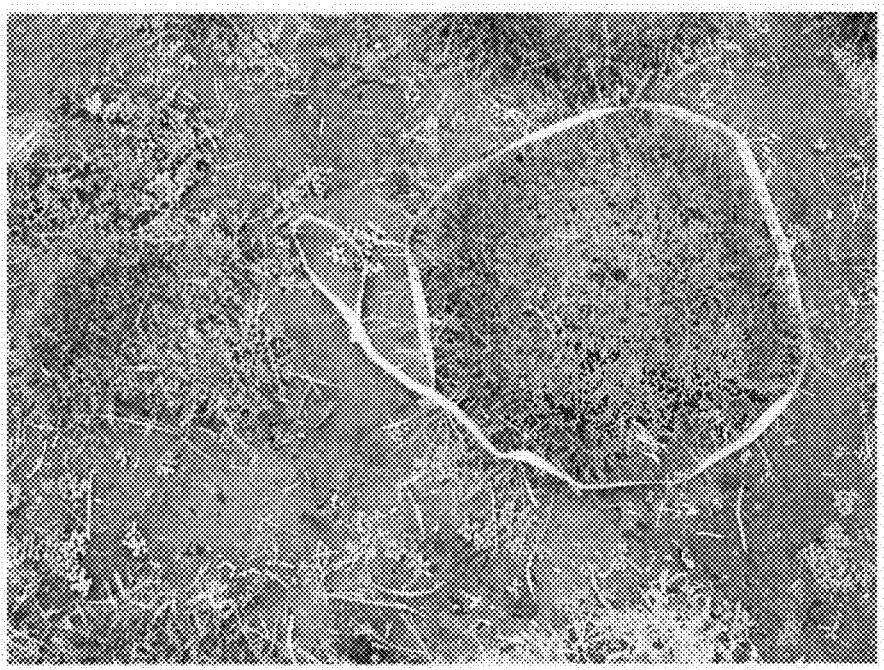

FIGS. 11 and 12 are digital images comparing the diameter and crown perimeter (respectively) of individual determinate-stoloniferous plants (on right) disclosed herein such as 06-LpC-10; 06-LpC-13; 06-LpC-14; 06-LpC-9; 06-LpC-2; 06-LpC-12, and 09-LpC-72 and non-stoloniferous (on left) plants after two years of mowing, showing the significantly larger crown perimeter of the plant with stolons compared to a non-stoloniferous plant. Plants were mowed continuously for a two year period at approximately 2 inch cutting height.

Measurement of Spreading/Stoloniferous Characteristics of Perennial Ryegrass in Seeded Rows.

Figure 13:
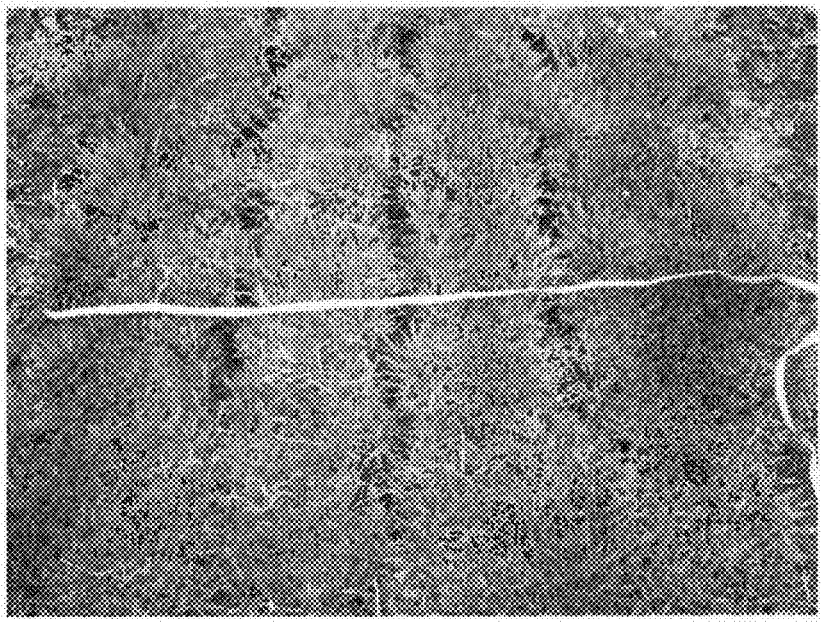
FIG. 13 is a digital image showing the aggressive spread of the stoloniferous ryegrass disclosed herein (LpC) when seeded into four rows (each row planted 30.5 cm apart) after two years of continual mowing.
Figure 14:
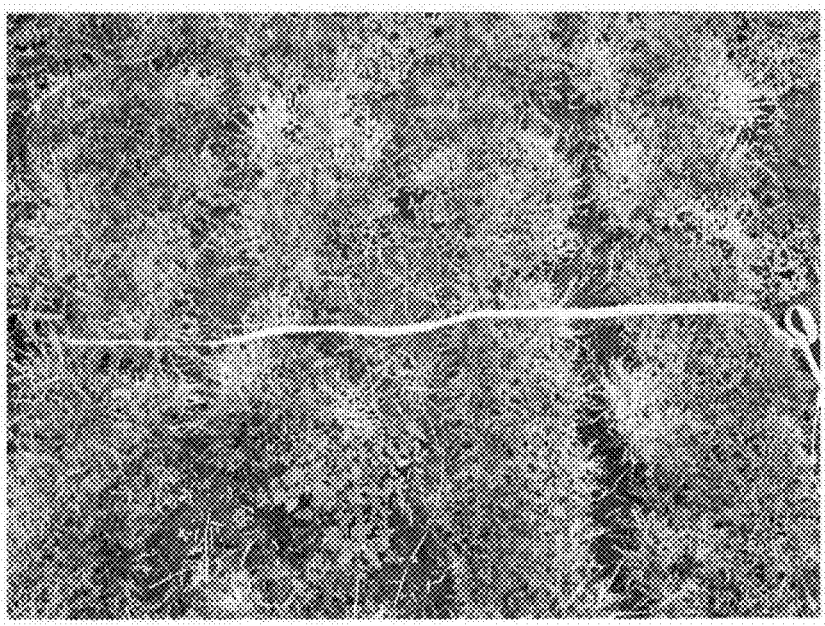
FIG. 14 is a digital image showing the lack of spread of non-stoloniferous ryegrass (e.g., Pinnacle II perennial ryegrass) when seeded into four rows (each row planted 30.5 cm apart) after two years of continual mowing.

Table 5 shows the increased crown perimeter spread, under mowing to maintain a height of two inches, in seeded rows of ryegrasses with determinate-stolons (FIG. 13) versus those without determinate-stolons (FIG. 14). The data was collected in September 2009 after two years of seeded rows in Albany, Oreg. There were 16 replications in this study. Seeds were planted in April 2007.

TABLE 5

Crown spread of rows of ryegrass.

| Grass | Species | Row Width (cm) |
|---|---|---|
| 06-LpC-13 | L. perenne subsp. stoloniferum | 25.8 |
| 06-LpC-14 | L. perenne subsp. stoloniferum | 25.7 |
| 06-LpC-9 | L. perenne subsp. stoloniferum | 24.8 |
| 06-LpC-12 | L. perenne subsp. stoloniferum | 24.6 |
| 06-LpC-10 | L. perenne subsp. stoloniferum | 24.4 |
| 06-LpC-2 | L. perenne subsp. stoloniferum | 23.5 |
| Pinnacle II | L. perenne subsp. perenne | 19.6 |
| LSD (P = .10) | | 2.55 |

Measurement of the Crown Perimeter of Determinate-/Stoloniferous Perennial Ryegrass Space Plants Under Mowing and Artificial Traffic for Two Years.

Table 6 shows the increased crown spread, under mowing and artificial traffic for two years, in individual space plants of ryegrasses with determinate-stolons versus those without determinate-stolons. The data was collected in July and September 2009 in Albany, Oreg. There were 75 replications in this study. The nursery was planted Fall 2007.

TABLE 6

Crown Perimeter Spread.

| | | Plant Perimeter (cm) | |
|---|---|---|---|
| Grass | Species | Jul. 15, 2008 | Sep. 15, 2009 |
| 06-LpC-10 | L. perenne subsp. stoloniferum | 71.1 | 83.7 |
| 06-LpC-9 | L. perenne subsp. stoloniferum | 67.5 | 93.8 |
| 06-LpC-14 | L. perenne subsp. stoloniferum | 65.1 | 81.1 |
| 06-LpC-13 | L. perenne subsp. stoloniferum | 63.6 | 84.9 |
| 06-LpC-2 | L. perenne subsp. stoloniferum | 59.3 | 71.6 |
| 06-LpC-12 | L. perenne subsp. stoloniferum | 57.6 | 69.3 |
| Pinnacle II | L. perenne subsp. perenne | 53.8 | 59.3 |
| LSD (P = .10) | | 9.01 | 9.3 |

Measurement of Crown Spread of Perennial Ryegrass in Seeded Rows Under Mowing and Artificial Traffic Table 7 shows the increased crown spread, under mowing and artificial traffic, in seeded rows of ryegrasses with determinate-stolons versus those without determinate-stolons. The data was collected after two years of mowing ands artificial traffic in Albany, Oreg. There were 16 replications in this study. Seed was planted in April 2007, and data is shown for 1 and 2 years.

TABLE 7

Crown spread of rows of perennial ryegrass.

| | | Row Width (cm) | |
|---|---|---|---|
| Grass | Species | Jul. 15, 2008 | Sep. 15, 2009 |
| 06-LpC-9 | L. perenne subsp. stoloniferum | 16.5 | 24.8 |
| 06-LpC-14 | L. perenne subsp. stoloniferum | 14.4 | 22.7 |
| 06-LpC-13 | L. perenne subsp. stoloniferum | 14.5 | 22.1 |
| 06-LpC-10 | L. perenne subsp. stoloniferum | 14.5 | 20.4 |
| 06-LpC-12 | L. perenne subsp. stoloniferum | 14.7 | 20.4 |
| 06-LpC-2 | L. perenne subsp. stoloniferum | 13.3 | 19.2 |
| Pinnacle II | L. perenne subsp. perenne | 10.8 | 16.9 |
| LSD (P = .10) | | 1.0 | 2.1 |

Heading and Anther Dates of Determinate-Stoloniferous Ryegrass.

Table 8 shows heading dates of determinate-stoloniferous ryegrass in Julian days. The data was collected in 2008 and 2009 on a space trial established in the fall of 2007 in Albany, Oreg. There were 3 replications (25 subsamples per replication) in this study.

TABLE 8

Heading and anther dates of ryegrasses.

| | Heading Date | | Anther Date |
|---|---|---|---|
| Grass | 2008 | 2009 | 2009 |
| Linn | 135.7 | 134.8 | 151.8 |
| Pinnacle | 143.9 | 139.5 | 155.2 |
| 06-LpC 14 | 147.3 | 142.5 | 159.2 |
| Barlennium | 148.9 | 144.2 | 158.8 |
| Pinnacle II | 149 | 146.1 | 162.5 |
| 06-LpC 13 | 150.8 | 150.3 | 163.4 |
| 06-LpC 2 | 152.6 | 147.9 | 161.4 |
| 06-LpC 10 | 157.3 | 153.8 | 169.6 |
| LSD (P = .05) | 2.03 | 4.27 | 4.23 |

2008 Objective Description for Determinate-Stoloniferous Ryegrasses

Table 9 shows morphological characters for determinate-stoloniferous ryegrass (LpC), as well as ryegrasses that do not have determinate-stolons (e.g., Pinnacle and Pinnacle II). The data was collected in 2008 on a space trial established in the fall of 2007 in Albany, Oreg. There were 3 replications.

TABLE 9

Objective Description for several ryegrasses.

| Grass | | Plant Length (cm) | Plant Height (cm) | Flag Leaf Height (cm) | Panicle Length (cm) | Tiller Sheath Length (cm) | Tiller Leaf Length (cm) | Tiller Leaf Width (mm) | Flag Leaf Length (cm) | Flag Leaf Width (mm) | Flag Sheath Length (cm) |
|---|---|---|---|---|---|---|---|---|---|---|---|
| 06-LpC 2 | Lps[1] | 56.3 | 40.9 | 26.9 | 16.8 | 5.3 | 9.6 | 2.8 | 9.2 | 3.1 | 9.5 |
| 06-LpC 10 | Lps | 71.8 | 38.2 | 29.2 | 18.9 | 6.4 | 14.2 | 3.2 | 13.5 | 4.3 | 10.5 |
| 06-LpC 13 | Lps | 63.3 | 45.4 | 33.8 | 17.4 | 6.9 | 14.3 | 2.7 | 12.9 | 3.6 | 10.6 |
| 06-LpC 14 | Lps | 68.8 | 43.6 | 31.2 | 16.7 | 6.2 | 14.5 | 3.6 | 13.8 | 4.2 | 10.0 |
| Pinnacle | Lpp[2] | 71.6 | 46.1 | 31.5 | 16.5 | 6.3 | 13.2 | 3.2 | 11.8 | 4.3 | 10.2 |
| Pinnacle II | Lpp | 59.0 | 40.7 | 30.9 | 15.3 | 5.2 | 12.5 | 3.0 | 11.5 | 3.9 | 8.7 |
| Linn | Lpp | 79.2 | 60 | 38.0 | 15.8 | 7.8 | 13.8 | 3.3 | 12.4 | 4.3 | 12.1 |
| Barlennium | Lpp | 61.3 | 44.6 | 30.9 | 15.1 | 5.1 | 12.2 | 2.6 | 11.6 | 3.1 | 9.1 |
| LSD (P = .05) | | 7.5 | 4.95 | 5.31 | 3.15 | 1.3 | 2.51 | 1 | 2.54 | 1 | 1.49 |

[1]Lps is *Lolium perenne* subsp. *stoloniferum*
[2]Lpp is *Lolium perenne* subsp. *perenne*

EXAMPLE 3

Comparison of Traffic and No Traffic on Plant Crown Perimeter and Surface Area of Space Plants of Perennial Ryegrass Cultivars This example describes experiments used to compare the perimeter and surface area of space plants that have or have not been subjected to traffic conditions for several varieties.

Space plants of different varieties of perennial ryegrass were established in field in fall 2010 near Albany, Oreg. The study was established as factorial design with Traffic as Factor 1 and varieties as Factor 2. Each treatment had 3 replications. Each replication consisted of 10 space plants established at 2×2 feet spacing. Space plants were regularly mowed at 1.5 inch mowing height. Traffic was applied every week with a modified Brinkman Traffic simulator from May to August, 2011. Perimeter (cm) was measured every month as shown in Table 10. In addition, surface area (cm$^2$) was also measured every month as shown in Table 11.

TABLE 10

Effect of +/− traffic treatments on plant perimeter (cm) on regularly mowed space plants. Traffic was applied once a week from June-August. Then traffic was stopped so the regeneration of the plants could be evaluated from August-October.

| | No Traffic June | Traffic June | No Traffic July | Traffic July | No Traffic August | Traffic August | No Traffic October | Traffic October | Regeneration [Change in perimeter] (Aug to Oct) Traffic Oct-Aug | Regeneration Potential |
|---|---|---|---|---|---|---|---|---|---|---|
| 08-06LpC 9 | 95.4 | 98.0 | 93.8 | 95.8 | 115.3 | 93.9 | 115.9 | 106.1 | 10.5 | + |
| 08-06LpC 10 | 92.6 | 80.6 | 102.1 | 77.2 | 124.5 | 80.1 | 117.5 | 88.4 | 8.4 | + |
| 09-LpC72 | 81.5 | 76.7 | 78.2 | 69.9 | 85.6 | 70.2 | 63.1 | 77.9 | 7.9 | + |
| 08-06LpC 14 | 82.1 | 78.6 | 90.0 | 80.0 | 94.1 | 74.3 | 93.7 | 81.7 | 7.3 | + |
| 07-06LpC 12 | 87.3 | 74.9 | 98.9 | 69.4 | 93.2 | 71.7 | 86.5 | 77.0 | 5.3 | + |
| 08-06LpC 2 | 82.1 | 79.9 | 83.0 | 81.7 | 93.9 | 80.1 | 75.6 | 83.7 | 3.5 | + |
| 08-06LpC 13 | 85.4 | 80.5 | 87.5 | 78.7 | 99.8 | 81.2 | 95.1 | 84.7 | 3.5 | + |
| Natural Knit (3 variety blend) | 87.0 | 68.8 | 91.5 | 69.0 | 96.5 | 78.8 | 81.2 | 75.6 | −2.6 | − |
| Pinnacle II | 77.5 | 74.9 | 73.1 | 70.5 | 78.2 | 61.7 | 49.2 | 50.6 | −13 | − |
| L.S.D. (0.10) | 3 | | 5.2 | | 3.8 | | 7.6 | | 6.9 | |

TABLE 11

Effect of +/− traffic treatments on surface area (cm$^2$) of regularly mowed space plants. Traffic was applied once a week from June-August. Then traffic was stopped, so the regeneration of plants could be evaluated from August-October.

| | June | | July | | August | | October | | Regeneration [Change in Surface Area] (Aug to Oct) Traffic | Regeneration Potential |
|---|---|---|---|---|---|---|---|---|---|---|
| | No Traffic | Traffic | No Traffic | Traffic | No Traffic | Traffic | No Traffic | Traffic | | |
| 08-06LpC 10 | 715 | 465 | 896 | 542 | 1038 | 511 | 948 | 616 | 104.7 | + |
| 08-06LpC 9 | 766 | 457 | 939 | 571 | 1107 | 459 | 1046 | 557 | 98.5 | + |
| 08-06LpC 13 | 533 | 361 | 687 | 376 | 747 | 343 | 659 | 429 | 85.2 | + |
| 07-06LpC 12 | 469 | 335 | 527 | 286 | 587 | 268 | 556 | 319 | 51.2 | + |
| 08-06LpC 14 | 543 | 376 | 595 | 381 | 660 | 305 | 690 | 343 | 38.6 | + |

TABLE 11-continued

Effect of +/− traffic treatments on surface area (cm²) of regularly mowed space plants. Traffic was applied once a week from June-August. Then traffic was stopped, so the regeneration of plants could be evaluated from August-October.

|  | June | | July | | August | | October | | Regeneration [Change in Surface Area] | |
| --- | --- | --- | --- | --- | --- | --- | --- | --- | --- | --- |
|  | No Traffic | Traffic | No Traffic | Traffic | No Traffic | Traffic | No Traffic | Traffic | (Aug to Oct) Traffic | Regeneration Potential |
| 09-LpC72 | 489 | 342 | 538 | 295 | 575 | 271 | 527 | 279 | 8.1 | + |
| 08-06LpC 2 | 514 | 348 | 610 | 340 | 719 | 331 | 599 | 333 | 2.3 | + |
| Pinnacle II | 450 | 300 | 446 | 262 | 480 | 254 | 423 | 210 | −44.5 | − |
| L.S.D. (0.10) | 45 | | 59 | | 69 | | 74 | | 72.7 | |

The data in Table 10 indicate that the *Lolium perenne* ssp. *stoloniferum* (06-LpC), as result of their determinate-stoloniferous habit, have larger perimeters than traditional perennial ryegrass varieties, like Pinnacle II. They also have larger perimeters even under artificial traffic application. No traffic applications were applied in September. The October measurements indicate that the *Lolium perenne* ssp. *stoloniferum* varieties regenerated from traffic applications and increased in perimeter (positive values in last column above) and thus have a positive Regeneration Potential. In contrast, the other varieties (Pinnacle II and Natural Knit) never fully recovered from the traffic application and have negative regeneration potential values. This indicates that the *Lolium perenne* ssp. *stoloniferum* (06-LpC) has the potential to fill in bare spots.

The data in Table 11 demonstrate that the *Lolium perenne* ssp. *stoloniferum* (06-LpC), as result of their determinate-stoloniferous habit, have larger surface area than traditional perennial ryegrass varieties like Pinnacle II. They also have larger surface area even under traffic application. No traffic applications were applied in September. The October measurements demonstrate that the *Lolium perenne* ssp. *stoloniferum* varieties regenerated from traffic applications and increased in surface area, and so have a positive regeneration potential value. In contrast, the Pinnacle II and Natural Knit varieties never fully recovered and have negative regeneration potential value. This indicates that the *Lolium perenne* ssp. *stoloniferum* (06-LpC) has the potential to fill in bare spots.

EXAMPLE 4

Turf Plot Tiller Counts

This example describes methods used to compare tiller counts between several varieties, to permit an evaluation of the primary and secondary tillers in an area for perennial ryegrasses.

Seeds of the RPR Blend (06-LpC 10/06-LpC 13 blend) and the Natural Knit Perennial Ryegrass blend (3 variety blend; Ledeboer) were used to establish a turf trial near Corvallis, Oreg. The turf plots were established July 2010 on native soil. The soil is Chehalis and Malabon silty clay loam with a pH of 6.3. Preliminary soil test results indicated no fertility gradient and adequate potassium and phosphorus levels. The entries were replicated three times in a randomized block design. The turf plots sampled were mowed and maintained at 1.25" in height.

The data was collected in June, September, and October of 2011 (Tables 11 and 12). Tiller counts were evaluated as follows. The first division of tillers was between single tillers and multiple branched tillers. A single tiller is recorded/counted when only one tiller arises from the original crown. Multiple tillers are recorded/counted when more than one tiller arises from the original crown. The second division of tillers was between mature and secondary tillers. Mature tillers are those fully developed and rooted from original crown. Secondary tillers are the count of tillers arising from axillary nodes (nodes other than primary crown) that are not fully developed; meaning no root development. The total number of tillers is the sum of the count of single tillers and the total tillers in multiple branched tillers.

TABLE 11

Tiller counts in June 2011.

|  | Single Tiller No. | No. Multiple Branched Tillers | No. Tillers in Multiple Branch | No. Secondary Tiller | Total No. Tillers |
| --- | --- | --- | --- | --- | --- |
| Natural Knit | 170.3 | 111.7 | 317 | 59.3 | 488 |
| 06-LpC10/06-LpC13 | 172 | 69.7 | 196.3 | 17 | 368.3 |
| LSD (P = .10) | 33.46 | 15.2 | 50.02 | 32.16 | 63.44 |

TABLE 12

Tiller counts in September 2011.

|  | Single Tiller No. | No. Multiple Branched Tillers | No. Tillers in Multiple Branch | No. Secondary Tiller | Total No. Tillers |
| --- | --- | --- | --- | --- | --- |
| Natural Knit | 201 | 91 | 296.3 | 76.7 | 497.3 |
| 06-LpC10/06-LpC13 | 181 | 51 | 155 | 22 | 336 |
| LSD (P = .10) | 46.06 | 18.59 | 68.31 | 32.73 | 55.09 |

As shown in Tables 11 and 12, the Natural Knit variety blend had a significantly higher number of multiple branched tillers, tillers in multiple branches, secondary tillers and total number of tillers than the 06-LpC10/06-LpC13 blend.

EXAMPLE 5

Comparison of Turf Plot Tiller Counts

This example describes methods used to compare the turf plot tiller counts between several grass varieties.

Tiller counts obtained from Plant Variety Applications are shown in Table 13.

TABLE 13

Tiller counts in turf from Plant Variety Protection Applications

| Variety | Tiller Counts (100 sq cm) |
|---|---|
| All*Star³ | 376 |
| Barclay | 514 |
| Brightstar II | 340 |
| Brightstar SLT | 491 |
| Derby Supreme | 279 |
| Elka | 446 |
| Gator 3 | 369 |
| Imagine | 435 |
| Kokomo | 364 |
| Palmer III | 446 |
| Prelude III | 435 |
| Quick Trans | 473 |
| Quickstart | 483 |
| Quickstart II | 529 |
| Repel III | 387 |
| Secretariat | 394 |
| SR 4200 | 440 |
| SR 4500 | 543 |
| Stellar | 355 |
| Top Hat | 367 |
| Yatsu Green | 105 |

As shown in Table 13, commercially available cultivars of perennial ryegrass have lower tiller counts than for the perennial ryegrass variety described in U.S. Pat. No. 7,696,418, which reportedly has over 1,000 tillers per 100 cm² in two and three year old turf.

The tiller count for the *Lolium perenne* ssp. *stoloniferum* (06-LpC) varieties described herein were obtained as follows. Plants were established in the fall 2007 or 2008 near Lexington, Ky. Tiller counts were also made in two (Table 15) and three (Table 14) year old turf trials. One 10.2 cm diameter (81.1 cm²) sample was taken from each of three replications. The tillers in each sample were counted and then an estimate for 100 cm² area was calculated. The number of secondary tiller (tiller branches) were counted and an 'average number of tiller branches was calculated. The results are shown in Tables 14 and 15.

As shown in Tables 14 and 15, *Lolium perenne* ssp. *stoloniferum* (06-LpC) has tiller counts significantly lower than the variety reported in U.S. Pat. No. 7,696,418. Instead, the *Lolium perenne* ssp. *stoloniferum* (06-LpC) populations have tiller counts similar to commercial perennial ryegrass cultivars shown in Table 13, and had less than 50% of the number of the tillers of the variety reported in U.S. Pat. No. 7,696,418. In the 2008 trial (Table 15), the *Lolium perenne* ssp. *stoloniferum* (06-LpC) lines had significantly more secondary tiller branches than both 'Barclay' and 'Pinnacle II'. The *Lolium perenne* ssp. *stoloniferum* (06-LpC) lines also had a higher average number of secondary branches per tiller than 'Pinnacle II' and 'Barclay.' In the 2007 trial (Table 14), the *Lolium perenne* ssp. *stoloniferum* (06-LpC) lines had a higher average number of branches per tiller than 'Pinnacle II.'

TABLE 14

Tiller and tiller branch counts from 3-year old turf plots (established Fall 2007).

| Variety | n | Average Tiller Count for 10.2 cm (4 inches) diameter (81.1 cm2) | Average Tillers estimated per 100 cm2 | Average number of total secondary tiller branches | Average number of secondary branches per tiller |
|---|---|---|---|---|---|
| Barclay | 3 | 269.33 | 332.21 | 20.33 | 0.08 |
| Pinnacle II | 3 | 376.33 | 464.19 | 10.67 | 0.03 |
| 06-LpC-14 | 3 | 267.67 | 330.16 | 21.67 | 0.08 |
| 06-LpC-10 | 3 | 349 | 430.47 | 44 | 0.13 |
| 06-LpC-2 | 3 | 351.33 | 433.35 | 60.33 | 0.17 |
| LSD (P = .10) |  | 53.687 | 66.22 | 11.639 | 0.025 |

TABLE 15

Tiller and tiller branch counts from 2-year old turf plots (established Fall 2008).

| Variety | n | Average Tiller Count for 10.2 cm (4 inches) diameter (81.1 cm2) | Average Tillers estimated per 100 cm2 | Average number of total secondary tiller branches | Average number of secondary branches per tiller |
|---|---|---|---|---|---|
| Barclay | 3 | 243.67 | 300.55 | 13.33 | 0.05 |
| Pinnacle II | 3 | 389.33 | 480.23 | 7.33 | 0.02 |
| 06-LpC-13 | 3 | 359.67 | 443.63 | 23.67 | 0.07 |
| 06-LpC-10 | 3 | 350 | 431.71 | 27.33 | 0.08 |
| 06-LpC-2 | 3 | 367.33 | 453.09 | 42.67 | 0.12 |
| LSD (P = .10) |  | 34.901 | 43.05 | 10.21 | 0.024 |

EXAMPLE 6

Peripheral Tiller and Determinate-Stolon Morphology

This example describes methods used to analyze peripheral tiller and determinate-stolon morphology for several perennial ryegrasses.

Data was collected in November 2011 in Albany, Oreg. The space plant nursery was established in fall 2010. A traffic trial was established with 20 space plants per entry, with three replications. The trial received traffic from and artificial traffic simulator (4-5 passes per traffic event) once a week, in addition to mowing (approximately 2 inch cutting height). Traffic was applied weekly with 2-3 passes once a week from May to August with the modified Brinkman traffic simulator to simulate the amount of traffic received from 5 games per week.

Figure 15:
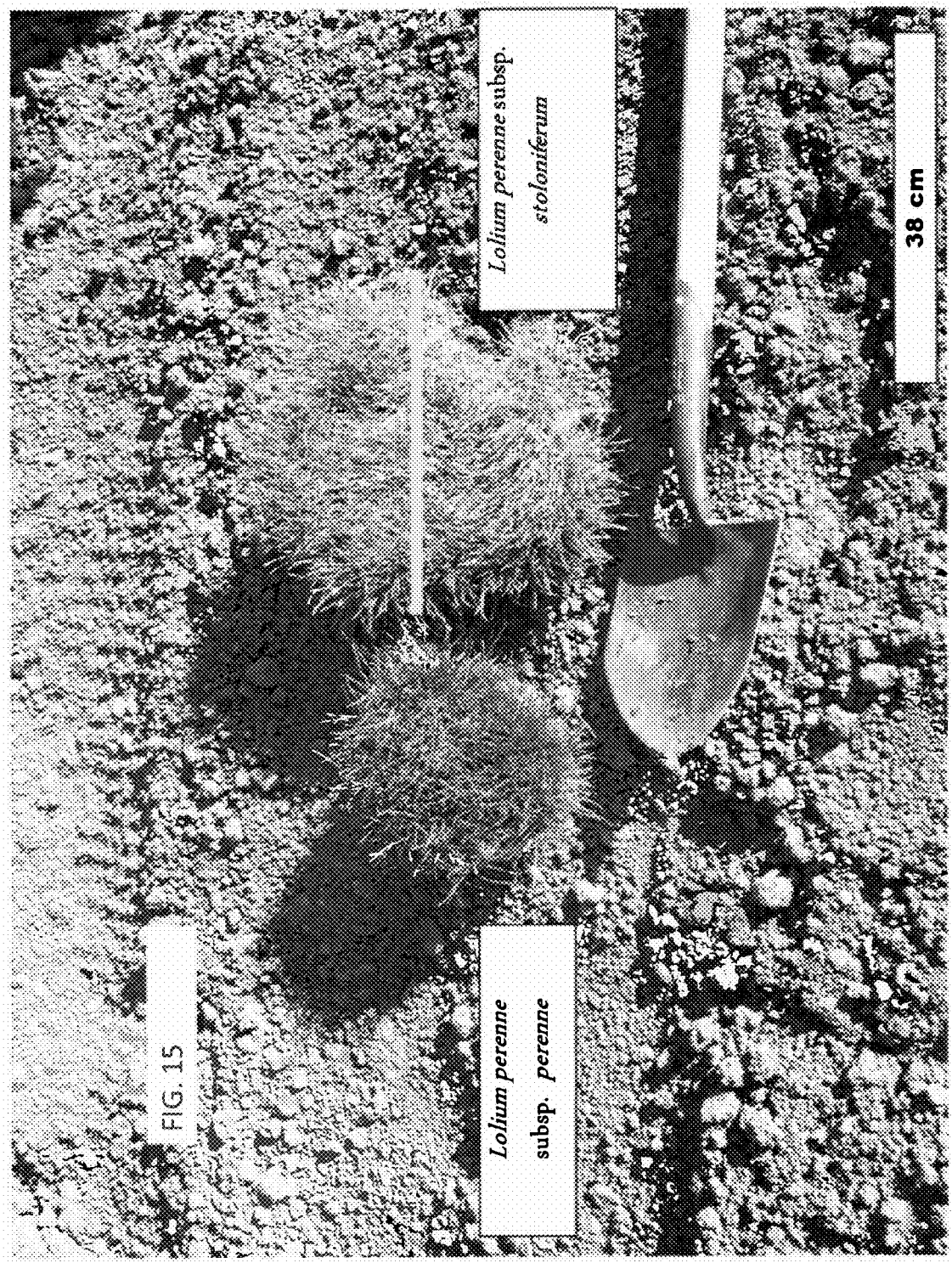
FIG. 15 is a digital image comparing *Lolium perenne* L. subsp. *perenne* (left) with *Lolium perenne* L. subsp. *stoloniferum* 06-LpC-13 (right) showing that *Lolium perenne* L. subsp. *stoloniferum* has a greater crown perimeter than *Lolium perenne* L. subsp. *perenne*.
Figure 16:
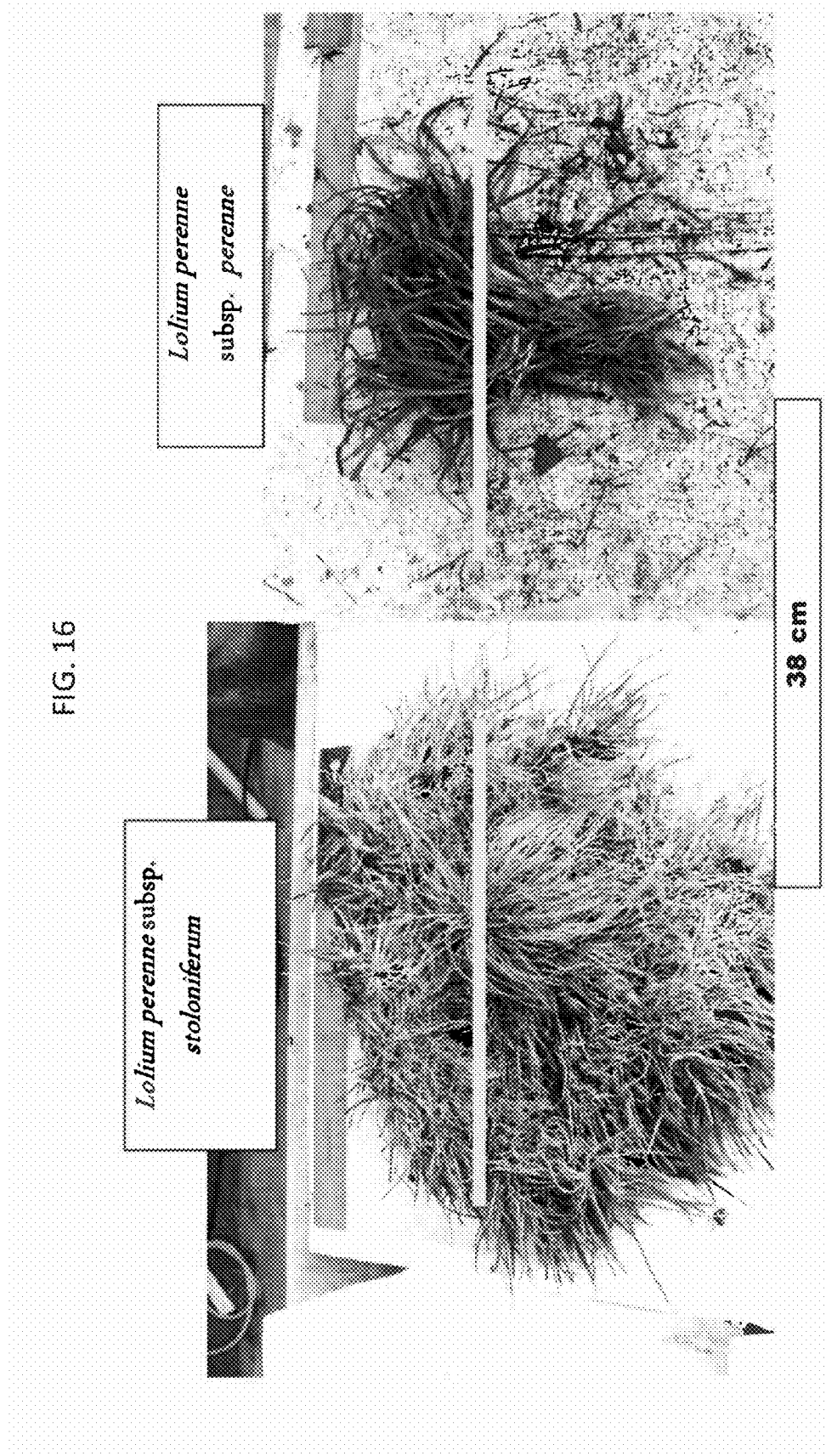
FIG. 16 is a digital image of the underside (abaxial view) of grass plants comparing *Lolium perenne* L. subsp. *perenne* (right) with *Lolium perenne* L. subsp. *stoloniferum* 06-LpC-13 (left) showing that *Lolium perenne* L. subsp. *stoloniferum* is stoloniferous while *Lolium perenne* L. subsp. *perenne* is not.
Figure 17:
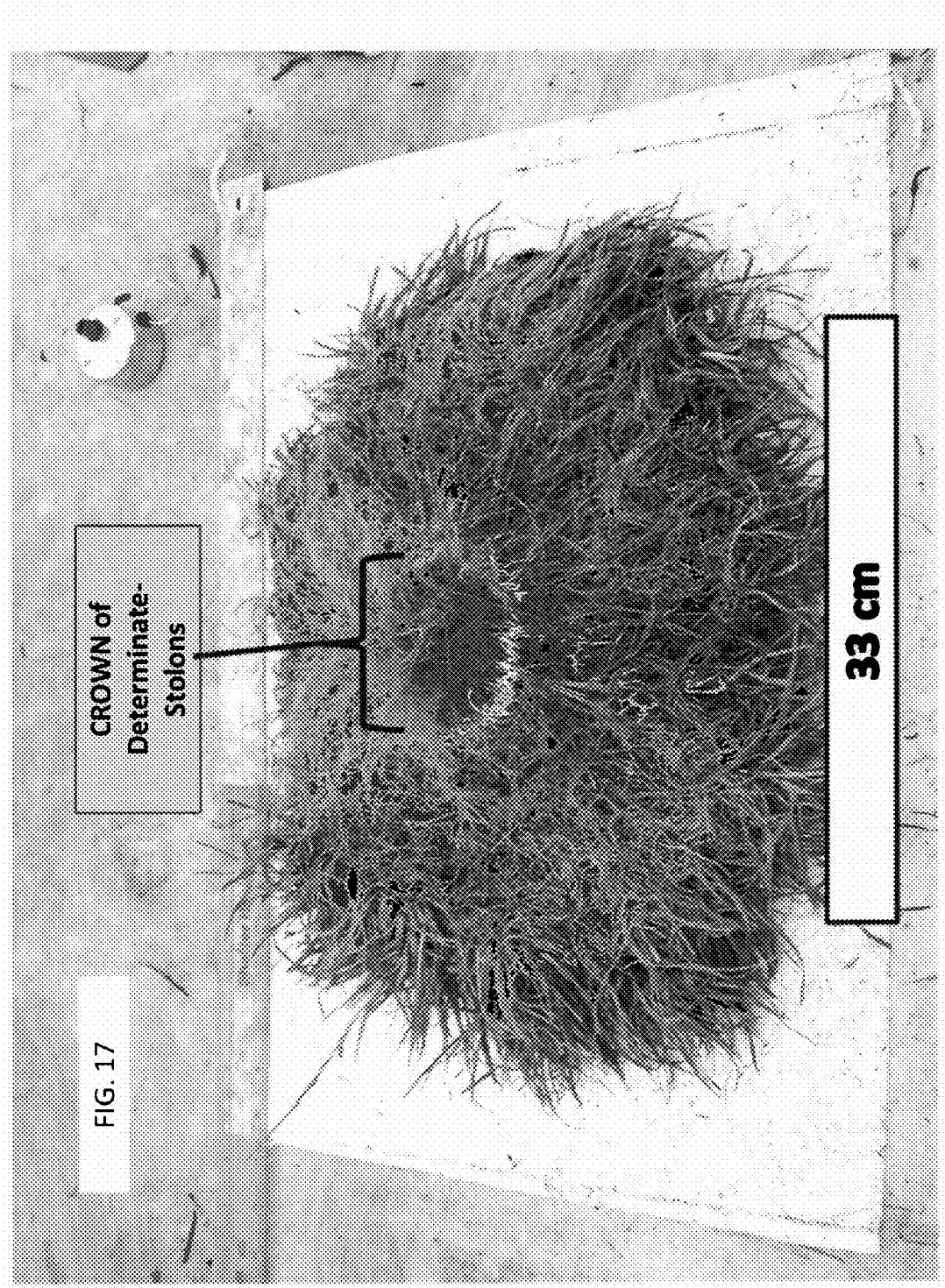
FIG. 17 is a digital image showing the crown of determinate-stolons of *Lolium perenne* L. subsp. *stoloniferum*.
Figure 18:
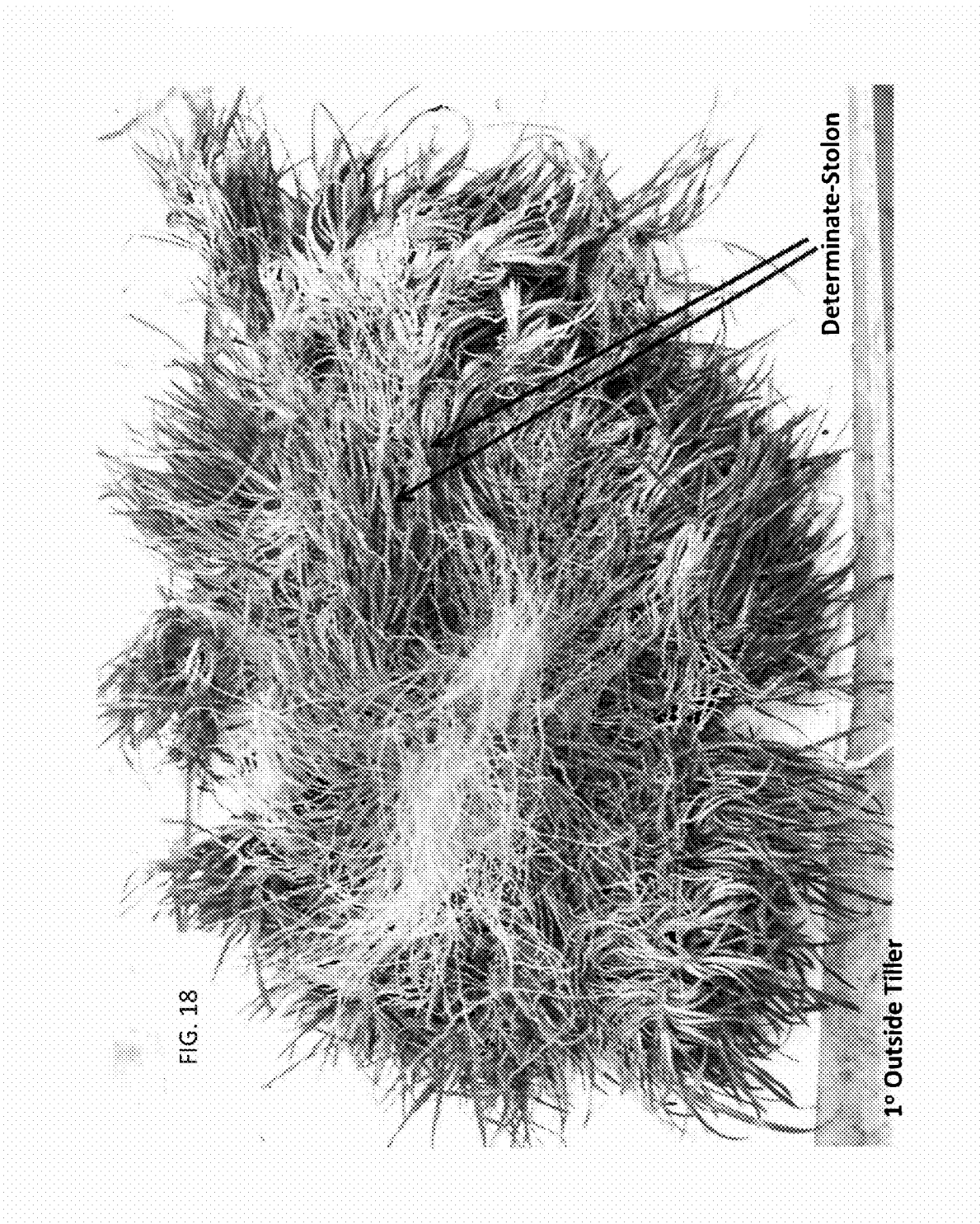
FIG. 18 is a digital image showing the determinate-stolons of *Lolium perenne* L. subsp. *stoloniferum*.
Figure 19:
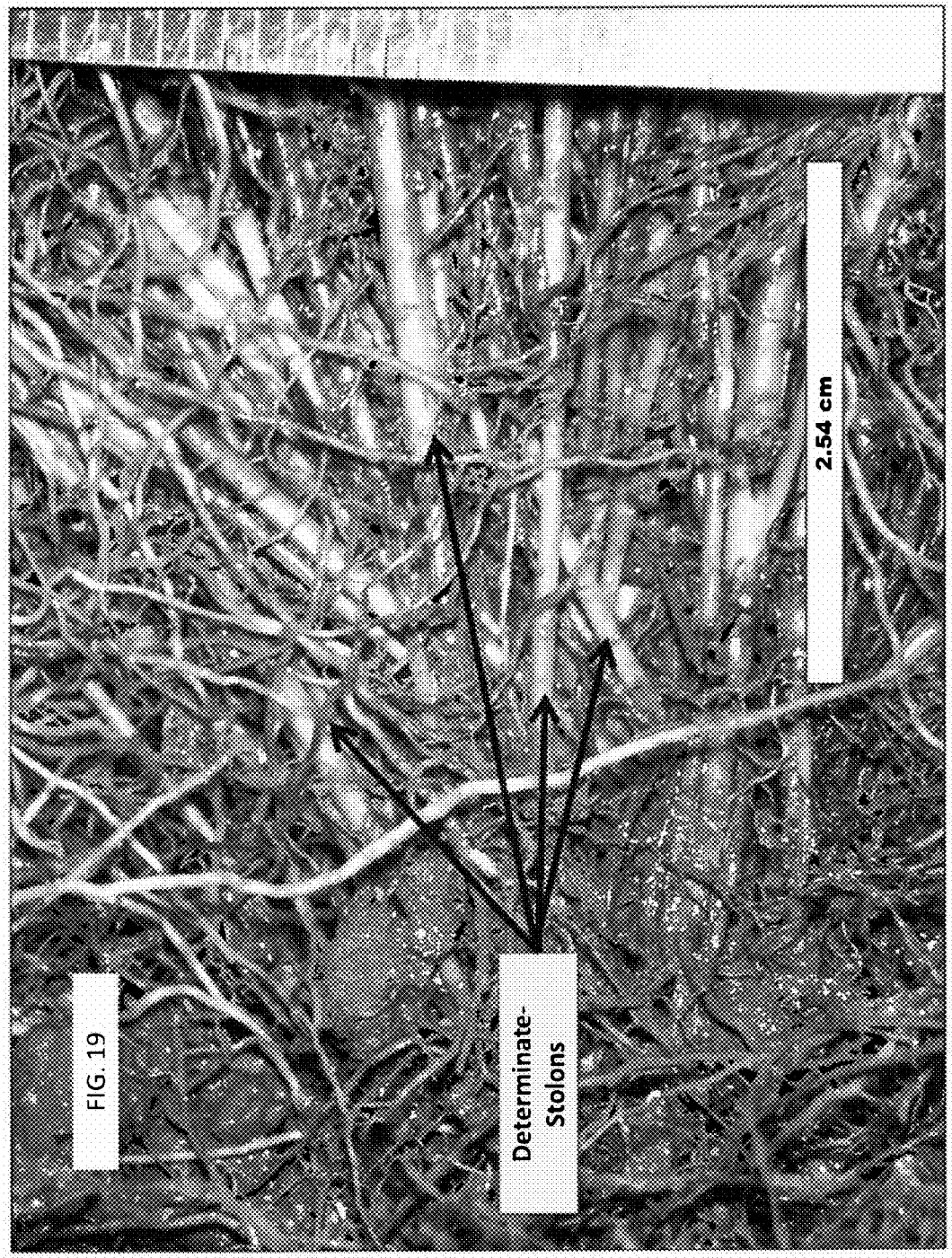
FIG. 19 is a digital image showing a close up of the determinate-stolons of *Lolium perenne* L. subsp. *stoloniferum*.
Figure 20:
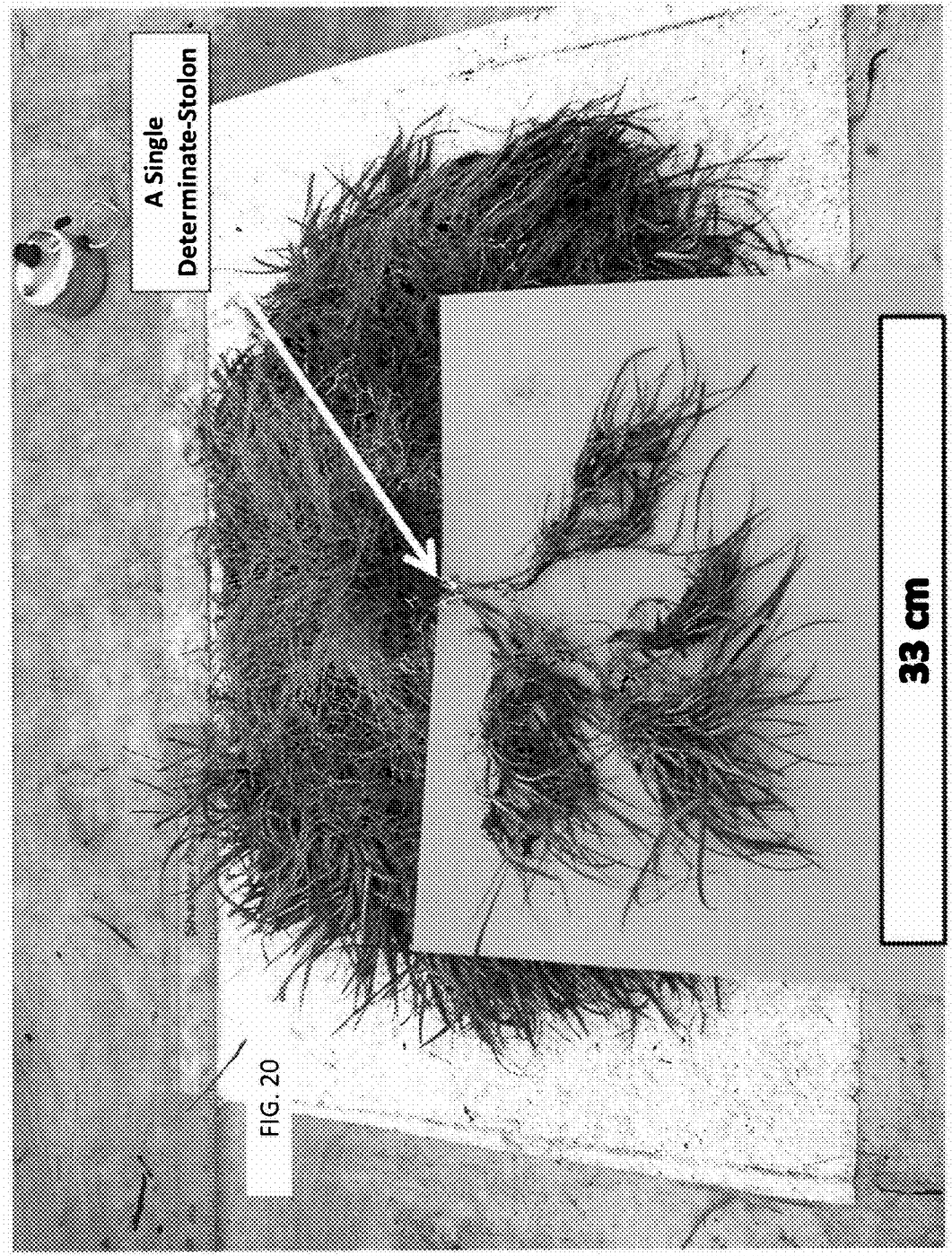
FIG. 20 is a digital image showing a single determinate-stolon of *Lolium perenne* L. subsp. *stoloniferum*.

To collect tiller and rooting node data, the plants (FIG. 15) were dug up and removed from the field (FIG. 16). The root mass was washed to clean the root mass of soil, and aid in visualizing rooting structures. To properly count rooting structures, individual peripheral tillers or determinate-stolons were dissected off from the plant. Prior to this dissection, the whole plant was photographed. The plants were then dried off, and the central crown of the rooting mass was painted using paint markers (FIG. 16). The peripheral tillers/determinate-stolons marked by the paint markers were removed from the crown (FIGS. 17 and 18). The tillers marked with the paint represented either a peripheral (outermost) tiller (FIG. 21 (right), FIG. 26 (left)) or a peripheral determinate-stolon (FIGS. 19, 20, and 21 (left), FIG. 26 (right) of the rooting crown and were all termed "Peripheral tillers." A determinate-stolon is an above-ground horizontal stem which roots at the nodes along the ground, but the apical meristem will eventually terminate with an inflorescence (e.g., *Lolium perenne* subsp. *stoloniferum*). The apical meristem of the determinate-stolon does not grow indeterminately (as do the stolons of bermudagrass or creeping bentgrass), they will eventually terminate in an inflorescence. In *L. perenne* subsp. *perenne* (e.g., Pinnacle II), the very lowermost nodes on tillers often root, but they do not produce stolons. The total number of peripheral tillers were counted as, "Number of Peripheral (Outside) Tillers."

Figure 21:
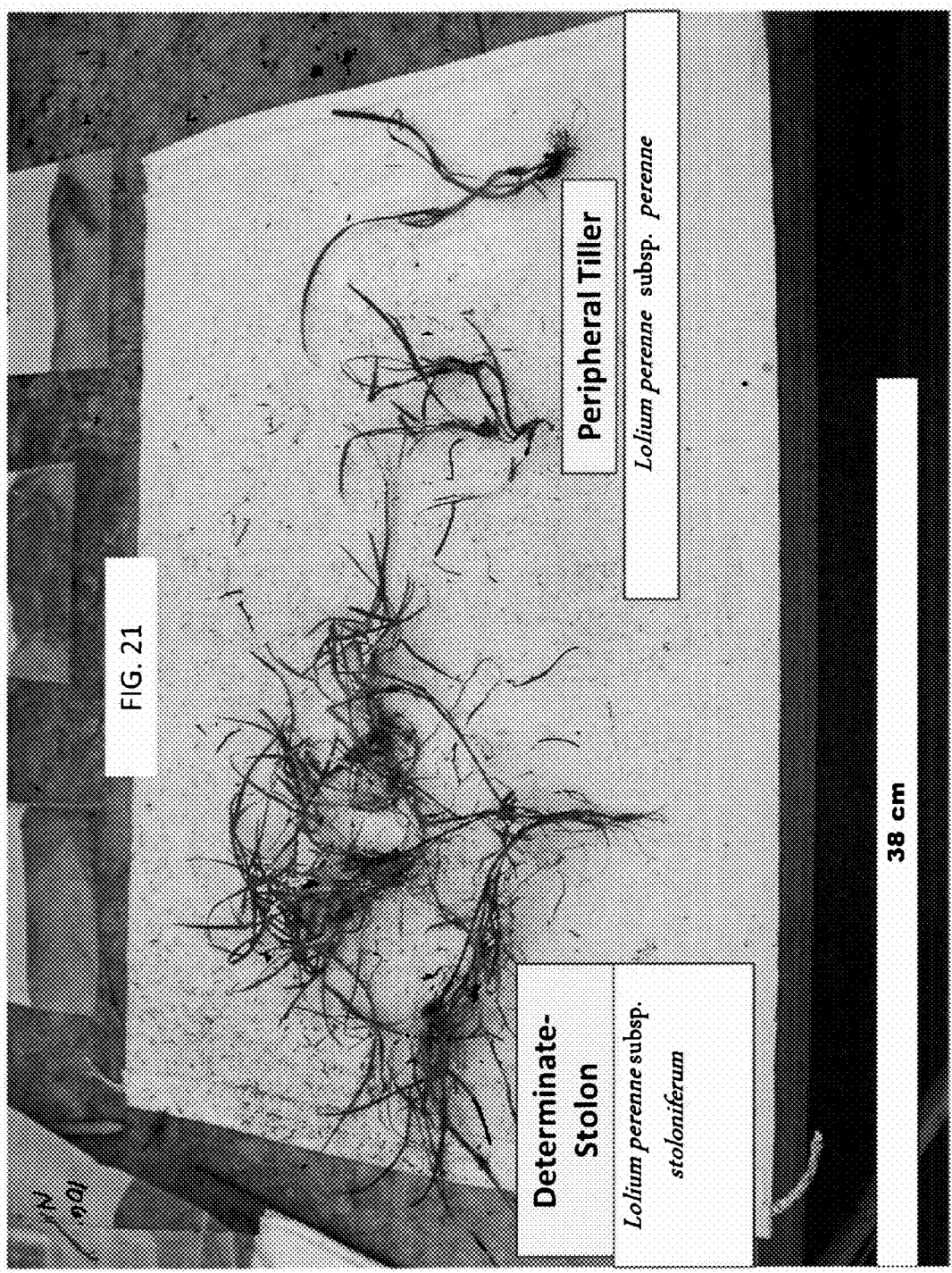
FIG. 21 is a digital image comparing the determinate-stolon of *Lolium perenne* L. subsp. *stoloniferum* 06-LpC-13 (left) with the peripheral tillers of *Lolium perenne* L. subsp. *perenne* (right).
Figure 22:
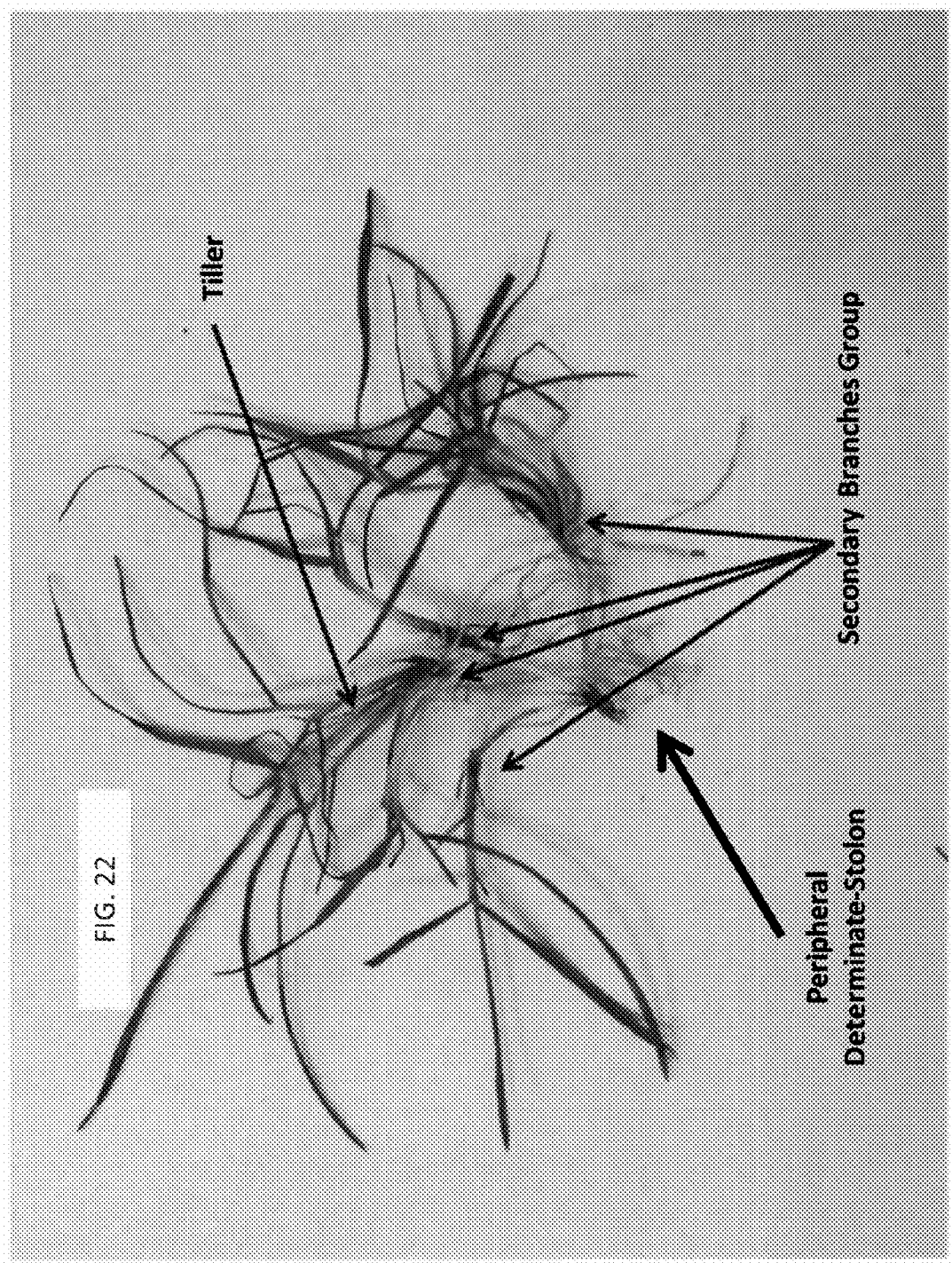
FIG. 22 is a digital image showing the tiller, peripheral determinate-stolon, and secondary branches of *Lolium perenne* L. subsp. *stoloniferum*.

The peripheral tillers were separated into two groups. The first group represented tillers which had additional rooting nodes besides the crown roots, and were called determinate-stolons (FIGS. 21 and 22). The second group represented tillers which had only the crown root, and no additional rooting nodes and were called "Peripheral Tillers without rooting nodes. The two groups were counted separately.

Figure 23:
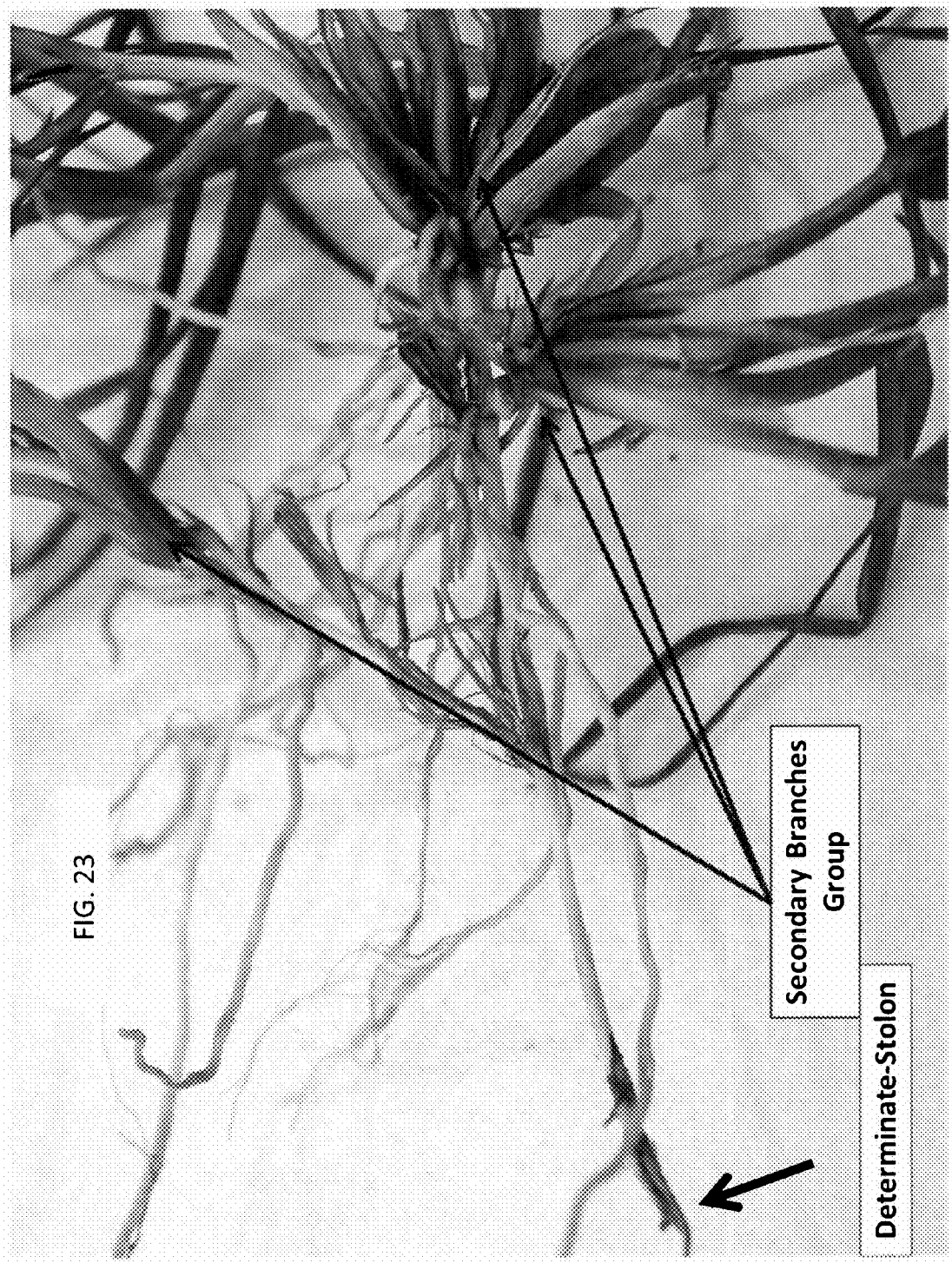
FIG. 23 is a digital image showing a close up of the determinate-stolon and secondary branches of *Lolium perenne* L. subsp. *stoloniferum*.
Figure 24:
FIGS. 24 and 25 are digital images showing a determinate-stolon of *Lolium perenne* L. subsp. *stoloniferum* 06-LpC-13.
Figure 25:

A rooting node was defined as a node on a determinate-stolon (other than the crown roots) bearing roots. The total count of rooting nodes was reported as "Total Number of Rooting Nodes" (see FIGS. 23, 24, and 25).

The length of the ten (10) longest determinate-stolon was measured using Scienceware® metric calipers. The length of the tiller/determinate-stolon was measured as the distance from the most distal rooting node to the base of the crown and shown in the columns labeled as "Total Determinate-Stolon$^3$ Length [Sum of 10 Stolons]" and "Length of Longest Determinate-Stolon$^3$ Length (mm)."

determinate-stolons increased by at least 1.3 fold relative to peripheral tillers of Pinnacle II (such as an increase of at least 1.5 fold, at least 2 fold, at least 2.5 fold, or at least 2.9 fold relative to Pinnacle II); the number of secondary tillers on determinate-stolons increased by at least 1.8 fold relative to peripheral tillers of Pinnacle II (such as an increase of at least 2 fold, at least 3 fold, at least 4 fold, or at least 4.6 fold relative to peripheral tillers of Pinnacle II); the length of the total determinate-stolon increased by at least 1.5 fold relative to peripheral tillers of Pinnacle II (such as an increase of at least 2 fold, at least 2.2 fold, or at least 2.5 fold relative to Pinnacle II); and the length of the longest determinate-stolon increased by at least 1.6 fold relative to peripheral tillers of Pinnacle II (such as an increase of at least 1.8 fold, at least 2 fold, at least 2.2 fold, or at least 2.3 fold relative to Pinnacle II).

EXAMPLE 7

Determinate-Stolon Index

This example describes a determinate-stolon index to comprehensively characterize the different morphological parameters which collectively differentiate *Lolium perenne* subsp. *stoloniferum* from *Lolium perenne* subsp. *perenne*.

The determinate-stolon index for each variety was calculated by multiplying the values in Columns 2, 3, 4, and 5 in Table 16 (Total Number of Rooting Nodes; Number Determinate-stolons (or peripheral tillers with rooting nodes the case of Pinnacle II); Secondary Tillers with Rooting Nodes;

TABLE 16

Determinate-stolon and Peripheral (Outside) Tiller Morphology of Perennial Ryegrass Cultivars under Traffic, November 2011

| Grass | Species | # of Peripheral (Outside) Tillers 1 | Total # of Rooting Nodes 2 | # Determinate-stolons 3 | Secondary Tillers on determinate-stolons 4 | Total Determinate-Stolon$^3$ length [Sum of 10 Stolons] (mm) 5 | Length of longest Determinate-Stolon$^3$ (mm) 6 |
|---|---|---|---|---|---|---|---|
| 06LpC9 | Lps$^1$ | 38 | 467 | 32 | 157 | 1387 | 188 |
| 06-LpC10 | Lps | 26 | 643 | 25 | 209 | 1395 | 176 |
| 06-LpC14 | Lps | 32 | 303 | 28 | 137 | 1095 | 168 |
| 06-LpC13 | Lps | 20 | 269 | 16 | 104 | 1040 | 164 |
| 09-LpC72 | Lps | 37 | 508 | 35 | 152 | 1108 | 157 |
| 06LpC2 | Lps | 23 | 223 | 18 | 81 | 838 | 151 |
| 06LpC12 | Lps | 26 | 242 | 22 | 98 | 858 | 136 |
| Pinnacle II | Lpp$^2$ | 14 | 107 | 12* | 45* | 553* | 83* |

$^1$Lps is *Lolium perenne* subsp. *stoloniferum*
$^2$Lpp is *Lolium perenne* subsp. *perenne*
$^3$A determinate-stolon is an above-ground horizontal stem which roots at the nodes (i.e., stolon), that does not produce shoots indeterminately, but the apical meristem will eventually terminate with an inflorescence (e.g., *Lolium perenne* subsp. *stoloniferum*).
*In the case of Pinnacle II this measurement is only a tiller measurement and not a determinate-stolon, since Pinnacle II does not produce determinate-stolons. In *L. perenne* subsp. *perenne* the lowermost nodes often root, but the plant does not produce stolons. In this type of ryegrass, the very lowermost nodes on most tillers often root but they do not form stolons.

As shown in Table 16, 06LpC varieties had more peripheral (outside) tillers; more determinate-stolons; a higher total number of rooting nodes; and more secondary tillers with rooting nodes than Pinnacle II. In addition, 06LpC varieties had a longer total determinate-stolon length than the peripheral tiller on Pinnacle II, and the length of the longest determinate-stolon was longer than the peripheral tiller on Pinnacle II. For example, in some 06LpC varieties the number of peripheral (outside) tillers increased by at least 1.4 fold relative to Pinnacle II (such as an increase of at least 1.5 fold, at least 2 fold, at least 2.5 fold, or at least 2.7 fold relative to Pinnacle II); the number of total number of rooting nodes increased by at least 2 fold relative to Pinnacle II (such as an increase of at least 3 fold, at least 3 fold, at least 4 fold, at least 5 fold, or at least 6 fold relative to Pinnacle II); the number of and Total Determinate-Stolon (or Peripheral Tillers of Pinnacle II) Length [Sum of 10 Stolons]). All of the parameters were measured on mowed space plants subjected to traffic. The determinate-stolon index is shown in Table 17.

TABLE 17

Determinate-Stolon Index

| Grass | Species | Determinate-Stolon Index |
|---|---|---|
| 06-LpC10 | Lps$^1$ | 7,276,431,064 |
| 06LpC9 | Lps | 3,321,681,740 |
| 06-LpC14 | Lps | 3,148,885,563 |
| 09-LpC72 | Lps | 2,708,164,623 |
| 06-LpC13 | Lps | 635,421,120 |

TABLE 17-continued

Determinate-Stolon Index

| Grass | Species | Determinate-Stolon Index |
|---|---|---|
| 06LpC12 | Lps | 592,466,427 |
| 06LpC2 | Lps | 560,606,200 |
| Pinnacle II | Lpp[2] | 60,750,398 |

[1]Lps is *Lolium perenne* subsp. *stoloniferum*
[2]Lpp is *Lolium perenne* subsp. *perenne*

As shown in Table 17, the 06LpC varieties have a determinate-stolon index that is at least 5-fold greater than Pinnacle II, such as an at least 6-fold, at least 7-fold, at least 8-fold, at least 9-fold, at least 10-fold, at least 20-fold, at least 30-fold, at least 50-fold, or even at least 100-fold greater determinate-stolon index than Pinnacle II.

Thus in some examples, the disclosed 06LpC varieties have a determinates stolon index of at least 500,000,000, at least 600,000,000, at least 1,000,000,000, at least 2,000,000,000, at least 3,000,000,000, or at least 7,000,000,000.

EXAMPLE 8

Genetic Fingerprinting

This example describes genetic fingerprinting of the disclosed *Lolium perenne* subsp. *stoloniferum*, as compared to other perennial ryegrass varieties.

Simple sequence repeat (SSR) fingerprinting analysis was performed on the varieties shown in Table 18, using routine methods. The grass seed samples were processed and analyzed using the ISF-EDV (International Seed Federation-Essentially Derived Variety) Protocol (Roldán-Ruiz 2008; Studer et al. 2008). Additional information on the protocol can be found in Roldán-Ruiz et al. (2000), Gilliland et al. (2001), Roldán-Ruiz et al. (2001), and Roldán-Ruiz et al. (2001a). For the first 10 seed lots in Table 18, 96 plants for each variety were generated and two bulked DNA samples were prepared (each containing leaf segments of 20 randomly selected plants). Equal amounts of tissue from 20 plants for each variety was bulked. This bulked tissue sample was used for one DNA-extraction. This was done for two independent sets of 20 plants per variety.

TABLE 18

Perennial ryegrass varieties fingerprinted.

| Dendogram Code | Source | Species |
|---|---|---|
| 1 LpC2 | 06LpC 2 | *Lolium perenne* subsp. *stoloniferum* |
| 2 LpC9 | 06LpC 9 | *Lolium perenne* subsp. *stoloniferum* |
| 3 LpC10 | 06LpC 10 | *Lolium perenne* subsp. *stoloniferum* |
| 4 LpC12 | 06LpC 12 | *Lolium perenne* subsp. *stoloniferum* |
| 5 LpC13 | 06LpC 13 | *Lolium perenne* subsp. *stoloniferum* |
| 6 LpC14 | 06LpC 14 | *Lolium perenne* subsp. *stoloniferum* |
| 7 LpC72 | 09-LpC 72 | *Lolium perenne* subsp. *stoloniferum* |
| 8 LpC Blend 10-13-14 | 06LpC 10 + 06LpC 13 + 06LpC 14 | *Lolium perenne* subsp. *stoloniferum* |
| 9 Pinacle II | Pinnacle II | *Lolium perenne* subsp. *perenne* |
| 10 Natural Knit | Natural Knit - Commercial Lot | *Lolium perenne* |
| 11 ATCC | ATCC No. PTA-8792 | *Lolium perenne* |

In addition, American Type Culture Collection (ATCC) deposit number PTA-8792 from the (Manassas, Va., USA) was acquired and processed. The seed was germinated and freeze-dried leaf materials from 25 plants analyzed.

The samples were coded upon arrival and blind-analyzed. The person who did the scoring did not know the identity of the samples.

The ISF protocol was used (four multiplex sets to amplify a total of 31 SSR loci), and generated a 1/0 table for a total of 50 DNA-samples. The 1/0 scoring table contained information for 415 polymorphic markers and contained no missing data. The data analysis was as carried out and a dendrogram generated (FIG. 27).

FIG. 27 shows that the disclosed *Lolium perenne* L. subsp. *stoloniferum* varieties (LpC) are genetically different from other perennial ryegrasses, including ATCC deposit number PTA-8792. In addition, pairs of samples derived from the same seed lot (A/B) cluster together, with the exception of Pinnacle II-A and II-B.

EXAMPLE 9

Production of LpC Grasses

LpC (such as 06-LpC-10; 06-LpC-13; 06-LpC-14; 06-LpC-9; 06-LpC-2; 06-LpC-12, and 09-LpC-72) can be grown under normal conditions for growing perennial ryegrasses, and bulk seed for large-scale planting can be obtained by methods known in certified seed production. For example, bulk seed may be produced by planting LpC seeds obtained from either NCIMB (Deposit Nos: NCIMB 41778; NCIMB 41779; NCIMB 41780; NCIMB 41781; NCIMB 41782; NCIMB 41783; or NCIMB 41784) or Barenbrug USA, Inc., allowing the mature plants to produce seed by cross-pollination with each other and then collecting the seed. Standard precautions should be taken to prevent cross-pollination from other grasses, such as growing the variety in an isolated plot of sterilized soil, removing adjacent vegetation, etc. The LpC seeds deposited with NCIMB are breeder seeds; propagation of plants from these seeds can be performed under standard conditions known to those skilled in the art.

EXAMPLE 10

Introducing Traits of LpC into Other Grass Varieties

The morphological and physiological characteristics of LpC (such as any of 06-LpC-10; 06-LpC-13; 06-LpC-14; 06-LpC-9; 06-LpC-2; 06-LpC-12, and 09-LpC-72), including the ability to produce determinate-stolons and produce a turf that is traffic resistant, can be introduced into other grass varieties by conventional breeding techniques. For example, LpC (such as 06-LpC-10; 06-LpC-13; 06-LpC-14; 06-LpC-9; 06-LpC-2; 06-LpC-12, and 09-LpC-72) can be grown in pollination proximity to another variety of perennial ryegrass, allowing cross-pollination to occur between LpC and the other variety, and then harvesting the hybrid seeds. Plants grown from these hybrid seeds can then be tested for the maintenance of the molecular characteristics described herein for LpC, and/or the plants can simply be observed to see if they display the same growth characteristics described in the above tables.

For example, plants grown from these hybrid seeds can be tested for any of the morphological characteristics described herein, for the production of determinate-stolons, and/or for the production of a turf that is traffic resistant. In this way, the determinate-stolons and traffic resistance may be combined with other desirable plant characteristics. Thus, the provision of LpC enables the production of progeny plants of LpC having determinate-stolons and traffic resistance. "Progeny plants" of LpC are any plants that are the offspring of a cross between LpC and any other plant or plants. Progeny plants also include successive generations of the offspring, for example those selected for determinate-stolons and traffic resistance using the methods described herein. First-generation progeny plants may retain the determinate-stolon and traffic resistance characteristics of the LpC parent. However, if a first-generation progeny plant does not retain the desired level of determinate-stolons and traffic resistance observed with LpC, subsequent generations of offspring can be recycled for determinate-stolons and traffic resistance which have at least the same determinate-stolons and traffic resistance characteristics of LpC described herein. In one embodiment, subsequent generations of offspring can have determinate-stolons and traffic resistance that exceed that of LpC.

In addition, LpC can be used as transformation targets for the production of transgenic grasses. In certain embodiments, the present disclosure contemplates the transformation of cells derived from LpC with at least one transgene. For example, transgenes that can be used, include, but are not limited to, transgenes that confer resistance to herbicides, insect, disease (viral, bacterial, fungal, nematode) or drought resistance, heat tolerance, standability, prolificacy, salt damage resistance, low and high pH tolerance, and quality are useful. Examples of such genes and methods of transforming plants are described in U.S. Pat. No. 6,025,545 to Lundquist et al., herein incorporated by reference.

REFERENCES

Anon. 2001. Turfgrass Seed 2001. Sports Turf Research Institute, Bingley, West Yorkshire, UK Aramendia, L. A. Inda. 2005. El género Lolium: Claves dicotómicas. Rev. Real Academia de Ciencias. Zaragoza. 60:143-155.

Beddows, A. R. 1953. The ryegrasses in British agriculture: a survey. Welsh Plant Breeding Station Bulletin, Ser. H, No. 17:1-81.

Bonos, S. A., E. Watkins, J. A. Honig, M. Sosa, J. A. Molnar, and W. A. Meyer. 2001. Breeding cool-season turfgrasses for wear tolerance using a wear simulator. International Turfgrass Society Research Journal 9:137-145.

Canaway, P. M. 1976. A Differential Slip Wear Machine (D.S.I) for the Artificial Simulation of Turfgrass Wear. Journal of the Sports Turf Research Institute. 52:92-99.

Canaway, P. M. 1981. Wear tolerance of turfgrass species. Journal of the Sports Turf Research Institute. 57: 65-83.

Canaway, P. M. 1981b. Comparison of Real and Artificial Wear. *Journal of the Sports Turf Research Institute.* 57: 108-121.

Cockerham, S. T. 1989. Cleated-Shoe Traffic Concentration on a Football Field. 1989. California Turfgrass Culture 39(3-4):11-12.

Cockerham, S. T. and D. J. Brinkman. 1989. A Simulator for Cleated-Shoe Sports Traffic on Turfgrass Research Plots. California Turfgrass Culture 39(3-4):9-10.

Cockerham, S. T., V. A. Gibeault, J. Van Dam, and M. K. Leonard. 1989. Tolerance of Cool Season Turfgrasses to Sports Traffic. California Turfgrass Culture 39(3-4):12-14.

Edmond, D. B. 1964. Some effects of sheep treading on the growth of 10 pasture species. New Zealand Journal of Agricultural Research 7:1-16.

Ellis, C. J. 1981. An experimental approach to wear tolerance in *Lolium perenne*. Ph.d. Thesis. University of Liverpool, United Kingdom.

Essad, S. 1954. Contribution à la sytèmatique du genere *Lolium*. Ministère de l'Agriculture. Annales de l'Institute Natlionale Recherche Agronomie, Paris. Amelioration des Plantes 4:325-351.

Fei, Y-j. 1999. A new species of the genus *Lolium* L. (Poaceae) from Hubei (China). Guihaia 19:205-206.

Gilliland et al., 2001. Estimating genetic conformity between related ryegrass (*Lolium*) varieties, I. Morphology and Biochemical characterisation. Molecular Breeding 6/6: 569-580.

Harris et al., 1979. Observations on the spread of perennial ryegrass by stolons in a lawn. New Zealand Journal of Agricultural Research 22:61-68.

Hayes, P. 1971. Stoloniferous perennial ryegrass (*Lolium perenne*) in Northern Ireland Paddocks. Record of Agricultural Research, Ministry of Agriculture for Northern Ireland 19:63-64.

Henderson, et al., 2005. A New Apparatus to Simulate Athletic Field Traffic: The Cady Traffic Simulator. Agron. J. 97:1153-1157.

Jenkin, T. J. 1936. Natural selection of grasses in relation to the grasses. In, A Discussion on the Present State of the Theory of Natural Selection. Proc. Roy. Soc., Ser. B. 121: 52-56.

Kydd, D. D. 1966. The effect of intensive sheep stocking over a five-year period on the development and production of the sward. Journal of the British Grassland Society 21:284-288.

Lawson, C. 1836. *Lolium*—Ryegrass. Pp. 102-113. In. The Agriculturist's Manual: Agricultural Plants Cultivated in Europe, Including practical observations respecting those suited to the Climate of Great Britain, and forming a Report of Lawson's Agricultural Museum in Edinburgh. By Peter Lawson & Son. William Blackwood and Sons, Edinburgh.

Ledeboer, F. 2010. Spreading ryegrass. U.S. Pat. No. 7,696,418 issued Apr. 13, 2010.

Lush, W. M. and M. E. Rogers. 1992. Cutting heights and the biomass and tiller density of *Lolium perenne* amenity turfs. J. Applied Ecology 29:611-618.

Mitchell, K. J. 1956. The influence of light and temperature on the growth of pasture species. Proceedings of the Seventh International Grassland Congress: 58-69.

Oakley, R. A. and M. W. Evans. 1921. Rooting stems in Timothy. Journal of Agricultural Research 21(3):173-178+2 plates.

Plot, R. 1677. The Natural History of Oxfordshire. Oxford University Press. Roldán-Ruiz et al., 2000. AFLP markers reveal high polymorphic rates in ryegrasses. Molecular Breeding 6: 125-134.

Roldán-Ruiz et al., 2001. Estimating genetic conformity between related ryegrass (*Lolium*) varieties, II. AFLP characterisation. Molecular Breeding 6/6: 593-602.

Roldán-Ruiz et al., 2001a. A comparative study of molecular and morphological methods of describing relationships between perennial ryegrass (*Lolium perenne* L.) varieties. Theoretical and Applied Genetics 103: 1138-1150.

Roldán-Ruiz, I. 2008. Development of a protocol based on the use of SSR markers to be used in disputes of essential derivation in *Lolium perenne* L. ILVO On-Line Publication: www.ilvo.vlaanderen.be/EN/Research/Growthand-Development/Phenotypingandgen otyping/SSRmarkers-basedprotocol/tabid/2336/language/en-US/Default.aspx Studer et al., 2008. Expressed sequence tag-derived microsatellite markers of perennial ryegrass. Molecular Breeding, 21 (4): 533-548.

Scholz, H., C. Stierstorfer, and M. Gaisberg. 2000. *Lolium edwardii* sp. nova (Gramineae) and its relationship with *Schedonorus* sect. *Plantynia* Dumort. Feddes Repertorium 111:561-565.

Shildrick, J. P. 1981. Shoot Numbers, stem bases and persistence in artificially worn perennial ryegrass. Journal of the Sports Turf Research Institute 57:84-107.

Sinclair, G. 1826. *Hortus Gramineus Woburnesis*. 3$^{rd}$ Edition. James Ridgeway, London. 438 pp.

Terrell, E. E. 1968. A Taxonomic Revision of the Genus *Lolium*. USDA-ARS, Technical Bulletin No. 1392. 65 pp.

Terrell. E. E. 2007. *Lolium*. In Magnoliophyta: Commelinidae (In part): Poaceae, part 1. Flora of North America North of Mexico, volume 24. Pp. 454-459. Eds. Barkworth, M. E., K. M. Capels, S. Long, and M. B. Piep. Oxford University Press, New York.

Thorogood, D. 2003. Chapter 7. Perennial Rygrass (*Lolium perenne* L.). In, Turfgrass Biology, Genetics, and Breeding. Eds. M. D. Casler and R. D. Duncan. John Wiley & Sons, Inc. Hoboken, N.J. Pp 75-105.

Vanini et al., 2007. Evaluating Traffic Stress by the Brinkman Traffic Simulator and Cady Traffic Simulator on a Kentucky Bluegrass Stand. Crop Sci. 47:782-786.

White, J. 1981. The allometric interpretation of the self thinning rule. J. Theor. Biol. 89:475-500.

Wipff, J. K. 2010. A New Combination in *Lolium perenne* (POACEAE:POEAE); *L. perenne* subsp. *stoloniferum*. J. Bot. Institute of Texas 4(2):6383-684.

Youngner, V. B. 1961. Accelerated wear tests on turfgrasses. Agron. J. 53:217-218.

In view of the many possible embodiments to which the principles of the disclosure may be applied, it should be recognized that the illustrated embodiments are only examples and should not be taken as limiting the scope of the disclosure. Rather, the scope of the invention is defined by the following claims. We therefore claim as our invention all that comes within the scope and spirit of these claims.

We claim:

1. A *Lolium perenne* ssp. *stoloniferum* perennial ryegrass plant comprising a determinate-stolon index of at least 500,000,000, representative seed has been deposited under National Collection of Industrial, Food and Marine Bacteria (NCIMB) Deposit No. NCIMB 41778; NCIMB 41779; NCIMB 41780; NCIMB 41781; NCIMB 41782; NCIMB 41783; and NCIMB 41784.

2. The *Lolium perenne* ssp. *stoloniferum* perennial ryegrass plant of claim 1, wherein the plant has a crown perimeter of at least 80 cm after 2 years of growth and continual mowing.

3. The *Lolium perenne* ssp. *stoloniferum* perennial ryegrass plant of claim 1, wherein a seeded row of the plant has a crown spread of at least 23 cm after 2 years of growth and mowing.

4. The *Lolium perenne* ssp. *stoloniferum* perennial ryegrass plant of claim 1, wherein the plant has a crown perimeter spread of at least 56 cm after mowing, artificial traffic and 1 year of growth, or has a crown spread of at least 69 cm after mowing, artificial traffic and 2 years of growth.

5. The *Lolium perenne* ssp. *stoloniferum* perennial ryegrass plant of claim 1, wherein a row of the plant has a crown spread of at least 13 cm after mowing, artificial traffic and 1 year of growth or a crown spread of at least 19 cm after mowing, artificial traffic and 2 years of growth.

6. The *Lolium perenne* ssp. *stoloniferum* perennial ryegrass plant of claim 1, wherein the plant has a crown perimeter of at least 77 cm after mowing and artificial traffic and at least 12 months of growth.

7. The *Lolium perenne* ssp. *stoloniferum* perennial ryegrass plant of claim 1, wherein the plant can regenerate after artificial traffic and has an increased crown perimeter of at least 3 cm within at least two months after artificial traffic has stopped.

8. The *Lolium perenne* ssp. *stoloniferum* perennial ryegrass plant of claim 1, wherein the plant has a surface area of at least 275 cm$^2$ after mowing, artificial traffic, and at least 12 months of growth.

9. The *Lolium perenne* ssp. *stoloniferum* perennial ryegrass plant of claim 1, wherein the plant can regenerate after artificial traffic and has an increased surface area of at least 2 cm$^2$ within at least two months after artificial traffic has stopped.

10. The *Lolium perenne* ssp. *stoloniferum* perennial ryegrass plant of claim 1, wherein the plant has:
at least 20 peripheral tillers;
at least 200 total rooting nodes;
at least 16 determinate-stolons;
at least 70 secondary tillers on determinate stolons;
a total determinate-stolon length of at least 800 mm for the sum of 10 determinate-stolons;
a longest determinate-stolon having a length of at least 100 mm; or
combinations thereof, after mowing, traffic simulation and about 1 year of growth.

11. The *Lolium perenne* ssp. *stoloniferum* perennial ryegrass plant of claim 1, wherein the determinate-stolon index is at least 5-fold greater than Pinnacle II.

12. The *Lolium perenne* ssp. *stoloniferum* perennial ryegrass plant of claim 1, wherein:
at least 2%, at least 3%, at least 5%, at least 8%, at least 10%, or at least 15% of the plants have determinate-stolons after traffic simulation and mowing.

13. The *Lolium perenne* ssp. *stoloniferum* perennial ryegrass plant of claim 1, wherein the ryegrass comprises one or more of the morphological and physiological properties of a grass plant grown from a seed deposited under NCIMB Deposit No. NCIMB 41778; NCIMB 41779; NCIMB 41780; NCIMB 41781; NCIMB 41782; NCIMB 41783; or NCIMB 41784.

14. Sod, comprising the *Lolium perenne* ssp. *stoloniferum* perennial ryegrass plant of claim 1.

15. Turf, comprising the *Lolium perenne* ssp. *stoloniferum* spp. perennial ryegrass plant of claim 1.

16. Progeny of the *Lolium perenne* ssp. *stoloniferum* perennial ryegrass plant of claim 1, wherein the progeny comprise one or more of the morphological and physiological properties of a perennial ryegrass plant grown from a seed deposited under NCIMB Deposit No. NCIMB 41778; NCIMB 41779; NCIMB 41780; NCIMB 41781; NCIMB 41782; NCIMB 41783; or NCIMB 41784.

17. Seed of the *Lolium perenne* ssp. *stoloniferum* perennial ryegrass plant of claim 1, wherein the seed produces a perennial ryegrass plant comprising one or more of the morphological and physiological properties of a perennial ryegrass plant grown from a seed deposited under NCIMB Deposit No. NCIMB 41778; NCIMB 41779; NCIMB 41780;

NCIMB 41781; NCIMB 41782; NCIMB 41783; or NCIMB 41784.

18. A seed mixture, comprising the seed of claim 15.

19. A vegetative sprig or clone of the *Lolium perenne* ssp. *stoloniferum* perennial ryegrass plant of claim 1.

20. A perennial ryegrass plant produced from the *Lolium perenne* ssp. *stoloniferum* perennial ryegrass plant of claim 1 by transformation with a transgene that confers upon the perennial ryegrass plant resistance to an herbicide, resistance to an insect, resistance to a bacterial disease, resistance to a viral disease, resistance to a fungal disease, resistance to a nematode, drought tolerance, heat tolerance, low and high soil pH levels, or salt tolerance, wherein the produced perennial ryegrass plant comprises a determinant stolon index of at least 500,000,000.

21. Seed resulting from crossing the *Lolium perenne* ssp. *stoloniferum* perennial ryegrass plant of claim 1 with a second perennial ryegrass plant, wherein the seed produces a perennial ryegrass plant comprising a determinant stolon index of at least 500,000,000.

22. A *Lolium perenne* ssp. *stoloniferum* perennial ryegrass plant grown from the seed of claim 21, wherein the *Lolium perenne* ssp. *stoloniferum* perennial ryegrass plant comprises a determinant stolon index of at least 500,000,000.

23. Sod or turf comprising the *Lolium perenne* ssp. *stoloniferum* perennial ryegrass plant of claim 22.

24. A method of producing a *Lolium perenne* ssp. *stoloniferum* perennial ryegrass plant, comprising:
    crossing a first *Lolium perenne* ssp. *stoloniferum* perennial ryegrass plant with at least one other perennial ryegrass plant to produce at least one seed, wherein the first grass plant is the *Lolium perenne* ssp. *stoloniferum* perennial ryegrass of claim 1;
    harvesting the seed; and
    germinating the seed to produce at least one progeny *Lolium perenne* ssp. *stoloniferum* perennial ryegrass plant.

25. A *Lolium perenne* ssp. *stoloniferum* perennial ryegrass plant produced by the method of claim 24, wherein the *Lolium perenne* ssp. *stoloniferum* perennial ryegrass plant comprises a determinant stolon index of at least 500,000,000.

26. Sod or turf comprising the *Lolium perenne* ssp. *stoloniferum* perennial ryegrass plant of claim 25.

27. A vegetative sprig or clone of the *Lolium perenne* ssp. *stoloniferum* perennial ryegrass plant of claim 25.

28. A *Lolium perenne* ssp. *stoloniferum* perennial ryegrass plant produced from the *Lolium perenne* ssp. *stoloniferum* grass plant of claim 25 by transformation with a transgene that confers upon the perennial ryegrass plant resistance to an herbicide, resistance to an insect, resistance to a bacterial disease, resistance to a viral disease, resistance to a fungal disease, resistance to a nematode, drought tolerance, heat tolerance, low and high soil pH levels, or salt tolerance, wherein the produced *Lolium perenne* ssp. *stoloniferum* perennial ryegrass plant comprises a determinant stolon index of at least 500,000,000.

29. *Lolium perenne* ssp. *stoloniferum* perennial ryegrass seed from 06-LpC-2; 06-LpC-9; 06-LpC-10; 06-LpC-12; 06-LpC-13; 06-LpC-14, or 09-LpC-72, deposited as NCIMB Deposit No: NCIMB 41778; NCIMB 41779; NCIMB 41780; NCIMB 41781; NCIMB 41782; NCIMB 41783; and NCIMB 41784, respectively.

30. Turf or sod, comprising a *Lolium perenne* ssp. *stoloniferum* perennial ryegrass plant germinated from the *Lolium perenne* ssp. *stoloniferum* perennial ryegrass seed of claim 29.

31. A *Lolium perenne* ssp. *stoloniferum* perennial ryegrass plant germinated from the seed of claim 29.

32. A method of producing *Lolium perenne* ssp. *stoloniferum* perennial ryegrass seed, comprising
    planting the *Lolium perenne* ssp. *stoloniferum* perennial ryegrass seed of claim 29 under conditions that result in the germination of the seed, growth of grass plants and setting of progeny seed; and
    harvesting the progeny *Lolium perenne* ssp. *stoloniferum* perennial ryegrass seed.

33. *Lolium perenne* ssp. *stoloniferum* perennial ryegrass seed produced by the method of claim 32, wherein a perennial ryegrass plant grown from the perennial ryegrass seed comprises a determinant stolon index of at least 500,000,000.

34. A mixture of grass seed comprising the grass seed of claim 33.

35. A method of selecting for a *Lolium perenne* ssp. *stoloniferum* grass plant comprising a determinant stolon index of at least 500,000,000, comprising:
    exposing a turf plot planted with a *Lolium perenne* ssp. *stoloniferum* grass to natural traffic or a traffic simulator from May, or when grasses comes out of winter and begins actively growing, until the first frost in the fall;
    mowing the turf plot at least once a week to a height of between 0.5-2 inches; and
    selecting one or more *Lolium perenne* ssp. *stoloniferum* grass plants comprising a determinant stolon index of at least 500,000,000 and that survive after at least two years.

36. The method of claim 35, wherein the traffic simulator weighs at least 2000 lbs.

37. The method of claim 35, wherein the traffic simulator is applied once or twice a week with 1-3 passes.

38. The method of claim 35, wherein the natural traffic comprises at least two, at least three, at least four, or at least five sports games per week.

39. The method of claim 35, wherein no supplemental irrigation is provided for the *Lolium perenne* ssp. *stoloniferum* grass plant and no disease control is performed.

40. The method of claim 35, wherein the selected *Lolium perenne* ssp. *stoloniferum* grass plant has a crown perimeter spread of at least 80 cm after mowing and 2 years of growth.

41. The method of claim 35, wherein the selected *Lolium perenne* ssp. *stoloniferum* grass plant has:
    at least 20 peripheral tillers;
    at least 200 total rooting nodes;
    at least 16 determinate-stolons;
    at least 70 secondary tillers on determinate stolons;
    a total determinate-stolon length of at least 800 mm for the sum of 10 determinate-stolons; or
    a longest determinate-stolon having a length of at least 100 mm.

42. The method of claim 35, further comprising collecting seed from the selected *Lolium perenne* ssp. *stoloniferum* grass plants.

43. A *Lolium perenne* ssp. *stoloniferum* grass plant comprising a determinate-stolon index of at least 500,000,000 selected by the method of claim 35.

44. A *Lolium perenne* ssp. *stoloniferum* perennial ryegrass plant produced by crossing a *Lolium perenne* ssp. *stoloniferum* perennial ryegrass having determinate-stolons grown from a 06-LpC-2; 06-LpC-9; 06-LpC-10; 06-LpC-12; 06-LpC-13; 06-LpC-14, or 09-LpC-72 seed deposited under NCIMB Deposit No. NCIMB 41778; NCIMB 41779; NCIMB 41780; NCIMB 41781; NCIMB 41782; NCIMB 41783; or NCIMB 41784, respectively to another grass variety, wherein the *Lolium perenne* ssp. *stoloniferum* perennial ryegrass produced has a determinant stolon index of at least 500,000,000.

45. The *Lolium perenne* ssp. *stoloniferum* perennial ryegrass plant of claim 44, wherein the other grass variety is a *Lolium multiflorum, L. rigidum, Festuca pratensis, Festuca* spp., *Lolium* spp., *Schedonorus* spp.

46. Grass seeds resulting from the *Lolium perenne* ssp. *stoloniferum* perennial ryegrass plant of claim 44.

47. A method of producing a *Lolium perenne* ssp. *stoloniferum* perennial ryegrass plant, comprising:
   crossing the *Lolium perenne* ssp. *stoloniferum* perennial ryegrass of claim 1 with at least one other grass species to produce at least one interspecific hybrid seed;
   harvesting the interspecific hybrid seed; and
   germinating the interspecific hybrid seed to produce at least one progeny *Lolium perenne* ssp. *stoloniferum* perennial ryegrass plant, wherein the progeny *Lolium perenne* ssp. *stoloniferum* perennial ryegrass plant has a determinant stolon index of at least 500,000,000.

48. The method of claim 47, wherein the at least one other grass species is a ryegrass, *Festuca* spp., or *Schedonorus* spp..

49. A method of producing a *Lolium perenne* ssp. *stoloniferum* perennial ryegrass plant, comprising:
   increasing the chromosome number of the *Lolium perenne* ssp. *stoloniferum Lolium* spp. perennial ryegrass of claim 1 to produce at least one seed;
   harvesting the seed; and
   germinating the seed to produce at least one progeny *Lolium perenne* ssp. *stoloniferum* perennial ryegrass plant, wherein the progeny *Lolium perenne* ssp. *stoloniferum* perennial ryegrass plant has a determinant stolon index of at least 500,000,000.

50. A method of producing a *Lolium perenne* ssp. *stoloniferum* perennial ryegrass plant, comprising:
   decreasing the chromosome number of the *Lolium perenne* ssp. *stoloniferum Lolium* spp. perennial ryegrass of claim 1 to produce at least one seed;
   harvesting the seed; and
   germinating the seed to produce at least one progeny *Lolium perenne* ssp. *stoloniferum* perennial ryegrass plant, wherein the progeny *Lolium perenne* ssp. *stoloniferum* perennial ryegrass plant has a determinant stolon index of at least 500,000,000.

* * * * *